US012239691B2

(12) United States Patent
Burshtein et al.

(10) Patent No.: US 12,239,691 B2
(45) Date of Patent: Mar. 4, 2025

(54) FORMULATIONS FOR ORAL ADMINISTRATION OF ACTIVE AGENTS

(71) Applicant: Entera Bio Ltd., Jerusalem (IL)

(72) Inventors: Gregory Burshtein, Modiln (IL); Ariel Rothner, Jerusalem (IL); Phillip M. Schwartz, Jerusalem (IL); Hillel Galitzer, Yad Binyamin (IL)

(73) Assignee: Entera Bio Ltd., Jerusalem (IL)

( * ) Notice: Subject to any disclaimer, the term of this patent is extended or adjusted under 35 U.S.C. 154(b) by 0 days.

(21) Appl. No.: 16/326,213

(22) PCT Filed: Aug. 17, 2017

(86) PCT No.: PCT/IL2017/050920
§ 371 (c)(1),
(2) Date: Feb. 17, 2019

(87) PCT Pub. No.: WO2018/033927
PCT Pub. Date: Feb. 22, 2018

(65) Prior Publication Data
US 2019/0209657 A1 Jul. 11, 2019

Related U.S. Application Data

(60) Provisional application No. 62/375,989, filed on Aug. 17, 2016.

(51) Int. Cl.
*A61K 9/40* (2006.01)
*A61K 9/00* (2006.01)
*A61K 9/20* (2006.01)
*A61K 9/28* (2006.01)
*A61K 38/29* (2006.01)
*A61K 47/18* (2017.01)
*A61P 19/08* (2006.01)
*A61P 19/10* (2006.01)

(52) U.S. Cl.
CPC ............ *A61K 38/29* (2013.01); *A61K 9/0053* (2013.01); *A61K 9/2013* (2013.01); *A61K 9/2095* (2013.01); *A61K 9/2806* (2013.01); *A61K 47/18* (2013.01); *A61P 19/08* (2018.01); *A61P 19/10* (2018.01); *A61K 9/0056* (2013.01)

(58) Field of Classification Search
CPC ...... A61K 9/20; A61K 9/2004; A61K 9/2009; A61K 9/2022; A61K 9/48; A61K 9/4808; A61K 9/50
See application file for complete search history.

(56) References Cited

U.S. PATENT DOCUMENTS

| | | | |
|---|---|---|---|
| 5,360,793 A | 11/1994 | Brooks | |
| 5,780,057 A | 7/1998 | Conte et al. | |
| 6,531,152 B1 | 3/2003 | Lerner et al. | |
| 6,632,451 B2 | 10/2003 | Penhasi et al. | |
| 8,110,547 B2 | 2/2012 | Lee et al. | |
| 8,673,352 B2 | 3/2014 | Sowden | |
| 9,186,412 B2 | 11/2015 | Kidron et al. | |
| 10,010,503 B2 | 7/2018 | Kidron et al. | |
| 10,472,608 B2 | 11/2019 | Bader et al. | |
| 10,583,177 B2* | 3/2020 | Burshtein | A61K 9/2054 |
| 10,704,661 B2 | 7/2020 | Gilmore | |
| 12,076,373 B2 | 9/2024 | Burshtein et al. | |
| 2005/0054557 A1 | 3/2005 | Goldberg | |
| 2006/0078622 A1 | 4/2006 | Majuru et al. | |
| 2006/0078623 A1 | 4/2006 | Dhoot et al. | |
| 2006/0233881 A1 | 10/2006 | Sowden | |
| 2006/0234913 A1 | 10/2006 | Arbit et al. | |
| 2007/0087957 A1 | 4/2007 | Kidron | |
| 2007/0155664 A1* | 7/2007 | Ranklove | A61K 9/5084 424/464 |
| 2007/0178155 A1 | 8/2007 | Jiang | |
| 2008/0200380 A1 | 8/2008 | Lee et al. | |
| 2009/0155315 A1* | 6/2009 | Finkelmeier | A61J 3/10 264/241 |
| 2010/0022480 A1* | 1/2010 | Leonard | A61K 31/20 514/103 |
| 2010/0255087 A1* | 10/2010 | Coulter | A61K 9/5015 424/457 |
| 2010/0285098 A1 | 11/2010 | Haley | |
| 2010/0303901 A1 | 12/2010 | Shimoni et al. | |
| 2011/0142800 A1* | 6/2011 | Kidron | A61K 38/56 514/7.7 |

(Continued)

FOREIGN PATENT DOCUMENTS

| | | |
|---|---|---|
| CA | 2220301 | 12/1996 |
| CA | 2626933 | 5/2007 |

(Continued)

OTHER PUBLICATIONS

Cosman et al. "Effect of Transdermal Teriparatide Administration on Bone Mineral Density in Postmenopausal Women", The Journal of Clinical Endocrinology and Metabolism, 95(1): 151-158, Published Online Oct. 26, 2009.
Office Action Dated Dec. 22, 2019 From the Israel Patent Office Re. Application No. 253802 and Its Translation Into English. (7 Pages).
Office Action Dated Dec. 23, 2019 From the Israel Patent Office Re. Application No. 253804 and Its Translation Into English. (9 Pages).

(Continued)

*Primary Examiner* — Micah Paul Young

(57) ABSTRACT

Pharmaceutical compositions comprising a therapeutically active agent and an absorption enhancer such as NAC, NAD, 5-CNAC, 4-MOAC, 4-CNAB or a salt thereof, for use in the treatment of a condition treatable by said therapeutically active agent, are provided. The compositions are for concomitant oral administration of two or more of the unit dosage form, which form together a therapeutically effective amount of the therapeutically active agent and an effective amount of the absorption enhancer. Multi-dose compositions comprising the two or more of the unit dosage form are also provided.

30 Claims, 4 Drawing Sheets

(56) References Cited

U.S. PATENT DOCUMENTS

| | | | |
|---|---|---|---|
| 2011/0182985 A1* | 7/2011 | Coughlan | A61K 31/727 424/452 |
| 2011/0250238 A1 | 10/2011 | Sangalli et al. | |
| 2012/0189666 A1 | 7/2012 | Dhoot et al. | |
| 2013/0138221 A1 | 5/2013 | Junker et al. | |
| 2013/0224300 A1 | 8/2013 | Maggio | |
| 2015/0050355 A1 | 2/2015 | Pipkin et al. | |
| 2015/0250729 A1* | 9/2015 | Azria | A61K 9/2095 514/11.8 |
| 2018/0021272 A1 | 1/2018 | Burshtein et al. | |
| 2018/0028622 A1 | 2/2018 | Burshtein et al. | |
| 2018/0036234 A1 | 2/2018 | Burshtein et al. | |
| 2018/0036382 A1 | 2/2018 | Burshtein et al. | |
| 2018/0050096 A1 | 2/2018 | Burshtein et al. | |
| 2020/0138913 A1 | 5/2020 | Burshtein et al. | |

FOREIGN PATENT DOCUMENTS

| | | | |
|---|---|---|---|
| CN | 1162917 | 10/1997 | |
| CN | 1543357 | 11/2004 | |
| CN | 1671418 | 9/2005 | |
| CN | 1816324 | 8/2006 | |
| CN | 101610784 | 12/2009 | |
| CN | 102123697 | 7/2011 | |
| EP | 0943336 | 9/1999 | |
| EP | 1457204 A1 * | 9/2004 | A61J 3/10 |
| JP | H09-104619 | 4/1997 | |
| JP | H09-143073 | 6/1997 | |
| JP | 2002-506418 | 2/2002 | |
| JP | 2005-501852 | 1/2005 | |
| JP | 2005-281231 | 10/2005 | |
| JP | 2006-111558 | 4/2006 | |
| JP | 2007-51093 | 3/2007 | |
| JP | 2007-525472 | 9/2007 | |
| JP | 2009-515993 | 4/2009 | |
| JP | 2012-500254 | 1/2012 | |
| JP | 2013-525294 | 6/2013 | |
| JP | 2018-504445 | 2/2018 | |
| JP | 2008-509933 | 8/2021 | |
| JP | 2021-128281 | 9/2021 | |
| WO | WO 00/48589 | 8/2000 | |
| WO | WO 00/50386 | 8/2000 | |
| WO | WO 00/59863 | 10/2000 | |
| WO | WO 01/32130 | 5/2001 | |
| WO | WO 01/32596 | 5/2001 | |
| WO | WO 01/34114 | 5/2001 | |
| WO | WO 03/015822 | 2/2003 | |
| WO | WO 03/045306 | 6/2003 | |
| WO | WO 03/045331 | 6/2003 | |
| WO | WO 2004/012772 | 2/2004 | |
| WO | WO 2005/002549 | 1/2005 | |
| WO | WO 2006/076692 | 7/2006 | |
| WO | WO 2006/084164 | 8/2006 | |
| WO | WO 2007/121318 | 10/2007 | |
| WO | WO 2007/121471 | 10/2007 | |
| WO | WO 2009/080764 | 7/2009 | |
| WO | WO 2010/020978 | 2/2010 | |
| WO | WO 2012/080471 | 6/2012 | |
| WO | WO 2013/067309 | 5/2013 | |
| WO | WO 2013/189988 | 12/2013 | |
| WO | WO 2016/128970 | 8/2016 | |
| WO | WO 2016/128971 | 8/2016 | |
| WO | WO 2016/128972 | 8/2016 | |
| WO | WO 2016/128973 | 8/2016 | |
| WO | WO 2016/128974 | 8/2016 | |
| WO | WO 2018/033927 | 2/2018 | |

OTHER PUBLICATIONS

Office Action Dated Dec. 24, 2019 From the Israel Patent Office Re. Application No. 253803 and Its Translation Into English. (6 Pages).
Official Action Dated Dec. 20, 2019 From the US Patent and Trademark Office Re. U.S. Appl. No. 15/549,418. (33 pages).
Cafesso "Intramuscular Injection", Retrieved from healthline.com, 3 Pages, 2013.
Cusano et al. "Parathyroid Hormone Therapy for Hypoparathyroidism", Best Practice & Research. Clinical Endocrinology & Metabolism, 29(1): 47-55, Published Online Sep. 10, 2014.
Cusano et al. "PTH(1-84) Replacement Therapy for the Treatment of Hypoparathyroidism", Expert Review of Endocrinology & Metabolism, 10(1): 5-13, Jan. 1, 2015.
Drugs.com "Drug Dosage", Retrieved from drugs.com, 2 Pages, 2010.
Karsdal et al. "Influence of Food Intake on the Bioavailability and Efficacy of Oral Calcitonin", British Journal of Clinical Pharmacology, BJCP, 67(4): 413-420, Apr. 2009.
Notification of Office Action and Search Report Dated Nov. 18, 2019 From the National Intellectual Property Administration of the People's Republic of China Re. Application No. 201680016126.5 and Its Translation Into English. (15 Pages).
Official Action Dated Jan. 28, 2020 From the US Patent and Trademark Office Re. U.S. Appl. No. 15/549,394. (34 pages).
Huang et al. "Effects of Tea Polyphenols on the Activities of Soybean Trypsin Inhibitors and Trypsin", Journal of the Science of Food and Agriculture, 84:121-126, 2004.
Official Action Dated Jul. 12, 2019 From the US Patent and Trademark Office Re. U.S. Appl. No. 15/549,425. (29 Pages).
Di Prospera "Understanding Oral Solid Dose Form (OSD) Manufacturing", Presentation at TechTank slides, 38 Pages, Mar. 18, 2014.
Sakai et al. "Species Differences in the Pharmacokinetic Parameters of Cytochrome P450 Probe Substrates between Experimental Animals, such as Mice, Rats, Dogs, Monkeys, and Microminipigs, and Humans", Journal of Drug Metabolism and Toxicology, 5(6): 1-12, 2014.
Notice of Allowance Dated Oct. 17, 2019 From the US Patent and Trademark Office Re. U.S. Appl. No. 15/549,436. (16 pages).
Notice of Reasons for Rejection Dated Oct. 15, 2019 From the Japan Patent Office Re. Application No. 2017-541780 and Its Translation Into English. (10 Pages).
Notice of Reasons for Rejection Dated Oct. 15, 2019 From the Japan Patent Office Re. Application No. 2017-541786 and Its Translation Into English. (10 Pages).
Galitzer et al. "Teriparatide Delivered Orally With Novel Drug Delivery Technology—First in Humans Results", ASMBR 2013 Annual Meeting, Journal of Bone and Mineral Research, 28(Suppl. 1): S68, # FR0378, Feb. 2013.
Supplementary European Search Report and the European Search Opinion Dated Jul. 17, 2019 From the European Patent Office Re. Application No. 16748835.2. (14 Pages).
Official Action Dated Jun. 28, 2019 From the US Patent and Trademark Office Re. U.S. Appl. No. 15/549,442. (28 Pages).
Applicant-Initiated Interview Summary Dated Jul. 29, 2019 From the US Patent and Trademark Office Re. U.S. Appl. No. 15/549,442. (4 pages).
Official Action Dated May 1, 2019 From the US Patent and Trademark Office Re. U.S. Appl. No. 15/549,436. (31 Pages).
Official Action Dated Apr. 22, 2020 from the US Patent and Trademark Office Re. U.S. Appl. No. 16/724,400. (30 pages).
Official Action Dated Apr. 7, 2020 from the US Patent and Trademark Office Re. U.S. Appl. No. 15/549,425. (27 pages).
Hammerle et al. "The Single Dose Pharmacokinetic Profile of a Novel Oral Human Parathroid Hormone Formulation in Healthy Postmenopausal Women", Bone 50: 965-973, 2012.
Hodsman et al. "Parathyroid Hormone and Teriparatide for the Treatment of Osteoporosis: A Review of the Evidence and Suggested Guidelines for Its Use", Endocrine Reviews 26(5): 688-703, Mar. 15, 2005.
Search Report and Written Opinion Dated Jan. 30, 2020 From the Intellectual Property Office of Singapore, IPOS Re. Application No. 11201901070Y. (10 Pages).
Supplementary European Search Report and the European Search Opinion Dated Feb. 7, 2020 From the European Patent Office Re. Application No. 17841226.8.
Choonara et al. "A Review of Advanced Oral Drug Delivery Technologies Facilitating the Protection and Adsorption of Protein

(56) References Cited

OTHER PUBLICATIONS and Peptide Molecules", Biotechnology Advances, 32(7): 1269-1282, Available Online Aug. 3, 2014.
Kapitza et al. "Oral Insulin: A Comparison With Subcutaneous Regular Human Insulin in Patients With Type 2 Diabetes", Diabetes Care, 33(6): 1288-1290, Published Online Feb. 25, 2010.
Final Official Action Dated May 1, 2020 from the US Patent and Trademark Office Re. U.S. Appl. No. 15/549,442. (27 pages).
Welling "Effects of Food on Drug Absorption", Annual Review Nutrition, 16: 383-415, 1996.
Advisory Action Before the Filing of An Appeal Brief Dated Aug. 10, 2018 From the US Patent and Trademark Office Re. U.S. Appl. No. 15/549,436. (4 pages).
Applicant-Initiated Interview Summary Dated Jan. 14, 2019 From the US Patent and Trademark Office Re. U.S. Appl. No. 15/549,436. (3 pages).
International Preliminary Report on Patentability Dated Aug. 24, 2017 From the International Bureau of WIPO Re. Application No. PCT/2016/050153. (8 Pages).
International Preliminary Report on Patentability Dated Aug. 24, 2017 From the International Bureau of WIPO Re. Application No. PCT/2016/050154. (9 Pages).
International Preliminary Report on Patentability Dated Feb. 28, 2019 From the International Bureau of WIPO Re. Application No. PCT/IL2017/050920. (11 Pages).
International Search Report and the Written Opinion Dated May 19, 2016 From the International Searching Authority Re. Application No. PCT/IL2016/050155.
International Search Report and the Written Opinion Dated May 22, 2016 From the International Searching Authority Re. Application No. PCT/IL2016/050153.
International Search Report and the Written Opinion Dated May 23, 2016 From the International Searching Authority Re. Application No. PCT/IL2016/050151.
International Search Report and the Written Opinion Dated May 24, 2016 From the International Searching Authority Re. Application No. PCT/IL2016/050152.
International Search Report and the Written Opinion Dated May 24, 2016 From the International Searching Authority Re. Application No. PCT/IL2016/050154.
International Search Report and the Written Opinion Dated Nov. 28, 2017 From the International Searching Authority Re. Application No. PCT/IL2017/050920.
Official Action Dated Jan. 3, 2019 From the US Patent and Trademark Office Re. U.S. Appl. No. 15/549,425. (47 pages).
Official Action Dated Nov. 5, 2018 From the US Patent and Trademark Office Re. U.S. Appl. No. 15/549,436. (16 pages).
Official Action Dated Feb. 8, 2019 From the US Patent and Trademark Office Re. U.S. Appl. No. 15/549,394. (34 pages).
Official Action Dated Aug. 10, 2018 From the US Patent and Trademark Office Re. U.S. Appl. No. 15/549,394. (35 pages).
Official Action Dated Jan. 14, 2019 From the US Patent and Trademark Office Re. U.S. Appl. No. 15/549,442. (45 pages).
Official Action Dated Sep. 21, 2018 From the US Patent and Trademark Office Re. U.S. Appl. No. 15/549,418. (36 Pages).
Official Action Dated Nov. 22, 2017 From the US Patent and Trademark Office Re. U.S. Appl. No. 15/549,436. (20 pages).
Official Action Dated May 24, 2018 From the US Patent and Trademark Office Re. U.S. Appl. No. 15/549,436. (27 pages).
Official Action Dated Jan. 28, 2019 From the US Patent and Trademark Office Re. U.S. Appl. No. 15/549,418. (26 pages).
Restriction Official Action Dated Apr. 6, 2018 From the US Patent and Trademark Office Re. U.S. Appl. No. 15/549,418. (5 pages).
Restriction Official Action Dated Apr. 9, 2018 From the US Patent and Trademark Office Re. U.S. Appl. No. 15/549,394. (7 pages).
Supplementary European Search Report and the European Search Opinion Dated Oct. 11, 2018 From the European Patent Office Re. Application No. 16748831.1. (9 Pages).
Supplementary European Search Report and the European Search Opinion Dated Oct. 11, 2018 From the European Patent Office Re. Application No. 16748832.9. (9 Pages).
Supplementary European Search Report and the European Search Opinion Dated Oct. 18, 2018 From the European Patent Office Re. Application No. 16748833.7. (7 Pages).
Supplementary European Search Report and the European Search Opinion Dated Oct. 18, 2018 From the European Patent Office Re. Application No. 16748834.5. (9 Pages).
Supplementary Partial European Search Report and the European Search Opinion Dated Oct. 18, 2018 From the European Patent Office Re. Application No. 16748835.2. (12 Pages).
Abbas et al. "Clinical Pharmokokinetic and Pharmacodynamic Interaction Studies to Evaluate Effects of Antacid (Cimetidine and Maalox) Pretreatment on the Absorption of Heparin and its Delivery Agent, SNAC, Following Oral Administration in Healthy Subjects", Blood American Society of Hematology, XP009508315, 98(11/Pt.2): 86b, # 3975, Nov. 16, 2001.
Aggarwal et al. "Parathyroid Hormone and Its Effects on Dental Tissues", Oral Diseases, 18(1): 48-54, Published Online Sep. 6, 2011.
Aspenberg "Parathyroid Hormone and Fracture Healing", Acta Orthopaedica, 84(1): 4-6, 2013.
Bashutski et al. "Teriparatide and Osseous Regeneration in the Oral Cavity", The New England Journal of Medicine, 363(25): 2397-2405, Dec. 16, 2010.
Bastian et al. "Systemic Inflammation and Fracture Healing", Journal of Leukocyte Biology, 89(5): 669-673, May 2011.
Baumgarten et al. "Pressure Ulcers in Elderly Hip Fracture Patients Across the Continuum of Care", Journal of American Geriatrics Society, 57(5): 863-870, May 2009.
Berkowitz et al. "Oral Heparin Administration with a Novel Drug Delivery Agent (SNAC) in Healthy Volunteers and Patients Undergoing Elective Total Hip Arthroplasty", Journal of Thrombosis and Haemostasis, 1: 1914-1919, Mar. 5, 2003.
Bilezikian et al. "Hypoparathyroidism in the Adult: Epidemiology, Diagnosis, Pathophysiology, Target Organ Involvement, Treatment, and Challenges for Future Research", Journal of Bone and Mineral Research, 26(10): 2317-2337, Oct. 2011.
Brixen et al. "Teriparatide (Biosynthetic Human Parathyroid Hormone 1-34): A New Paradigm m the Treatment of Osteoporosis", Basic & Clinical Pharmacology & Toxicology 94(6): 260-270, Jun. 2004.
Bukata et al. "Orthopedic Uses of Teriparatide", Current Osteoporos Reports, 8(1): 28-33, Mar. 2010.
Cusano et al. "Use of Parathyroid Hormone in Hypoparathyroidism", Journal of Endocrinological Investigation, 36(11): 1121-1127, Dec. 2013.
De Vos "Clinical Pharmacokinetics of Slow Release Mesalazine", Clinical Pharmacokinetics, 39(2): 85-97, Aug. 2000.
Della Rocca et al. "Parathyroid Hormone: Is There a Role in Fracture Healing?", Journal of Orthopaedic Trauma, 24(3): S31-S35, Mar. 2010, 5 pages.
Engel et al. "An Innovative Smart Oral Delivery Technology for Proteins and Peptides", ONdrug Delivery, 69: 8-11, Jul. 25, 2016. p. 9, Ledt and Mid cols. p. 10, Left col. Third Para, Left and Mid cols. Fig.3.
Everyday Health "Teriparatide", The Everyday Health Web Page, Retrieved from everydayhealth.com, 5 Pages, Available Online 2010.—updated on Jun. 15, 2018.
Fallat et al. "Perfomring Surgery on Smokers: What You Should Know", Podiatry Today, 26(4): 30-38, Published Online Mar. 25, 2013.
Gafni et al. "Daily Parathyroid Hormone 1-34 Replacement Therapy for Hypoparathyroidism Induces Changes in Bone Turnover and Structure", Journal of Bone and Mineral Research, 27(8): 1811-1820, Aug. 2012.
Giannotti et al. "Current Medical Treatment Strategies Concerning Fracture Healing", Clinical Cases in Mineral and Bone Metabolism, 10(2): 116-120, 2013.
Grover et al. "Teriparatide: A Novel Means to Ultimately Achieve True Regeneration!!!", Journal of Clinical and Diagnostic Research, 7(8): 1820-1823, Aug. 2013.

(56) References Cited

OTHER PUBLICATIONS

Koide et al. "The Amino Acid Sequence of Soybean Trypsin Inhibitor (Kunitz)", The Journal of Biochemistry, 71(1): 165-167, Jan. 25, 1972.
Le Tourneau et al. "Dose Escalation Methods in Phase I Cancer Clinical Trials", JNCI: Journal of the National Cancer Institute, 101(10): 708-720, May 2009.
Maher et al. "Overcoming Poor Permeability: Translating Permeation Enhancers for Oral Peptide Delivery", Drug Discovery Today: Technologies, 9(1): e1131-e119, Aug. 31, 2012. p. e114, Right col., Para 2-3.
Malhotra et al. "Tensile Type of Stress Fracture Neck of Femur: Role of Teriparatide in the Process of Healing in a High Risk Patient for Impaired Healing of Fracture", Clinical Cases in Mineral and Bone Metabolism, 10(3): 210-212, 2013.
Marine-Mammal "Blue Whale", retrieved from marinemammalcenter. org, 2 Pages, Jan. 10, 2018.
Martin "Bone Biology and Anabolic Therapies for Bone: Current Status and Future Prospects", Journal of Bone Metabolism, 21(1): 8-20, Epub Feb. 28, 2014.
MGI "Mouse Facts", Retrieved from informatics.jax.org, 2 Pages, Jan. 10, 2018.
Mitani "Effective Treatment of a Steroid-Induced Femoral Neck Fracture Nonunion With a Once-Weekly Administration of Teriparatide in a Rheumatoid Patient: a Case Report", Archives of Osteoporosis, 8(1-2): 131, Epub Mar. 29, 2013.
Moon et al. "Parathyroid Hormone 1-34(Teriparatide) Treatment in Pelvic Insufficiency Fractures. A Report of Two Cases", Journal of Bone Metabolism, 19(2): 147-151, 2012.
Peichl et al. "Parathyroid Hormone 1-84 Accelerates Fracture-Healing in Pubic Bones of Elderly Osteoporotic Women", the Journal of Bone & Joint Surgery, 93(17): 1583-1587, Sep. 7, 2011.
Pharma Tips "Multiple Unit Tablets", Pharma Tips, Pharmaceutics, 5 P., Jan. 16, 2011.
Puig-Domingo et al. "Successful Treatment of Vitamin D Unresponsive Hypoparathyroidism With Multipulse Subcutaneous Infusion of Teriparatide", European Journal of Endocrinology, 159: 653-657, 2008.
Qi et al. "Effect of Casein and Protamine on the Enzymatic Degradation and the Orally Hypoglycemic Action of Insulin", Acta Pharmaceutica Sinica, 39(10): 844-848, 2004. English Abstract.
Qi et al. "Gastrointestinal Absorption Enhancement of Insulin by Administration of Enteric Microspheres and SNAC to Rats", Journal of Microencapsulation, 21(1): 37-45, Feb. 2004.
Riek et al. "The Pharmacological Management of Osteoporosis", Missouri Medicine, 108(2): 118-123, Mar.-Apr. 2011.
Roche "The Complete Guide for Protease Inhibition", Roche Applied Science, 16 Pages, 2004.
Rubin et al. "Therapy of Hypoparathyroidism With Intact Parathyroid Hormone", Osteoporosis International, 21(11): 1927-1934, Nov. 2010.
Sani et al. "Oral Protein-Drug Delivery Systems Suitable for Systemic Circulation", International Journal of Modern Biology and Medicine, 5(1): 5-16, Published Feb. 28, 2014.
Setchell et al. "Pharmacokinetics of A Slow-Release Formulation of Soybean Isoflavones in Healthy Postmenopausal Women", Journal of Agricultural and Food Chemistry, 53(6): 1938-1944, Published on Web Feb. 18, 2005.
Shah et al. "Regulating Drug Release Behavior and Kinetics From Matrix Tablets Based on Fine Particle-Sized Ethyl Cellulose Ether Derivatives: An In Vitro and In Vivo Evaluation", The Scientific World Journal, 2012(Art.ID 842348): 1-8, Published Online Apr. 29, 2012.
Shailesh et al. "Preparation and In Vitro Evaluation of Ethylcellulose Coated Egg Albumin Microspheres of Diltiazem Hydrochloride", Journal of Young Pharmacists, JYP, 2(1): 27-34, Jan. 2010.
Sheyn et al. "PTH Promotes Allograft Integration in A Calvarial Bone Defect", Molecular Pharmaceutics, 10(12): 4462-4471, Dec. 2, 2013.
Spags "A Girl's Awkward Twerking on the Side of Road Distracted a Driver and Made for a Nasty Motorcycle Crash", Barstool Sports, Published Online on Apr. 17, 2017.
Suzman et al. "Bone-targeting Agents in Prostrate Cancer", Cancer and Metastasis Reviews, 33(0): 619-628, Sep. 2014.
Swihart et al. "Relating Body Size to the Rate of Home Range Use in Mammals", Ecology, 69(2): 393-399, Apr. 1988.
Werle et al. "Chitosan-Aprotinin Coated Liposomes for Oral Peptide Delivery: Development, Characterisation and In Vivo Evaluation", International Journal of Pharmaceutics, 370(1): 26-32, Mar. 31, 2009. Abstract.
Werle et al. "Oral Protein Delivery: A Patent Review of Academic and Industrial Approaches", Recent Patents on Drug Delivery & Formulation, 3(2): 94-104, Jun. 1, 2009. p. 99, Right col. 2nd Para—p. 100, Left col.
Winer et al. "Effects of Once Versus Twice-Daily Parathyroid Hormone 1-34 Therapy in Children With Hypoparathyroidism", Journal of Clinical Endocrinology and Metabolism, 93(9): 3389-3395, Published Online May 20, 2008.
Winer et al. "Long-Term Treatment of Hypoparathyroidism: A Randomized Controlled Study Comparing Parathyroid Hormone-(1-34) Versus Calcitriol and Calcium", The Journal of Clinical Endocrinology & Metabolism, 88(9): 4214-4220, 2003.
Winer et al. "Synthetic Human Parathyroid Hormone 1-34 Replacement Therapy: A Randomized Crossover Trial Comparing Pump Versus Injections in the Treatment of Chronic Hypoparathyroidism", Journal of Clinical Endocrinology and Metabolism, 97(2): 391-399, Published Online Nov. 16, 2011.
Examination Report Dated Sep. 25, 2020 From the Servico Publico Federal Minitsterio Da Economia Insttuto Nacional Da Propriedace Industrial of Brazil RE Application No. BR112017017112.0 and Its English Translation. (4 Pages).
Notification of Office Action and Search Report Dated Sep. 24, 2020 From the State Intellectual Property Office of the People's Republic of China Re. Application No. 201680016126.5. (5 Pges).
Galitzer et al. "Teriparatide Delivered Orally with Novel Drug Delivery Technology—First in Humans Results, Annual Meeting of the American Society for Bone and Mineral Research", Abstract, 2013.
Notice of Reasons for Rejection Dated Oct. 6, 2020 From the Japan Patent Office Re. Application No. 2017-541780 and Its Translation Into English. (12 Pages).
Notice of Reasons for Rejection Dated Oct. 6, 2020 From the Japan Patent Office Re. Application No. 2017-541786 and Its Translation Into English. (14 Pages).
Translation Dated Oct. 19, 2020 of Notification of Office Action Dated Sep. 24, 2020 From The State Intellectual Property Office of the People's Republic of China Re. Application No. 201680016126. 5. (5 Pages).
Sturmer et al. "Pharmacokinetics of Oral Recombinant Human Parathyroid Hormone [RhPTH(1-31)NH2] in Postmenopausal Women With Osteoporosis", Clinical Pharmacokinetics, 52(11): 995-1004, Published Online May 30, 2013.
Final Official Action Dated Oct. 29, 2020 From the US Patent and Trademark Office Re. U.S. Appl. No. 15/549,425. (28 pages).
ClinicalTrials.gov "Bioavailability Study of 3 Tablet Formulations vs. Capsule Formulation of JNJ-56021927 in Fasting Healthy Male Participants," ClinicalTrials.gov Identifier: NCT02160756, Last Update Posted on Oct. 20, 2016, 9 pages.
Cole et al "Evaluating Development and Production Costs: Tablets Versus Capsules," Pharmaceuatical Technology Europe 5: 17-26, 1998.
Final Official Action Dated Jun. 29, 2020 from the US Patent and Trademark Office Re. U.S. Appl. No. 15/549,418. (32 pages).
Interview Summary Dated Jun. 17, 2020 from the US Patent and Trademark Office Re. U.S. Appl. No. 15/549,442. (4 pages).
Bigal et al. "The Triptan Formulations", Arq Neuropsiquiatr 61 (2-A): 313-320, 2003.
Office Action Dated Dec. 17, 2020 From the Israel Patent Office Re. Application No. 253802 and Its Translation Into English. (8 Pages).
Final Official Action Dated Sep. 16, 2020 from the US Patent and Trademark Office Re. U.S. Appl. No. 16/724,400. (14 pages).

(56) References Cited

OTHER PUBLICATIONS

Final Official Action Dated Sep. 4, 2020 from the US Patent and Trademark Office Re. U.S. Appl. No. 15/549,394. (33 pages).
Official Action Dated Jun. 28, 2021 form the US Patent and Trademark Office Re. U.S. Appl. No. 16/724,400. (28 pages).
Communication Pursuant to Article 94(3) EPC Dated Dec. 8, 2020 From the European Patent Office Re. Application No. 17841226.8. (5 Pages).
Communication Pursuant to Article 94(3) EPC Dated Mar. 31, 2021 From the European Patent Office Re. Application No. 16748832.9. (10 Pages).
Leone-Bay et al. "Oral Delivery of Biologically Active Parathyroid Hormone", Pharmaceutical Research,18 (7):964-970, XP1106035A, Jul. 2001.
Patent Examination Report Dated Jul. 27, 2021 From the New Zealand Intellectual Property Office Re Application No. 751668. (13 Pages).
Communication Pursuant to Article 94(3) EPC Dated Apr. 15, 2021 From the European Patent Office Re. Application No. 16748833.7. (7 Pages).
Communication Pursuant to Article 94(3) EPC Dated Apr. 20, 2021 From the European Patent Office Re. Application No. 16748831.1. (6 Pages).
Communication Pursuant to Article 94(3) EPC Dated Apr. 22, 2021 From the European Patent Office Re. Application No. 16748834.5. (7 Pages).
Final Official Action Dated Jun. 11, 2021 From the US Patent and Trademark Office Re. U.S. Appl. No. 15/549,394. (24 Pages).
Final Official Action Dated Apr. 2, 2021 from the US Patent and Trademark Office Re. U.S. Appl. No. 15/549,418. (26 pages).
Interview Summary Dated Apr. 2, 2021 From the US Patent and Trademark Office Re. U.S. Appl. No. 15/549,442. (3 Pages).
Invitation to Pay Additional Fees, Communication Relating to the Results of the Partial International Search and the Provisional Opinion Dated Mar. 19, 2019 From the International Searching Authority PCT/IB2018/059569. (20 Pages).
Notice of Reason(s) for Rejection Dated Jun. 8, 2021 From the Japan Patent Office Re. Application No. 2019-508963 and Its Translation Into English. (8 Pages).
Notification of Office Action and Search Report Dated Apr. 16, 2021 From the State Intellectual Property Office of the People's Republic of China Re. Application No. 201680016126.5 and Its Translation of Office Action Into English. (14 Pages).
Official Action Dated May 27, 2021 from the US Patent and Trademark Office Re. U.S. Appl. No. 15/549,425. (25 pages).
Attili-Quadri et al. "Oral Delivery System Prolongs Blood Circulation of Docetaxel Nanocapsules via Lymphatic Absoption", PNAS, 110(43): 17498-17503, 2013.
Greenbalt et al. "Absorption of Oral and Intramuscular Chlordiazepoxide", European Journal of Clinical Pharmacology, 13: 267-274, 1978.
Leone-Bay et al. "Oral Delivery of Biologically Active Parathyroid Hormone", Pharmaceutical Research, XP001106035, 18(7): 964-970, Jul. 1, 2001.
McLachlan et al. "Meals and Medicines", Australian Prescriber., 29: 40-42, 2006.
Richter et al. "Subcutaneous Absorption of Biotherapeutics: Known and Unknown", Drug Metabolism and Disposition, 42:1881-1889, 2014.
Teja-Isavadharm et al. "Comparative Bioavailability of Oral, Rectal, and Intramuscular Arthemether in Healthy Subjects: Use of Simultaneous Measurements by High Performance Liquid Chromatography and Bioassay"; British Journal of Clinical Pharmacology, 42: 599-604, 1996.
Nagendrakumar et al. "An Overview: Matrix Tablets as Sustained Release", Recent Research in Science and Technology, 5(4): 36-45, Jan. 14, 214.
Examination Report Under Sections 12 & 13 of the Patents Act, 1970 and the Patents Rules, 2003 Dated Aug. 9, 2021 From the Government of India, Intellectual Property India, Patents, Designs, Trade Marks, Geographical Indications, The Patent Office Re. Application No. 201947010044. (6 Pages).
Communication Pursuant to Article 94(3) EPC Dated Oct. 20, 2021 From the European Patent Office Re. Application No. 17841226.8. (5 Pages).
Final Official Action Dated Feb. 4, 2021 From the US Patent and Trademark Office Re. U.S. Appl. No. 15/549,442. (26 Pages).
Office Action Dated Mar. 4, 2021 From the Israel Patent Office Re. Application No. 264880 and Its Translation Into English. (7 Pages).
Office Action Dated Dec. 24, 2020 From the Israel Patent Office Re. Application No. 253804 and Its Translation Into English. (9 Pages).
Search Report and Written Opinion Dated Dec. 17, 2020 From the Intellectual Property Office of Singapore, IPOS Re. Application No. 11201901070Y. (8 Pages).
"Chemistry 104: Analysis of Commercial Antacid Tablets", 2 P., ttps://web.archive.org/web/200108082 1 3030/http://www.chem.latech.edu:80/~deddy /chem104/104Antacid.htm, Aug. 8, 2001.
Final Official Action Dated Feb. 17, 2022 from US Patent and Trademark Office Re. U.S. Appl. No. 16/724,400. (33 pages).
Final Official Action Dated Feb. 3, 2022 from US Patent and Trademark Office Re. U.S. Appl. No. 15/549,418. (32 pages).
Requisition by the Examiner Dated Dec. 20, 2021 From the Innovation, Science and Economic Development Canada, Canadian Intellectual Property Office Re. Application No. 3,011,654. (9Pages).
Office Action Dated Feb. 6, 2022 From the Israel Patent Office Re. Application No. 264880 and Its Translation Into English. (6 Pages).
Requisition by the Examiner Dated Feb. 4, 2022 From the Innovation, Science and Economic Development Canada, Canadian Intellectual Property Office Re. Application No. 2,975,578. (6 Pages).
Examination Report Dated Nov. 17, 2021 From the Instituto Mexicano de la Propiedad Industrial, Direccion Divisional de Patentes Re. Application No. MX/a/2017010220 and Its Translation Into English. (13 Pages).
Final Official Action Dated Jan. 24, 2022 from US Patent and Trademark Office Re. U.S. Appl. No. 15/549,425. (33 pages).
Requisition by the Examiner Dated Jan. 10, 2022 From the Innovation, Science and Economic Development Canada, Canadian Intellectual Property Office Re. Application No. 3,011,657. (11 Pages).
Office Action Dated Dec. 14, 2021 From the Israel Patent Office Re. Application No. 283258 and Its Translation Into English. (7 Pages).
English Translation Dated Apr. 19, 2022 of Ground(s) of Reason of Rejection Dated Mar. 28, 2022 From the Korean Intellectual Property Office Re. Application No. 10-2019-7007250. (6 pages).
Examination Report Dated Feb. 9, 2022 From the Intellectual Property Office of Singapore, IPOS Re. Application No. 11201901070Y. (8 Pages).
Final Official Action Dated Apr. 1, 2022 from US Patent and Trademark Office Re. U.S. Appl. No. 15/549,394. (40 pages).
Ground(s) of Reason of Rejection Dated Mar. 28, 2022 From the Korean Intellectual Property Office Re. Application No. 10-2019-7007250. (9 pages).
Notice of Decision of Rejection Dated Feb. 22, 2022 From the Japan Patent Office Re. Application No. 2019-508963 and Its Translation Into English. (9 Pages).
Patent Examination Report Dated Feb. 16, 2022 From the New Zealand Intellectual Property Office Re Application No. 751668. (7 Pages).
Requisition by the Examiner Dated Mar. 18, 2022 From the Innovation, Science and Economic Development Canada, Canadian Intellectual Property Office Re. Application No. 2,975,710 and Claims. (8 Pages).
Requisition by the Examiner Dated Mar. 25, 2022 From the Innovation, Science and Economic Development Canada, Canadian Intellectual Property Office Re. Application No. 2,975,676 with Claims. (8 Pages).
Khada et al. "Pharmaceutical Particle Technologies: An Approach to Improve Drug Solubility, Dissolution and Bioavailability", Asian Journal of Pharmaceutical Sciences, 9(6): 304-316, Dec. 2014.
Maghsoodi "Role of Solvents in Improvement of Dissolution Rate of Drugs: Crystal Habit and Crystal Agglomeration", Advanced Pharmaceutical Bulletin, 5(1): 13-18, Mar. 5, 2022.

(56) References Cited

OTHER PUBLICATIONS

Sandberg et al. "Steady-State Bioavailability and Day-to-Day Variability of a Multiple-Unit (CR/ZOK) and a Single-Unit (OROS) Delivery System of Metoprolol After Once-Daily Dosing", Pharmaceutical Research, 10(1): 28-34, Jan. 1993.
Communication Pursuant to Article 94(3) EPC Dated May 23, 2022 From the European Patent Office Re. Application No. 16748835.2. (6 Pages).
Examination Report Dated Jul. 5, 2022 From the Instituto Mexicano de la Propiedad Industrial, Direccion Divisional de Patentes Re. Application No. MX/a/2017/010220 and Its Translation Into English. (8 Pages).
Final Official Action Dated Aug. 29, 2022 from US Patent and Trademark Office Re. U.S. Appl. No. 16/724,400. (23 pages).
Hearing Notice Dated May 24, 2022 From the Government of India, Intellectual Property India, Patent Office, Intellectual Property Building Re. Application No. 201947010044. (2 Pages).
Notice of Reason(s) for Rejection Dated Sep. 6, 2022 From the Japan Patent Office Re. Application No. 2021-128281 and Its Translation Into English. (14 Pages).
Notice of Reasons for Rejection Dated May 31, 2022 From the Japan Patent Office Re. Application No. 2021-128296 and its Translation into English. (9 Pages).
Notification of Decision of Rejection Dated Feb. 16, 2022 From the China National Intellectual Property Administration Re. Application No. 201680016126.5 and Its Translation Into English. (9 Pages).
Notification of Office Action and Search Report Dated Feb. 11, 2022 From the State Intellectual Property Office of the People's Republic of China Re. Application No. 202111014609.0 and Its Translation of Office Action Into English. (15 Pages).
Notification of Office Action and Search Report Dated Jan. 18, 2022 From the State Intellectual Property Office of the People's Republic of China Re. Application No. 202111014352.9 and Its Translation of Office Action Into English. (15 Pages).
Notification of Office Action and Search Report Dated Jan. 24, 2022 From the State Intellectual Property Office of the People's Republic of China Re. Application No. 201780064008.6 with English Translation of Office Action and Claims. (24 Pages).
Official Action Dated Apr. 28, 2022 from US Patent and Trademark Office Re. U.S. Appl. No. 15/549,442. (46 pages).
Pre-Appeal Examination Report Dated Aug. 10, 2022 From the Japan Patent Office Re. Application No. 2019-508963 and Its Translation Into English. (9 Pages).
Castelli et al. "Pharmacokinetics of Oral Cyanocobalamin Formulated With Sodium N-[8-(2-Hydroxybenzoyl)Amino] Caprylate (SNAC:): An Open-Label, Randomized, Single-Dose, Parallel-Group Study in Healthy Male Subjects", Clinical Therapeutics, 33(7): 934-945, Jul. 2011.
Ciampolini et al. "Training to Estimate Blood Glucose and to Form Associations with Initial Hunger", Nutrition & Metabolism, 42: 1-11, Dec. 8, 2006.
Lopes et al. "Overview on Gastroretentive Drug Delivery Systems for Improving Drug Bioavailability", International Journal of Pharmaceutics, 510(1): 144-158, Available Online May 9, 2016.
Sun "Effect of Tablet Compression on the Dissolution of Aspirintablets Using a Novel Off-Center Paddle Impeller (OPI) Dissolution Testing System", Master's Thesis, New Jersey Institute of Technology, Department of Biological and Pharmaceutical Engineering, 2013.
Wang et al. "Sustained and Controlled-Release Pellets ", Physical Pharmacy: 353-354, Jul. 31, 2010, Chinese only.
Communication Pursuant to Article 94(3) EPC Dated Nov. 14, 2022 From the European Patent Office Re. Application No. 17841226.8. (5 Pages).
Office Action Dated Feb. 19, 2023 From the Israel Patent Office Re. Application No. 264880 and Its Translation Into English. (5 Pages).
Technical Examination Report Dated Feb. 23, 2023 from the National Institute of Industrial Property of Brazil Re. Application No. BR 11 2017 017112 0 and Its Summary Into English. (9 Pages).
Requisition by the Examiner Dated Mar. 22, 2023 From the Innovation, Science and Economic Development Canada, Canadian Intellectual Property Office Re. Application No. 2,975,578. (4 pages).
Technical Examination Report Dated Feb. 23, 2023 from the National Institute of Industrial Property of Brazil Re. Application No. BR 11 2017 017112 0 and Its Summary Into English. (7 Pages).
Requisition by the Examiner Dated Feb. 8, 2023 From the Innovation, Science and Economic Development Canada, Canadian Intellectual Property Office Re. Application No. 3,011,657. (3 Pages).
Advisory Action together with Interview Summary Dated Mar. 1, 2023 From the US Patent and Trademark Office Re. U.S. Appl. No. 15/549,425. (9 Pages).
Notification of Office Action Dated Oct. 14, 2022 From the State Intellectual Property Office of the People's Republic of China Re. Application No. 202111014609.0 and Its Translation of Office Action Into English and Claims. (12 Pages).
Requisition by the Examiner Dated Oct. 18, 2022 From the Innovation, Science and Economic Development Canada, Canadian Intellectual Property Office Re. Application No. 2,975,710 and Claims. (7 Pages).
Interview Summary Dated Oct. 18, 2022 From the US Patent and Trademark Office Re. U.S. Appl. No. 16/724,400. (2 Pages).
Advisory Action Dated Dec. 13, 2022 from the US Patent and Trademark Office Re. U.S. Appl. No. 16/724,400. (3 pages).
Final Official Action Dated Dec. 9, 2022 from the US Patent and Trademark Office Re. U.S. Appl. No. 15/549,394. (29 pages).
Final Official Action Dated Dec. 9, 2022 from the US Patent and Trademark Office Re. U.S. Appl. No. 15/549,418. (36 pages).
Final Official Action Dated Nov. 14, 2022 from the US Patent and Trademark Office Re. U.S. Appl. No. 15/549,425. (32 pages).
Office Action Dated Nov. 13, 2022 From the Israel Patent Office Re. Application No. 292218. (5 Pages).
Final Notice of Rejection Dated Jan. 13, 2023 From the Korean Intellectual Property Office Re. Application No. 10-2019-7007250 and Claims. (10 pages).
Notification of Office Action and Search Report Dated Jan. 20, 2023 From the State Intellectual Property Office of the People's Republic of China Re. Application No. 201780064008.6 and Its Translation Into English. (16 Pages).
Office Action Dated Jan. 31, 2023 From the Israel Patent Office Re. Application No. 292417. (4 Pages).
Requisition by the Examiner Dated Jan. 31, 2023 From the Innovation, Science and Economic Development Canada, Canadian Intellectual Property Office Re. Application No. 2,975,676. (4 Pages).
Requisition by the Examiner Dated Jan. 31, 2023 From the Innovation, Science and Economic Development Canada, Canadian Intellectual Property Office Re. Application No. 3,011,654. (4 Pages).
Translation Dated Feb. 8, 2023 of Final Notice of Rejection Dated Jan. 13, 2023 From the Korean Intellectual Property Office Re. Application No. 10-2019-7007250. (4 Pages).
Examination Report Dated Mar. 1, 2023 From the Instituto Mexicano de la Propiedad Industrial, Direccion Divisional de Patentes Re. Application No. MX/a/2017/010220 and Its Translation Into English. (12 Pages).
Notice of Reason(s) for Rejection Dated Jan. 10, 2023 From the Japan Patent Office Re. Application No. 2021-128296 and Its Translation Into English. (10 Pages).
Final Official Action Dated Nov. 28, 2022 from the US Patent and Trademark Office Re. U.S. Appl. No. 15/549,442. (38 pages).
Decision on Rejection Dated Apr. 26, 2023 From the State Intellectual Property Office of the People's Republic of China Re. Application No. 201780064008.6. (10 pages).
Notice of Reason(s) for Rejection Dated May 23, 2023 From the Japan Patent Office Re. Application No. 2022-099609 and Its Translation Into English. (9 Pages).
Machine Translation Dated Feb. 5 of Final Notice of Rejection Dated Jan. 15, 2024 From the Korean Intellectual Property Office Re. Application No. 10-2023-7019713. (6 Pages).
Examination Report Dated Jan. 9, 2024 From the Instituto Mexicano de la Propiedad Industrial, Secretaria de Economia, Direccion

(56) References Cited

OTHER PUBLICATIONS

Divisional de Patentes Re. Application No. MX/a/2019/0018580 and Its Translation Into English. (10 Pages).
Notice of Reason(s) for Rejection Dated Jan. 9, 2024 From the Japan Patent Office Re. Application No. 2023-015960 and Its Translation Into English. (14 Pages).
Notice of Reason(s) for Rejection Dated Nov. 21, 2023 From the Japan Patent Office Re. Application No. 2022-099609 and Its Translation Into English. (11 Pages).
Official Action Dated Nov. 28, 2023 from the US Patent and Trademark Office Re. U.S. Appl. No. 16/724,400. (36 pages).
Relatório de Exame Tecnico Dated Aug. 22, 2023 From the Serviço Público Federal, Ministério da Economia, Instituto Nacional da Propriedade Industrial do Brasil Re. Application No. BR 12 2023 011064 1 and Its Summary Into English. (7 Pages).
Official Action Dated Mar. 14, 2024 from US Patent and Trademark Office Re. U.S. Appl. No. 15/549,394. (41 pages).
Official Action Dated Mar. 14, 2024 from US Patent and Trademark Office Re. U.S. Appl. No. 15/549,418. (45 pages).
Gupta et al. "Oral Delivery of Therapeutic Proteins and Peptides: a Review on Recent Developments", Drug Delivery 20(6): 237-246, Jul. 20, 2013.
ICH Harmonised Tripartite Guideline "Dose-response information to support drug registration", International Conference on IIarmonisation of Technical Requirements for Registration of Pharmaceuticals for Human Use, ICH-E4, Nov. 1994.
Interview Summary Dated Mar. 25, 2024 from the US Patent and Trademark Office Re. U.S. Appl. No. 16/724,400. (2 pages).
Communication Pursuant to Article 94(3) EPC Dated Jan. 18, 2024 From the European Patent Office Re. Application No. 17841226.8 (4 Pages).
Final Notice of Rejection Dated Jan. 15, 2024 From the Korean Intellectual Property Office Re. Application No. 10-2023-7019713. (7 Pages).
Communication Pursuant to Article 94(3) EPC Dated Mar. 18, 2024 From the European Patent Office Re. Application No. 16748831.1 (4 Pages).
Communication Pursuant to Article 94(3) EPC Dated Mar. 21, 2024 From the European Patent Office Re. Application No. 16748833.7 (8 Pages).
Official Action Dated Mar. 14, 2024 from the US Patent and Trademark Office Re. U.S. Appl. No. 15/549,425. (46 pages).
Decision on Rejection Dated Jul. 14, 2023 From the State Intellectual Property Office of the People's Republic of China Re. Application No. 202111014609.0 and Its Translation Into English. (10 Pages).
Examination Report Dated Jun. 28, 2023 From the Intellectual Property Office of Singapore, IPOS Re. Application No. 11201901070Y. (12 Pages).
Final Notice of Rejection Dated Jun. 27, 2023 From the Korean Intellectual Property Office Re. Application No. 10-2019-7007250. (7 Pages).
Grounds of Reason of Rejection Dated Aug. 17, 2023 From the Korean Intellectual Property Office Rc. Application No. 10-2023-7019713 and Its Machine Translation Into English. (19 Pages).
Notice of Reason(s) for Rejection Dated Aug. 8, 2023 From the Japan Patent Office Re. Application No. 2019-508963 and Its Translation Into English. (32 Pages).
Official Action Dated Aug. 4, 2023 from the US Patent and Trademark Office Re. U.S. Appl. No. 15/549,394. (23 pages).
Official Action Dated Aug. 4, 2023 from the US Patent and Trademark Office Re. U.S. Appl. No. 15/549,418. (28 pages).
Official Action Dated Aug. 4, 2023 from the US Patent and Trademark Office Re. U.S. Appl. No. 15/549,425. (21 pages).
Official Action Dated Aug. 4, 2023 from the US Patent and Trademark Office Re. U.S. Appl. No. 15/549,442. (32 pages).
Official Action Dated Jun. 21, 2023 From the US Patent and Trademark Office Re. U.S. Appl. No. 16/724,400. (37 Pages).
Pre Appeal Examination Dated Jun. 16, 2023 From the Japan Patent Office Re. Application No. 2021-128296 and Its Translation Into English. (6 Pages).
Requisition by the Examiner Dated Aug. 7, 2023 From the Innovation, Science and Economic Development Canada, Canadian Intellectual Property Office Re. Application No. 3,033,259. (5 Pages).
Search Report and Written Opinion Dated Jul. 13, 2023 From the Intellectual Property Office of Singapore, IPOS Re. Application No. 10202203602Y. (14 Pages).
Translation Dated Jul. 17, 2023 of Final Notice of Rejection Dated Jun. 27, 2023 From the Korean Intellectual Property Office Re. Application No. 10-2019-7007250. (4 Pages).
Covertino "Blood Volume Response to Physical Activity and Inactivity", The American Journal of the Medical Sciences, 334(1): 72-79, Jul. 2007.
Sugihara "Research on the Analysis of Factors for Variability in Drug Concentration in Blood After Administration of Oral Formulation", Dissertation in Okayama University Graduate School of Medicine, Dentistry and Pharmaceutical Sciences, Doctoral Course in Drug Discovery and Life Sciences, Mar. 28, 2016 (70 Pages).
Vinarov et al. "Impact of Gastrointestinal Tract Variability on Oral Drug Absorption and Pharmacokinetics: An UNGAP Review", European Journal of Pharmaceautical Sciences, 162, 105812, Jul. 1, 2021 (33 Pages).
Yano "Insulin Measurement," CDEJ News Letter, Apr. 30, 2011 (2 Pages).
Notice of Allowance Dated Apr. 24, 2024 From the US Patent and Trademark Office Re. U.S. Appl. No. 16/724,400. (27 pages).
Translation Dated Feb. 21, 2024 of Final Notice of Rejection Dated Jan. 15, 2024 From the Korean Intellectual Property Office Re. Application No. 10-2023-7019713. (4 Pages).
Communication Pursuant to Article 94(3) EPC Dated Mar. 4, 2023 From the European Patent Office Re. Application No. 16748834.5. (6 Pages).
Communication Pursuant to Article 94(3) EPC Dated Mar. 4, 2024 From the European Patent Office Re. Application No. 1674832.9. (6 Pages).
Notification of Office Action and Search Report Dated Nov. 28, 2023 From the State Intellectual Property Office of the People's Republic of China Re. Application No. 202111014634.9 and Its Translation of Office Action and Claims Into English. (28 Pages).
Examination Report Dated Aug. 23, 2023 From the Australian Government, IP Australia Re. Application No. 2017311698. (7 Pages).
Relatório de Busca e Parecer Dated Feb. 20, 2024 From the Serviço Público Federal, Ministério da Economia, Instituto Nacional da Propriedade Industrial do Brasil Re. Application No. BR 11 2019 003136 7 and Its Translation Into English. (6 Pages).
Examination Report Dated Sep. 7, 2023 From the Instituto Mexicano de la Propiedad Industrial, Secretaria de Economia, Direccion Divisional de Patentes Re. Application No. MX/a/2017/010220 and Its Translation Into English. (22 Pages).
Examination Report Dated Jun. 10, 2024 From the Instituto Mexicano de la Propiedad Industrial, Secretaria de Economia, Direccion Divisional de Patentes Re. Application No. MX/a/2019/001850 and Its Translation Into English. (14 Pages).
Examination Report Dated Jul. 16, 2024 From the Australian Government, IP Australia Re. Application No. 2017311698. (5 Pages).
Final Notice of Rejection Dated Jun. 3, 2024 From the Korean Intellectual Property Office Re. Application No. 10-2023-7019713. (5 Pages).
Machine Translation of Final Notice of Rejection Dated Jun. 3, 2024 From the Korean Intellectual Property Office Re. Application No. 10-2023-7019713. (5 Pages).
Notification of Office Action Dated May 24, 2024 From the State Intellectual Property Office of the People's Republic of China Re. Application No. 202111014634.9. (6 Pages).
Translation Dated Jun. 16, 2024 of Notification of Office Action Dated May 24, 2024 From the State Intellectual Property Office of the People's Republic of China Re. Application No. 202111014634.9. (10 Pages).

(56) References Cited

OTHER PUBLICATIONS

Grounds of Reason of Rejection Dated Aug. 5, 2024 From the Korean Intellectual Property Office Re. Application No. 10-2024-7016245 and Its Machine Translation Into English. (22 Pages).
Invitaion to Respond to Written Opinion Dated Aug. 13, 2024 From the Intellectual Property Office of Singapore, IPOS Re. Application No. 1020203602Y. (10 Pages).
Official Action Dated Sep. 10, 2024 from the US Patent and Tademark Office Re. U.S. Appl. No. 15/549,418. (27 pages).
Official Action Dated Sep. 10, 2024 from US Patent and Trademark Office Re. U.S. Appl. No. 15/549,394. (25 pages).
Requistion by the Examiner Dated Sep. 19, 2024 From the Innovation, Science and Economic Development Canada, Canadian Intellectual Property Office Re. Application No. 3,011,654. (9 Pages).
Official Action Dated Oct. 10, 2024 from US Patent and Trademark Office Re. U.S. Appl. No. 18/432,185. (100 pages).
Claims from Korean Application No. 10-2024-7016245 together with English Translation, Amended May 16, 2024 (8 Pages).
Grounds of Reason of Rejection Dated Oct. 14, 2024 From the Korean Intellectual Property Office Re. Application No. 10-2024-7029460 and it's Machine translation. (15 Pages).
Notice of Reason(s) for Rejection Dated Oct. 22, 2024 From the Japan Patent Office Re. Application No. 11,777,718 and its Translation Into English. (11 Pages).
Offica Action Dated Oct. 15, 2024 From the Israel Patent Office Re. Application No. 312218. (3 Pages).
Requistion by the Examiner Dated Nov. 1, 2024 From the Innovation, Science and Economic Development Canada, Canadian Intellectual Property Office Re. Application No. 2,975,676. (6 Pages).

* cited by examiner

FORMULATIONS FOR ORAL ADMINISTRATION OF ACTIVE AGENTS

RELATED APPLICATIONS

This application is a National Phase of PCT Patent Application No. PCT/IL2017/050920 having International filing date of Aug. 17, 2017, which claims the benefit of priority under 35 USC § 119(e) of U.S. Provisional Patent Application No. 62/375,989 filed on Aug. 17, 2016. The contents of the above applications are all incorporated by reference as if fully set forth herein in their entirety.

FIELD AND BACKGROUND OF THE INVENTION

The present invention, in some embodiments thereof, relates to drug delivery, and more particularly, but not exclusively, to formulations and/or systems for oral administration of therapeutically active agents.

Oral administration of peptide and/or protein pharmaceuticals is problematic due to degradation of peptides and/or proteins in the digestive system and poor absorption of large molecules.

U.S. Patent Application Publication No. 2007/0087957 describes compositions for oral administration of a protein, the compositions comprising a protein and an omega-3 fatty acid, as well as the use of such compositions for oral administration of insulin.

Qi & Ping [*J Microencapsulation* 2004, 21:37-45] describe administration of enteric microspheres containing insulin with SNAC (sodium 8-N-(2-hydroxybenzoyl)aminocaprylate). The enteric microspheres are for protecting the insulin from digestive enzymes of the stomach and small intestine, and the SNAC is for enhancing absorption.

U.S. Patent Application Publication No. 2011/0142800 describes compositions for oral administration of a protein, comprising a protein having a molecular weight of up to 100,000 Da, a protease inhibitor, and an absorption enhancer, such as SNAC, N-(10-[2-hydroxybenzoyl]amino) decanoic acid (SNAD), 8-[N-(2-hydroxy-4-methoxybenzoyl)amino]caprylic acid (4-MOAC), 8-[N-(2-hydroxy-5-chlorobenzoyl)amino]caprylic acid (5-CNAC) and 4-[(4-chloro-2-hydroxy-benzoyl)amino]butanoic acid (4-CNAB) and sodium salts thereof.

U.S. Pat. No. 8,110,547 describes compositions for buccal administration of parathyroid hormone (PTH). The composition comprises PTH or a fragment or analog thereof, as well as a delivery agent such as 4-MOAC, SNAC, SNAD, 5-CNAC and 4-CNAB.

Parathyroid hormone (PTH) is secreted by the parathyroid gland as a polypeptide containing 84 amino acids. PTH regulates serum calcium levels by enhancing release of calcium from bones (bone resorption), and by enhancing absorption of calcium in the intestines.

Teriparatide is a recombinant form of the first 34 amino acids of human PTH (PTH(1-34)), and is used for treatment of osteoporosis. Administration is by subcutaneous injection once per day at a dose of 20 μg [Riek & Towler, *Mo Med* 2011, 108:118-123].

PTH (including PTH(1-34)) has been reported to enhance bone growth provided that it is administered intermittently, with circulating levels returning to control levels within 3 hours [Martin, *J Bone Metab* 2014, 21:8-20]. In contrast, prolonged elevated PTH levels deplete bones by enhancing bone resorption.

Additional background art includes Qi et al. [*Acta Pharm Sinica* 2004, 39:844-848]; International Patent Applications PCT/IL2016/050151, PCT/IL2016/050152 PCT/IL2016/050153, PCT/IL2016/050154 and PCT/IL2016/050155; International Patent Application Publications WO 00/50386, WO 01/32130, WO 01/32596, WO 03/045306, WO 03/045331, WO 2006/076692, WO 2007/121471, WO2010/020978 and WO 2012/080471; Japanese Patent Application Nos. 2005281231 and 2006111558; and U.S. Patent Application Publication Nos. 2006/0234913 and 2013/0224300.

SUMMARY OF THE INVENTION

According to an aspect of some embodiments of the present invention there is provided a pharmaceutical composition multi-unit dosage form comprising at least two discrete unit dosage forms bound to one another by a coating and/or matrix, each of the unit dosage forms comprising a therapeutically active agent and an absorption enhancer, the unit dosage forms together comprising a therapeutically effective amount of the therapeutically active agent and an effective amount of the absorption enhancer, wherein the coating and/or matrix is formulated for immediate release of the unit dosage forms upon oral administration, and wherein the absorption enhancer is selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4- chlorobenzoyl)aminobutanoic acid) and salts thereof.

According to some of any of the embodiments described herein, the multi-unit dosage form is capable of disintegrating in gastric fluid and/or in saliva to thereby release the unit dosage forms.

According to some of any of the embodiments described herein, the disintegrating in gastric fluid is effected within no more than 5 minutes.

According to some of any of the embodiments described herein, the coating and/or matrix is soluble in gastric fluid and/or in saliva.

According to some of any of the embodiments described herein, the coating and/or matrix dissolves in gastric fluid within no more than 5 minutes.

According to some of any of the embodiments described herein, the coating and/or matrix comprises a disintegrant.

According to some of any of the embodiments described herein, the multi-unit dosage form comprises from 3 to 10 of the discrete unit dosage forms.

According to some of any of the embodiments described herein, the multi-unit dosage form comprises at least four of the discrete unit dosage forms.

According to some of any of the embodiments described herein, a maximal plasma concentration (Cmax) of the therapeutically active agent upon oral administration of the multi-unit dosage form is characterized by an inter-subject coefficient of variation of less than 100%.

According to some of any of the embodiments described herein, a maximal plasma concentration (Cmax) of the therapeutically active agent upon oral administration of the multi-unit dosage form is characterized by an inter-subject coefficient of variation which is at least 20% less than an inter-subject coefficient of variation of a maximal plasma concentration (Cmax) of the therapeutically active agent upon oral administration of a unit dosage form consisting of a single unit dosage form having the same total composition as the discrete unit dosage forms.

According to some of any of the embodiments described herein, an area under curve (AUC) of plasma concentration of the therapeutically active agent upon oral administration of the multi-unit dosage form is characterized by an inter-subject coefficient of variation of less than 100%.

According to some of any of the embodiments described herein, an AUC (area under curve) of plasma concentration of the therapeutically active agent upon oral administration of the multi-unit dosage form is characterized by an inter-subject coefficient of variation which is at least 20% less than an inter-subject coefficient of variation of an AUC of plasma concentration of the therapeutically active agent upon oral administration of a unit dosage form consisting of a single unit dosage form having the same total composition as the discrete unit dosage forms.

According to some of any of the embodiments described herein, a maximal plasma concentration (Cmax) of the therapeutically active agent upon oral administration of the multi-unit dosage form is at least 20% greater than a maximal plasma concentration (Cmax) of the therapeutically active agent upon oral administration of a unit dosage form consisting of a single unit dosage form having the same total composition as the discrete unit dosage forms.

According to some of any of the embodiments described herein, an AUC (area under curve) of plasma concentration of the therapeutically active agent upon oral administration of the multi-unit dosage form is at least 20% greater than an AUC of plasma concentration of the therapeutically active agent upon oral administration of a unit dosage form consisting of a single unit dosage form having the same total composition as the discrete unit dosage forms.

According to some of any of the embodiments described herein, the absorption enhancer comprises NAC or a salt thereof.

According to some of any of the embodiments described herein, at least 50 weight percents of the unit dosage forms consists of the absorption enhancer.

According to some of any of the embodiments described herein, the multi-unit dosage form comprises a total of at least 50 mg of the absorption enhancer in the at least two unit dosage forms.

According to some of any of the embodiments described herein, the therapeutically effective amount of the therapeutically active agent in the multi-unit dosage form is in a range of from 100 to 3000 μg.

According to some of any of the embodiments described herein, the multi-unit dosage form of any of the embodiments described herein, and any combination thereof, is for use in the treatment of a condition treatable by oral administration of the therapeutically active agent in a subject in need thereof.

According to an aspect of some embodiments of the present invention there is provided a pharmaceutical composition unit dosage form comprising a therapeutically active agent and an absorption enhancer, for use in the treatment of a condition treatable by the therapeutically active agent, the treatment comprising concomitant oral administration of at least two of the unit dosage form, wherein the at least two of the unit dosage form together comprise a therapeutically effective amount of the therapeutically active agent and an effective amount of the absorption enhancer, and wherein the absorption enhancer is selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4-chlorobenzoyl)aminobutanoic acid) and salts thereof.

According to some of any of the embodiments described herein, the treatment comprises concomitant oral administration of from 3 to 10 of the unit dosage form.

According to some of any of the embodiments described herein, the treatment comprises concomitant oral administration of at least four of the unit dosage form.

According to some of any of the embodiments described herein, a maximal plasma concentration (Cmax) of the therapeutically active agent upon the concomitant oral administration is characterized by an inter-subject coefficient of variation of less than 100% a.

According to some of any of the embodiments described herein, a maximal plasma concentration (Cmax) of the therapeutically active agent upon the concomitant oral administration of at least two of the unit dosage form is characterized by an inter-subject coefficient of variation which is at least 20% less than an inter-subject coefficient of variation of a maximal plasma concentration (Cmax) of the therapeutically active agent upon oral administration of a single unit dosage form having the same total composition as the at least two of the unit dosage form.

According to some of any of the embodiments described herein, an area under curve (AUC) of plasma concentration of the therapeutically active agent upon the concomitant oral administration is characterized by an inter-subject coefficient of variation of less than 100%.

According to some of any of the embodiments described herein, an AUC (area under curve) of plasma concentration of the therapeutically active agent upon the concomitant oral administration of at least two of the unit dosage form is characterized by an inter-subject coefficient of variation which is at least 20% less than an inter-subject coefficient of variation of an AUC of plasma concentration of the therapeutically active agent upon oral administration of a single unit dosage form having the same total composition as the at least two of the unit dosage form.

According to some of any of the embodiments described herein, a maximal plasma concentration (Cmax) of the therapeutically active agent upon concomitant oral administration of at least two of the unit dosage form is at least 20% greater than a maximal plasma concentration (Cmax) of the therapeutically active agent upon oral administration of a single unit dosage form having the same total composition as the at least two of the unit dosage form.

According to some of any of the embodiments described herein, an AUC (area under curve) of plasma concentration of the therapeutically active agent upon concomitant oral administration of at least two of the unit dosage form is at least 20% greater than an AUC of plasma concentration of the therapeutically active agent upon oral administration of a single unit dosage form having the same total composition as the at least two of the unit dosage form.

According to some of any of the embodiments described herein, the absorption enhancer comprises NAC or a salt thereof.

According to some of any of the embodiments described herein, at least 50 weight percents of the unit dosage form consists of the absorption enhancer.

According to some of any of the embodiments described herein, at least two of the unit dosage form together comprise at least 50 mg of the absorption enhancer.

According to some of any of the embodiments described herein, the therapeutically effective amount of the therapeutically active agent is in a range of from 100 to 3000 μg.

According to some of any of the embodiments described herein, for the multi-unit dosage form or unit dosage form for use according to any one of the embodiments described herein and any combination thereof, the treatment comprises reducing a variability of Cmax and/or AUC of plasma concentrations of the therapeutically active agent.

According to some of any of the embodiments described herein, the treatment comprises increasing a Cmax and/or a bioavailability of the therapeutically active agent.

According to some of any of the embodiments described herein, for the multi-unit dosage form or unit dosage form for use according to any one of the embodiments described herein and any combination thereof, the therapeutically active agent has a molecular weight in a range of 0.5 kDa to 100 kDa.

According to some of any of the embodiments described herein, for the multi-unit dosage form or unit dosage form for use according to any one of the embodiments described herein and any combination thereof, the therapeutically active agent is a BCS Class III agent.

According to some of any of the embodiments described herein, for the multi-unit dosage form or unit dosage form for use according to any one of the embodiments described herein and any combination thereof, the therapeutically active agent is a polypeptide.

According to some of any of the embodiments described herein, for the multi-unit dosage form or unit dosage form for use according to any one of the embodiments described herein and any combination thereof, the polypeptide is selected from the group consisting of parathyroid hormone and a fragment thereof.

According to some of any of the embodiments described herein, for the multi-unit dosage form or unit dosage form for use according to any one of the embodiments described herein and any combination thereof, the polypeptide comprises teriparatide.

According to an aspect of some embodiments of the present invention there is provided a pharmaceutical composition unit dosage form comprising less than 200 μg of parathyroid hormone or a fragment thereof, and an absorption enhancer selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4- chlorobenzoyl)aminobutanoic acid) and salts thereof.

According to some of any of the embodiments described herein, the unit dosage form is for use in the treatment of a condition treatable by the parathyroid hormone or a fragment thereof, the treatment comprising concomitant oral administration of at least two of the unit dosage form, wherein the at least two of the unit dosage form together comprise a therapeutically effective amount of the parathyroid hormone or a fragment thereof and an effective amount of the absorption enhancer.

According to an aspect of some embodiments of the present invention there is provided a pharmaceutical composition unit dosage form comprising parathyroid hormone or a fragment thereof, and an absorption enhancer, for use in the treatment of a condition treatable by the parathyroid hormone or a fragment thereof, the treatment comprising concomitant oral administration of at least two of the unit dosage form, wherein the at least two of the unit dosage form together comprise a therapeutically effective amount of the parathyroid hormone or a fragment thereof and an effective amount of the absorption enhancer, and wherein the absorption enhancer is selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4- chlorobenzoyl)aminobutanoic acid) and salts thereof.

According to some of any of the embodiments described herein, the unit dosage form comprises from 50 to 1000 μg of the parathyroid hormone or a fragment thereof.

According to some of any of the embodiments described herein, the condition treatable by the parathyroid hormone or a fragment thereof is selected from the group consisting of hypoparathyroidism, osteoporosis, and a medical condition associated with a bone fracture and/or bone defect.

According to an aspect of some embodiments of the present invention there is provided a kit comprising a plurality of sets of at least two unit dosage forms, the unit dosage forms comprising a therapeutically active agent and an absorption enhancer, wherein the at least two unit dosage forms together comprise a therapeutically effective amount of the therapeutically active agent and an effective amount of the absorption enhancer, and wherein the absorption enhancer is selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4- chlorobenzoyl)aminobutanoic acid) and salts thereof.

According to some of any of the embodiments described herein, the sets are packaged individually in the kit.

According to some of any of the embodiments described herein, the kit further comprises instructions for concomitantly administering orally the unit dosage forms in one or more of the sets.

According to an aspect of some embodiments of the present invention there is provided a method of treating a condition treatable by oral administration of a therapeutically active agent in a subject in need thereof, the method comprising orally administering to the subject the multi-unit dosage form as described herein in any of the respective embodiments and any combination thereof.

According to an aspect of some embodiments of the present invention there is provided a method of treating a condition treatable by oral administration of a therapeutically active agent in a subject in need thereof, the method comprising orally administering concomitantly at least two pharmaceutical composition unit dosage forms, each of the unit dosage forms comprising the therapeutically active agent and an absorption enhancer, wherein the at least two pharmaceutical composition unit dosage forms together comprise a therapeutically effective amount of the therapeutically active agent and an effective amount of the absorption enhancer, and wherein the absorption enhancer is selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4-chlorobenzoyl)aminobutanoic acid) and salts thereof.

According to some of any of the embodiments described herein, the method comprises reducing a variability of Cmax and/or AUC of plasma concentrations of the therapeutically active agent.

According to some of any of the embodiments described herein, the method comprises increasing a Cmax and/or a bioavailability of the therapeutically active agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3B is identical to FIG. 2B except for being presented on the same scale as FIG. 3A in order to facilitate comparison).

DESCRIPTION OF SPECIFIC EMBODIMENTS OF THE INVENTION

Figure 1A:
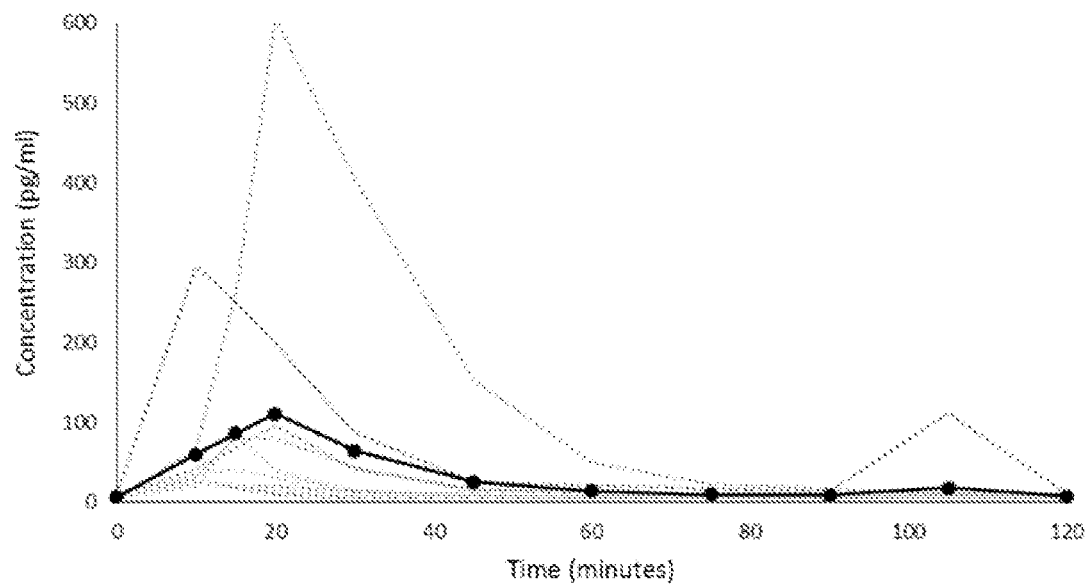
FIGS. 1A and 1B are graphs showing PTH(1-34) plasma concentrations as a function of time following oral administration of 0.69 mg PTH(1-34) in a multiple-unit formulation according to some embodiments of the invention (FIG. 1B) and in a single unit formulation (FIG. 1A) (black line represents average concentration among 10 subjects, and dashed lines represent concentrations for individual subjects).

The present invention, in some embodiments thereof, relates to drug delivery, and more particularly, but not exclusively, to formulations and/or systems for oral administration of therapeutically active agents.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While investigating the pharmacokinetics of orally administered pharmaceutical compositions comprising an exemplary absorption enhancer such as SNAC (sodium 8-N-(2-hydroxybenzoyl)aminocaprylate), the present inventors have surprisingly uncovered that separation of an exemplary solid composition comprising an absorption enhancer into two or more units administered concomitantly resulted in an improved effect of the composition.

For example, the present inventors have uncovered that that such orally administered pharmaceutical compositions comprising an absorption enhancer (such as NAC or a salt thereof) suffer from a high degree of variability in levels of absorbed agent, and that such variability can be surprisingly reduced by dividing the administered composition into separate units, even if the units are administered concomitantly. The inventors have further uncovered that the bioavailability of active agent in such orally administered compositions is surprisingly increased by dividing the administered composition into separate units.

While reducing the present invention to practice, the inventors have shown that separation of an exemplary solid composition comprising an absorption enhancer into two or more units administered concomitantly resulted in a reduced variability of maximal plasma concentration (Cmax) while also increasing the Cmax. The reduction in variability was to an extent such that the variability was similar to that associated with injection of a similar composition, or injection of a similar commercial subcutaneous injection.

Referring now to the drawings, FIGS. 1A-2B show that multi-unit oral formulations of teriparatide (parathyroid hormone (1-34)) exhibit less variability in plasma concentrations upon administration than do single unit oral formulations having the same amount of teriparatide. As shown in FIGS. 3A and 3B, the variability in teriparatide plasma concentrations upon oral administration of the multi-unit oral formulations is similar to that exhibited upon subcutaneous administration of teriparatide.

Figure 4:
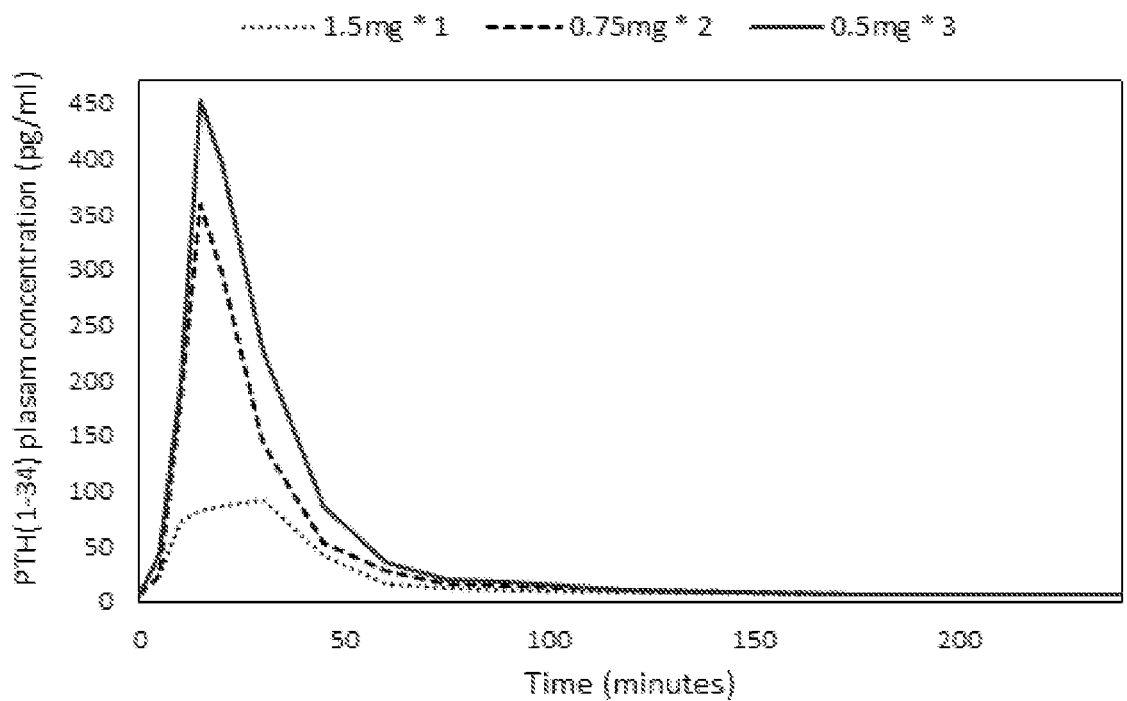
FIG. 4 is a graph showing PTH(1-34) plasma concentrations as a function of time following oral administration of 1.5 mg PTH(1-34) formulated as 3 units of 0.5 mg PTH(1-34), 2 units of 0.75 mg PTH(1-34)_or one unit of 1.5 mg PTH(1-34) (each data point represents the mean±standard error from 9 individuals).
Figure 5:
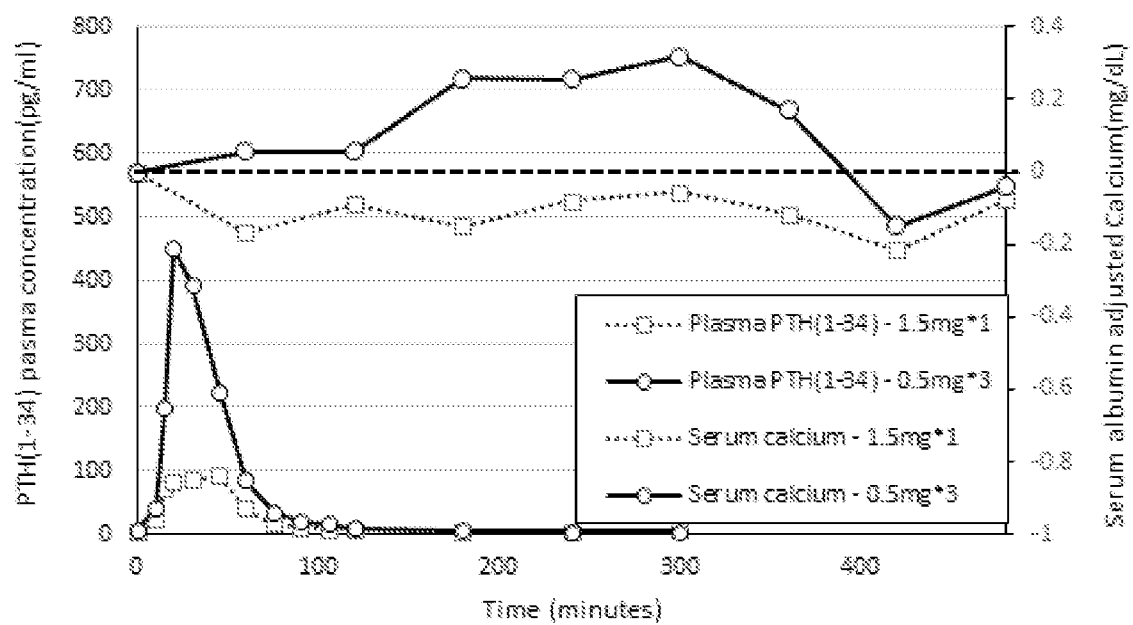
FIG. 5 is a graph showing PTH(1-34) plasma concentrations and albumin-adjusted serum calcium concentrations as a function of time following oral administration of 1.5 mg PTH(1-34) formulated as 3 units of 0.5 mg PTH(1-34)_or one unit of 1.5 mg PTH(1-34) (each data point represents the mean±standard error from 9 individuals).

As shown in FIG. 4, 2-unit and 3-unit oral formulations result in a higher Cmax than to single-unit formulations with the same amount of teriparatide. As shown in FIG. 5, the higher Cmax of teriparatide associated with multi-unit oral formulations is also associated with more potent activity (increase in serum calcium levels), in comparison with single-unit oral formulations.

Methods and Uses Utilizing Multiple Unit Dosage Forms:

According to an aspect of some embodiments of the invention, there is provided a pharmaceutical composition unit dosage form comprising a therapeutically active agent, for use in the treatment of a condition treatable by the therapeutically active agent, the treatment comprising concomitant oral administration of at least two of these unit dosage forms (according to any of the respective embodiments described herein). In some embodiments of any of the embodiments described herein, the pharmaceutical composition unit dosage form further comprises an absorption enhancer according to any of the respective embodiments described herein. In some embodiments according to any of the embodiments described herein, the treatment comprising concomitant oral administration of at least three of these unit dosage forms (according to any of the respective embodiments described herein).

According to an aspect of some embodiments of the invention, there is provided a method of treating a condition treatable by oral administration of a therapeutically active agent in a subject in need thereof, the method comprising orally administering concomitantly at least two pharmaceutical composition unit dosage forms (according to any of the respective embodiments described herein), each of the unit dosage forms comprising the therapeutically active agent. In some embodiments of any of the embodiments described herein, the pharmaceutical composition unit dosage form further comprises an absorption enhancer according to any of the respective embodiments described herein. In some embodiments according to any of the embodiments described herein, the method comprising orally administering concomitantly at least three pharmaceutical composition unit dosage forms (according to any of the respective embodiments described herein).

The term "unit dosage form", as used herein, describes physically discrete units, each unit containing a predetermined quantity of one or more active ingredient(s) calculated to produce, either alone or in the context of a predetermined number of the unit dosage forms, a desired therapeutic effect, optionally in association with at least one pharmaceutically acceptable carrier, diluent, excipient, or combination thereof.

Herein the term "therapeutically active agent" refers to the ingredient accountable for a therapeutic effect, as opposed, for example, to enhancement of absorption of the therapeutically active agent, as effected by an absorption enhancer according to any of the respective embodiments described herein.

According to some embodiments of any of the embodiments described herein, according to any of the aspects described herein, the at least two unit dosage forms (according to any of the respective embodiments described herein) together comprise a therapeutically effective amount of the therapeutically active agent (e.g., the therapeutically effective amount is divided among the at least two unit dosage forms). In some embodiments of any of the embodiments described herein, each of the at least two unit dosage forms comprises less than a therapeutically effective amount of the therapeutically active agent.

Herein, the terms "concomitant" and "concomitantly" refer to administration of a plurality of unit dosage forms within a span of no more than 4 hours (e.g., from administration of the first of a plurality of unit dosage forms to administration of the last of a plurality of unit dosage forms).

In some embodiments of any of the embodiments described herein, concomitant administration is effected by administration of a plurality of unit dosage forms within a span of no more than 2 hours. In some embodiments, concomitant administration is effected by administration within a span of no more than 60 minutes. In some embodiments, concomitant administration is effected by administration within a span of no more than 30 minutes. In some embodiments, concomitant administration is effected by administration within a span of no more than 20 minutes. In some embodiments, concomitant administration is effected by administration within a span of no more than 10 minutes. In some embodiments, concomitant administration is effected by administration within a span of no more than 5 minutes. In some embodiments, concomitant administration is effected by administration within a span of no more than 2 minutes. In some embodiments, concomitant administration is effected by administration within a span of no more than 1 minute.

According to some embodiments of any of the embodiments described herein, treatment (according to any of the methods or uses described herein) comprises concomitant oral administration of from 2 to 10 of the unit dosage forms (according to any of the respective embodiments described herein). In some embodiments, the treatment comprises concomitant oral administration of from 2 to 8 of the unit dosage forms. In some embodiments, the treatment comprises concomitant oral administration of from 2 to 6 of the unit dosage forms. In some embodiments, the treatment comprises concomitant oral administration of from 2 to 5 of the unit dosage forms. In some embodiments, the treatment comprises concomitant oral administration of from 2 to 4 of the unit dosage forms. In some embodiments, the treatment comprises concomitant oral administration of from 2 or 3 of the unit dosage forms. In some embodiments, the treatment comprises concomitant oral administration of 2 of the unit dosage forms.

According to some embodiments of any of the respective embodiments described herein (according to any of the aspects described herein), the at least two dosage forms comprise at least three dosage forms.

According to some embodiments of any of the embodiments described herein, treatment (according to any of the methods or uses described herein) comprises concomitant oral administration of at least 3 of the oral dosage forms (according to any of the respective embodiments described herein). In some embodiments, treatment (according to any of the methods or uses described herein) comprises concomitant oral administration of from 3 to 10 of the unit dosage forms (according to any of the respective embodiments described herein). In some embodiments, the treatment comprises concomitant oral administration of from 3 to 8 of the unit dosage forms. In some embodiments, the treatment comprises concomitant oral administration of from 3 to 6 of the unit dosage forms. In some embodiments, the treatment comprises concomitant oral administration of from 3 to 5 of the unit dosage forms. In some embodiments, the treatment comprises concomitant oral administration of from 3 or 4 of the unit dosage forms. In some embodiments, the treatment comprises concomitant oral administration of 3 of the unit dosage forms.

According to some embodiments of any of the embodiments described herein, treatment (according to any of the methods or uses described herein) comprises concomitant oral administration of at least 4 of the oral dosage forms (according to any of the respective embodiments described herein). In some embodiments, the treatment comprises concomitant oral administration of from 4 to 10 of the unit dosage forms. In some embodiments, the treatment comprises concomitant oral administration of from 4 to 8 of the unit dosage forms. In some embodiments, the treatment comprises concomitant oral administration of from 4 to 6 of the unit dosage forms. In some embodiments, the treatment comprises concomitant oral administration of from 4 to 5 of the unit dosage forms. In some embodiments, the treatment comprises concomitant oral administration of 4 of the unit dosage forms.

According to some embodiments of any of the embodiments described herein, a maximal plasma concentration (Cmax) of the therapeutically active agent upon concomitant oral administration of at least two unit dosage forms (according to any of the respective embodiments described herein) is characterized by an inter-subject coefficient of variation of less than 100%. In some such embodiments, the inter-subject coefficient of variation is less than 90%. In some embodiments, the inter-subject coefficient of variation is less than 80%. In some embodiments, the inter-subject coefficient of variation is less than 70%. In some embodiments, the inter-subject coefficient of variation is less than 60%. In some embodiments, the inter-subject coefficient of variation is less than 50%. In some embodiments, the inter-subject coefficient of variation is less than 40%. In some embodiments, the inter-subject coefficient of variation is less than 30%.

According to some embodiments of any of the embodiments described herein, an area under curve (AUC) of plasma concentration of the therapeutically active agent upon concomitant oral administration of at least two unit dosage forms (according to any of the respective embodiments described herein) is characterized by an inter-subject coefficient of variation of less than 100%. In some such embodiments, the inter-subject coefficient of variation is less than 90%. In some embodiments, the inter-subject coefficient of variation is less than 80%. In some embodiments, the inter-subject coefficient of variation is less than 70%. In some embodiments, the inter-subject coefficient of variation is less than 60%. In some embodiments, the inter-subject coefficient of variation is less than 50%. In some embodiments, the inter-subject coefficient of variation is less than 40%. In some embodiments, the inter-subject coefficient of variation is less than 30%.

As used herein the term "AUC" refers to the area under a curve which represents levels of the therapeutically active agent in the blood (e.g., plasma levels) as a function of time following administration, and can be determined by measuring plasma levels of the therapeutically active agent at various time points following administration, as exemplified herein.

As used herein the term "Cmax" refers to the maximal concentration of the therapeutically active agent in the blood (e.g., plasma levels), and can be determined by measuring levels of the therapeutically active agent at various time points following administration, as exemplified herein.

In determining a pharmacokinetic value (e.g., Cmax and/or AUC), concomitant administration is preferably effected by administration of the at least there unit dosage forms within a span of no more than 5 minutes, optionally no more than 2 minutes, and optionally no more than 1 minute.

Herein and in the art, the term "coefficient of variation" refers to a ratio of a standard deviation of values (e.g., of Cmax and/or AUC values) to the mean of the same values. As is common in the art, any ratio may be expressed as a percentage by multiplying by 100%.

Herein, the phrase "inter-subject coefficient of variation" refers to a coefficient of variation (as defined herein) wherein each value (e.g., Cmax and/or AUC value) is obtained from a different subject.

The skilled person will be readily capable of determining a coefficient of variation from data obtained from various subjects, as well as determining a suitably large sample for determining the coefficient of variation with the desired accuracy.

According to some embodiments of any of the embodiments described herein relating to a method or use, the treatment comprises reducing a variability of Cmax and/or AUC of plasma concentrations of the therapeutically active agent.

According to some embodiments of any of the embodiments described herein relating to a method or use, the treatment is for reducing a variability of Cmax and/or AUC of plasma concentrations of the therapeutically active agent.

Without being bound by any particular theory, it is believed that absorption of the therapeutically active agent (according to any of the respective embodiments described herein) may differ considerably at different locations in the gastrointestinal tract, such that the presence of at least two unit dosage forms in the gastrointestinal tract, each being in a different location, reduces the variability of overall absorption due to differences in local absorption.

According to some embodiments relating to reducing a variability of Cmax and/or AUC of plasma concentrations, the Cmax and/or AUC upon a treatment described herein exhibits less variability (e.g., as expressed by standard deviation or coefficient of variation) than a corresponding treatment by oral administration of a single unit dosage form, the single unit dosage form having the same total composition as the at least two unit dosage forms (according to any of the respective embodiments described herein).

A corresponding single unit dosage form (according to any of the respective embodiments described herein) is preferably formed by the same techniques as the at least two unit dosage forms to which it is compared, for example, wherein the at least two unit dosage forms and the corresponding single unit dosage form are each tablets (having the same excipients, if any) or are each capsules (having the same type of capsule shell), and so forth.

According to some embodiments of any of the embodiments described herein, a maximal plasma concentration (Cmax) of the therapeutically active agent upon concomitant oral administration of at least two unit dosage forms (according to any of the respective embodiments described herein) is characterized by an inter-subject coefficient of variation which is at least 20% less than an inter-subject coefficient of variation of a maximal plasma concentration (Cmax) of the therapeutically active agent upon oral administration of a corresponding single unit dosage form having the same total composition as the at least two of the unit dosage form. In some such embodiments, the inter-subject coefficient of variation is at least 30% less than the inter-subject coefficient of variation upon oral administration of the aforementioned single unit dosage form. In some such embodiments, the inter-subject coefficient of variation is at least 40% less than the inter-subject coefficient of variation upon oral administration of the aforementioned single unit dosage form. In some such embodiments, the inter-subject coefficient of variation is at least 50% less than the inter-subject coefficient of variation upon oral administration of the aforementioned single unit dosage form. In some such embodiments, the inter-subject coefficient of variation is at least 60% less than the inter-subject coefficient of variation upon oral administration of the aforementioned single unit dosage form. In some such embodiments, the inter-subject coefficient of variation is at least 70% less than the inter-subject coefficient of variation upon oral administration of the aforementioned single unit dosage form. In some such embodiments, the inter-subject coefficient of variation is at least 80% less than the inter-subject coefficient of variation upon oral administration of the aforementioned single unit dosage form. In some such embodiments, the inter-subject coefficient of variation is at least 90% less than the inter-subject coefficient of variation upon oral administration of the aforementioned single unit dosage form.

It is to be understood that "at least 20% less than" refers to no more than 80% (i.e., 100%-20%) of.

It is to be further understood that a value which is 20% less than 50% (e.g., a coefficient of variation of 50%) is 40% (i.e., 50%×(100%-20%)/100%), and not 30%. Similarly, a value which is 20% greater than 50% is 60% (and not 70%).

According to some embodiments of any of the embodiments described herein, an area under curve (AUC) of plasma concentration of the therapeutically active agent upon concomitant oral administration of at least two unit dosage forms (according to any of the respective embodiments described herein) is characterized by an inter-subject coefficient of variation which is at least 20% less than an inter-subject coefficient of variation of AUC of the therapeutically active agent upon oral administration of a corresponding single unit dosage form having the same total composition as the at least two of the unit dosage form. In some such embodiments, the inter-subject coefficient of variation is at least 30% less than the inter-subject coefficient of variation upon oral administration of the aforementioned single unit dosage form. In some such embodiments, the inter-subject coefficient of variation is at least 40% less than the inter-subject coefficient of variation upon oral administration of the aforementioned single unit dosage form. In some such embodiments, the inter-subject coefficient of variation is at least 50% less than the inter-subject coefficient of variation upon oral administration of the aforementioned single unit dosage form. In some such embodiments, the inter-subject coefficient of variation is at least 60% less than the inter-subject coefficient of variation upon oral administration of the aforementioned single unit dosage form. In some such embodiments, the inter-subject coefficient of variation is at least 70% less than the inter-subject coefficient of variation upon oral administration of the aforementioned single unit dosage form. In some such embodiments, the inter-subject coefficient of variation is at least 80% less than the inter-subject coefficient of variation upon oral administration of the aforementioned single unit dosage form. In some such embodiments, the inter-subject coefficient of variation is at least 90% less than the inter-subject coefficient of variation upon oral administration of the aforementioned single unit dosage form.

According to some embodiments of any of the embodiments described herein relating to a method or use, the treatment comprises increasing a Cmax (e.g., mean Cmax) and/or AUC (e.g., mean AUC) of plasma concentrations of the therapeutically active agent.

According to some embodiments of any of the embodiments described herein relating to a method or use, the treatment is for increasing a Cmax (e.g., mean Cmax) and/or AUC (e.g., mean AUC) of the therapeutically active agent.

As used herein, the term "bioavailability" refers to the fraction of a therapeutically active agent (e.g., in an oral formulation described herein) which reaches the systemic circulation (unchanged) upon administration.

Bioavailability of an oral formulation is optionally quantified as a ratio between AUC (divided by dosage) following oral administration to AUC (divided by dosage) following intravenous administration. Preferably, the drug dosage is equal in both formulations, such that it can be neglected.

Additionally or alternatively, the bioavailability of a plurality of oral formulations described herein (e.g., a multi-unit dosage form and a single unit dosage form, according to any of the respective embodiments) may optionally be quantified as a ratio between AUC values (divided by dosage) following oral administration, without necessarily determining AUC (divided by dosage) following intravenous administration (e.g., by assuming this is constant among formulations administered intravenously. Preferably, the drug dosage is equal in both formulations, such that it can be neglected.

Thus, a percentage increase (or decrease) in bioavailability (e.g., according to any of the respective embodiments described herein) may optionally be regarded as interchangeable herein with the same percentage increase (or decrease) in AUC (e.g., according to any of the respective embodiments described herein).

According to some embodiments of any of the embodiments described herein, a maximal plasma concentration (Cmax) of the therapeutically active agent upon concomitant oral administration of at least two unit dosage forms (according to any of the respective embodiments described herein) is at least 20% greater than a maximal plasma concentration (Cmax) of the therapeutically active agent upon oral administration of a corresponding single unit dosage form having the same total composition as the at least two of the unit dosage form. In some such embodiments, the Cmax is at least 30% greater than the Cmax upon oral administration of the aforementioned single unit dosage form. In some such embodiments, the Cmax is at least 50% greater than the Cmax upon oral administration of the aforementioned single unit dosage form. In some such embodiments, the Cmax is at least 75% greater than the Cmax upon oral administration of the aforementioned single unit dosage form. In some such embodiments, the Cmax is at least 100% greater than (i.e., twofold) the Cmax upon oral administration of the aforementioned single unit dosage form. In some such embodiments, the Cmax is at least 200% greater than (i.e., 3-fold) the Cmax upon oral administration of the aforementioned single unit dosage form. In some such embodiments, the Cmax is at least 300% greater than (i.e., 4-fold) the Cmax upon oral administration of the aforementioned single unit dosage form. In some such embodiments, the Cmax is at least 400% greater than (i.e., 5-fold) the Cmax upon oral administration of the aforementioned single unit dosage form. In some such embodiments, the Cmax is at least 500% greater than (i.e., 6-fold) the Cmax upon oral administration of the aforementioned single unit dosage form. In some such embodiments, the Cmax is at least 700% greater than (i.e., 8-fold) the Cmax upon oral administration of the aforementioned single unit dosage form. In some such embodiments, the Cmax is at least 800% greater than (i.e., 9-fold) the Cmax upon oral administration of the aforementioned single unit dosage form. In some such embodiments, the Cmax is at least 900% greater than (i.e., 10-fold) the Cmax upon oral administration of the aforementioned single unit dosage form.

According to some embodiments of any of the embodiments described herein, an AUC (area under curve) of the therapeutically active agent upon concomitant oral administration of at least two unit dosage forms (according to any of the respective embodiments described herein) is at least 20% greater than an AUC (area under curve) of the therapeutically active agent upon oral administration of a corresponding single unit dosage form having the same total composition as the at least two of the unit dosage form. In some such embodiments, the AUC is at least 30% greater than the AUC upon oral administration of the aforementioned single unit dosage form. In some such embodiments, the AUC is at least 50% greater than the AUC upon oral administration of the aforementioned single unit dosage form. In some such embodiments, the AUC is at least 75% greater than the AUC upon oral administration of the aforementioned single unit dosage form. In some such embodiments, the AUC is at least 100% greater than (i.e., twofold)

the AUC upon oral administration of the aforementioned single unit dosage form. In some such embodiments, the AUC is at least 200% greater than (i.e., 3-fold) the AUC upon oral administration of the aforementioned single unit dosage form. In some such embodiments, the AUC is at least 300% greater than (i.e., 4-fold) the AUC upon oral administration of the aforementioned single unit dosage form. In some such embodiments, the AUC is at least 400% greater than (i.e., 5-fold) the AUC upon oral administration of the aforementioned single unit dosage form. In some such embodiments, the AUC is at least 500% greater than (i.e., 6-fold) the AUC upon oral administration of the aforementioned single unit dosage form. In some such embodiments, the AUC is at least 700% greater than (i.e., 8-fold) the AUC upon oral administration of the aforementioned single unit dosage form. In some such embodiments, the AUC is at least 800% greater than (i.e., 9-fold) the AUC upon oral administration of the aforementioned single unit dosage form. In some such embodiments, the AUC is at least 900% greater than (i.e., 10-fold) the AUC upon oral administration of the aforementioned single unit dosage form.

According to some embodiments of any of the embodiments described herein, a bioavailability of the therapeutically active agent upon concomitant oral administration of at least two unit dosage forms (according to any of the respective embodiments described herein) is at least 0.05% (e.g., from 0.05 to 50% or from 0.05 to 5%). In some embodiments, the bioavailability is at least 0.1% (e.g., from 0.1 to 50% or from 0.1 to 5%). In some embodiments, the bioavailability is at least 0.2% (e.g., from 0.2 to 50% or from 0.2 to 5%). In some embodiments, the bioavailability is at least 0.3% (e.g., from 0.3 to 50% or from 0.3 to 5%). In some embodiments, the bioavailability is at least 0.4% (e.g., from 0.4 to 50% or from 0.4 to 5%). In some embodiments, the bioavailability is at least 0.5% (e.g., from 0.5 to 50% or from 0.5 to 5%). In some embodiments, the bioavailability is at least 0.5% (e.g., from 0.6 to 50% or from 0.6 to 5%). In some embodiments, the bioavailability is at least 0.7% (e.g., from 0.7 to 50% or from 0.7 to 5%). In some embodiments, the bioavailability is at least 0.8% (e.g., from 0.8 to 50% or from 0.8 to 5%). In some embodiments, the bioavailability is at least 1% (e.g., from 1 to 50% or from 1 to 5%). In some embodiments, the bioavailability is at least 1.25% (e.g., from 1.25 to 50% or from 1.25 to 5%). In some embodiments, the bioavailability is at least 1.5% (e.g., from 1.5 to 50% or from 1.5 to 5%). In some embodiments, the bioavailability is at least 2% (e.g., from 2 to 50% or from 2 to 5%). In some embodiments, the bioavailability is at least 3% (e.g., from 3 to 50% or from 3 to 5%). In some embodiments, the bioavailability is at least 5% (e.g., from 5 to 50%). In some of any of the aforementioned embodiments relating to bioavailability, the therapeutically active agent is PTH (according to any of the respective embodiments described herein), optionally PTH(1-34).

In some embodiments of any one of the embodiments described herein, treatment according to any of the aspects described herein is effected by orally administering the unit dosage forms on a relatively empty stomach and small intestines.

In some embodiments of any one of the embodiments described herein, oral administration of the unit dosage forms is effected at least 2 hours after the most recent food intake. In some embodiments, oral administration of the unit dosage forms is effected at least 4 hours after the most recent food intake. In some embodiments, oral administration of the unit dosage forms is effected at least 6 hours after the most recent food intake. In some embodiments, oral administration of the unit dosage forms is effected at least 8 hours after the most recent food intake. In some embodiments, oral administration of the unit dosage forms is effected at least 10 hours after the most recent food intake.

In some embodiments of any one of the embodiments described herein, oral administration of the unit dosage forms is effected at least 2 hours after the most recent intake of food or drink. In some embodiments, oral administration of the unit dosage forms is effected at least 4 hours after the most recent intake of food or drink. In some embodiments, oral administration of the unit dosage forms is effected at least 6 hours after the most recent intake of food or drink. In some embodiments, oral administration of the unit dosage forms is effected at least 8 hours after the most recent intake of food or drink. In some embodiments, oral administration of the unit dosage forms is effected at least 10 hours after the most recent intake of food or drink.

In some embodiments of any one of the embodiments described herein, oral administration of the unit dosage forms is effected in the morning prior to eating. In some embodiments, oral administration of the unit dosage forms is effected in the morning prior to eating or drinking. Such administration of the unit dosage forms device in the morning (e.g., after sleeping) may optionally be the most convenient way for a subject to ensure that a considerable period of time has passed between oral administration and the most recent intake of food (and optionally drink).

In some embodiments of any one of the embodiments described herein, oral administration of the unit dosage forms is effected at least 10 minutes prior to eating (e.g., a subject should abstain from eating for at least 10 minutes after administration). In some embodiments, oral administration of the unit dosage forms is effected at least 20 minutes prior to eating. In some embodiments, oral administration of the unit dosage forms is effected at least 30 minutes prior to eating. In some embodiments, oral administration of the unit dosage forms is effected at least 60 minutes (1 hour) prior to eating. In some embodiments, oral administration of the unit dosage forms is effected at least 2 hours prior to eating. In some embodiments, oral administration of the unit dosage forms s effected at least 3 hours prior to eating. In some embodiments oral administration of the unit dosage forms is effected at least 4 hours prior to eating.

In some embodiments of any one of the embodiments described herein, oral administration of the unit dosage forms is effected at least 10 minutes prior to eating or drinking (e.g., a subject should abstain from eating or drinking for at least 10 minutes after administration). In some embodiments, oral administration of the unit dosage forms is effected at least 20 minutes prior to eating or drinking. In some embodiments, oral administration of the unit dosage forms is effected at least 30 minutes prior to eating or drinking. In some embodiments, oral administration of the unit dosage forms is effected at least 60 minutes (1 hour) prior to eating or drinking. In some embodiments, oral administration of the unit dosage forms is effected at least 2 hours prior to eating or drinking. In some embodiments, oral administration of the unit dosage forms is effected at least 3 hours prior to eating or drinking. In some embodiments, oral administration of the unit dosage forms is effected at least 4 hours prior to eating or drinking.

Without being bound by any particular theory, it is believed that food (and optionally drink) in the stomach and small intestines may interact with the absorption enhancer and/or PTH in a manner which is detrimental to absorption of the PTH in an efficient and predictable manner.

Kits:

According to an aspect of some embodiments of the invention, there is provided a kit comprising a plurality of sets of unit dosage forms comprising a therapeutically active agent and absorption enhancer (according to any of the respective embodiments described herein), each set comprising at least two unit dosage forms, optionally at least 3 unit dosage forms, and optionally at least 4 unit dosage forms. The number of dosage forms per set is optionally in accordance with any range and/or number of unit dosage forms described herein for effecting a method or use, according to any of the respective embodiments described herein).

In some embodiments of any of the embodiments described herein, the number of dosage forms per set is optionally relatively low, such as 2 or 3 or 4 or 5 (optionally 2 or 3 or 4), such that concomitant administration of larger numbers of unit dosage forms, if desired, may optionally be effected using more than one set of unit dosage forms.

In some embodiments of any of the embodiments described herein, the sets of unit dosage forms in a kit are packaged individually in the kit, for example, packaged in metal or plastic foil, such as a blister pack.

In some embodiments of any of the embodiments described herein, the kit comprises a dispenser for dispensing a set comprising a predetermined number of unit dosage forms (according to any of the respective embodiments described herein) and/or a device (e.g., a suitably shaped and/or marked container) for conveniently measuring a set comprising a predetermined number of unit dosage forms (according to any of the respective embodiments described herein).

In some embodiments of any of the embodiments described herein, the kit further comprises instructions for concomitantly administering orally the unit dosage forms in one or more of the sets of unit dosage forms, according to any of the respective embodiments described herein. For example, the instructions may optionally relate to concomitant oral administration of unit dosage forms which together comprise a therapeutically effective amount of the therapeutically active agent, according to any of the respective embodiments described herein.

Multi-Unit Dosage Form:

According to an aspect of some embodiments of the invention, there is provided a pharmaceutical composition multi-unit dosage form comprising at least two discrete unit dosage forms bound to one another by a coating and/or matrix, each of the unit dosage forms comprising a therapeutically active agent and an absorption enhancer (according to any of the respective embodiments described herein), wherein the coating and/or matrix is formulated for immediate release of the unit dosage forms upon oral administration. Immediate release of the unit dosage forms upon oral administration may optionally effect oral administration of at least two unit dosage forms according to any of the respective embodiments described herein.

In some of any of the embodiments described herein, the pharmaceutical composition multi-unit dosage form comprises at least three discrete unit dosage forms bound to one another by a coating and/or matrix, e.g., each of the unit dosage forms comprising a therapeutically active agent and absorption enhancer (according to any of the respective embodiments described herein).

Herein, the term "multi-unit dosage form: refers to any dosage form comprising a plurality of individual unit dosage forms, as defined herein.

Herein, the phrase "coating and/or matrix" refers to any substance capable of holding the discrete unit dosage forms together.

The term "coating" encompasses any substance which at least partially surrounds the unit dosage forms, including, without limitation, coatings which adhere to a surface of a unit dosage form (e.g., a coating applied onto the surface of the unit dosage form) as well as structures which envelop (loosely or tightly) the unit dosage forms (e.g., a capsule shell encapsulating the unit dosage forms).

The term "matrix" encompasses any substance which is present (at least in part) between the unit dosage forms, including, without limitation, an adhesive substance which attaches unit dosage forms to one another, as well as a continuous matrix which individually envelops (loosely or tightly) each unit dosage form.

In some embodiments of any of the embodiments described herein, the multi-unit dosage form is capable of disintegrating in gastric fluid and/or in saliva to thereby release the unit dosage forms.

Without being bound by any particular theory, it is believed that multi-unit dosage forms which disintegrate in gastric fluid according to any of the respective embodiments described herein may disintegrate in the stomach upon oral administration in a sufficiently rapid manner (e.g., prior to most absorption of the therapeutically active agent) so as to have a similar pharmacokinetic profile as could be obtained by concomitant oral administration of discrete unit dosage forms (which may be less convenient than administration of a single multi-unit dosage form). Similarly, it is believed multi-unit dosage forms which disintegrate in saliva according to any of the respective embodiments described herein may disintegrate in the mouth upon oral administration in a sufficiently rapid manner (e.g., prior to swallowing) so as to have essentially the same effect as concomitant oral administration of discrete unit dosage forms (which may be less convenient than administration of a single multi-unit dosage form).

In some embodiments of any of the embodiments described herein, the multi-unit dosage form is capable of disintegrating in gastric fluid within no more than 5 minutes to thereby release the unit dosage forms. In some such embodiments, the multi-unit dosage form is capable of disintegrating in gastric fluid within no more than 3 minutes to thereby release the unit dosage forms. In some embodiments, the multi-unit dosage form is capable of disintegrating in gastric fluid within no more than 2 minutes to thereby release the unit dosage forms. In some such embodiments, the multi-unit dosage form is capable of disintegrating in gastric fluid within no more than 1 minute to thereby release the unit dosage forms. In some such embodiments, the multi-unit dosage form is capable of disintegrating in gastric fluid within no more than 30 seconds to thereby release the unit dosage forms. In some such embodiments, the multi-unit dosage form is capable of disintegrating in gastric fluid within no more than 10 seconds to thereby release the unit dosage forms.

Herein, any of the properties described herein (e.g., disintegration, dissolution) in gastric fluid refer to a simulated gastric fluid without pepsin, at pH 2.0, under conditions according to USP 23 Apparatus 2 (paddle) (e.g., 800 ml volume, 50 rotations per minute).

In some embodiments of any of the embodiments described herein, the multi-unit dosage form is capable of disintegrating in saliva within no more than 1 minute to thereby release the unit dosage forms. In some such embodiments, the multi-unit dosage form is capable of disintegrating in saliva within no more than 30 seconds to thereby release the unit dosage forms. In some such embodiments, the multi-unit dosage form is capable of disintegrating in saliva within no more than 10 seconds to thereby release the unit dosage forms. In some such embodiments, the multi-unit dosage form is capable of disintegrating in saliva within no more than 5 seconds to thereby release the unit dosage forms.

Any of the properties described herein (e.g., disintegration, dissolution) in saliva may optionally be determined using saliva samples and/or a simulated saliva (without enzymes), at pH 7, under conditions according to USP 23 Apparatus 2 (paddle) (e.g., 800 ml volume, 50 rotations per minute).

In some embodiments of any of the embodiments described herein relating to a multi-unit dosage form capable of disintegrating in saliva, the multi-unit dosage form is formed using any techniques known in the art which are suitable for forming an orally disintegrating dosage form (e.g., an orally disintegrating tablet).

In some embodiments of any of the embodiments described herein, the coating and/or matrix dissolves in gastric fluid and/or in saliva.

In some embodiments of any of the embodiments described herein, the coating and/or matrix dissolves in gastric fluid within no more than 5 minutes. In some such embodiments, the coating and/or matrix dissolves in gastric fluid within no more than 3 minutes. In some embodiments, the coating and/or matrix dissolves in gastric fluid within no more than 2 minutes. In some embodiments, the coating and/or matrix dissolves in gastric fluid within no more than 1 minute. In some embodiments, the coating and/or matrix dissolves in gastric fluid within no more than 30 seconds. In some embodiments, the coating and/or matrix dissolves in gastric fluid within no more than 10 seconds.

In some embodiments of any of the embodiments described herein, the coating and/or matrix dissolves in saliva within no more than 60 seconds. In some embodiments, the coating and/or matrix dissolves in saliva within no more than 30 seconds. In some embodiments, the coating and/or matrix dissolves in saliva within no more than 10 seconds. In some embodiments, the coating and/or matrix dissolves in saliva within no more than 5 seconds.

Dissolution of the coating and/or matrix may be determined in a liquid (e.g., simulated gastric fluid, saliva) as described herein, using a multi-unit dosage form (as described herein), or alternatively, using a similar amount of the substance from which the coating and/or matrix is formed (e.g., a multi-unit dosage form from which the unit dosage forms are absent). Dissolution is indicated by absence of visible material of the original coating and/or matrix substance. However, visible material in the liquid (e.g., suspended in the liquid) which is derived from, but separate from the original coating and/or matrix substance, is not excluded by the terms "dissolves" and "dissolution".

In some embodiments of any of the embodiments described herein relating to a multi-unit dosage form capable of disintegrating in saliva, the matrix and/or coating is formed from any composition known in the art which is suitable for forming an orally disintegrating dosage form (e.g., an orally disintegrating tablet).

In some embodiments of any of the respective embodiments described herein, the coating and/or matrix comprises a disintegrant.

Herein, the term "disintegrant" refers to a substance which expands (e.g., by swelling and/or gas formation) and/or dissolves upon contact with moisture (e.g., in the digestive tract), thereby resulting in disintegration of a dosage form comprising the disintegrant.

Examples of disintegrants include, without limitation, crosslinked polyvinylpyrrolidone (crospovidone), crosslinked carboxymethyl cellulose (croscarmellose, e.g., sodium croscarmellose), non-crosslinked carboxymethyl cellulose (e.g., sodium carboxymethyl cellulose), starch (e.g., pregelatinized starch), sodium starch glycolate, methylcellulose, hydroxypropylmethylcellulose, microcrystalline cellulose, sodium bicarbonate, and alginic acid (including salts thereof).

In some embodiments of any of the respective embodiments described herein, the coating and/or matrix comprises a disintegrant at an effective concentration thereof. Effective concentrations of various disintegrants will be known to the skilled person.

An example of an effective concentration of crosslinked polyvinylpyrrolidone includes, without limitation, a concentration of from 0.5 to 5 weight percents.

An example of an effective concentration of crosslinked carboxymethyl cellulose includes, without limitation, a concentration of from 1 to 4 weight percents.

An example of an effective concentration of starch (e.g., pregelatinized starch) includes, without limitation, a concentration of from 5 to 20 weight percents.

An example of an effective concentration of sodium starch glycolate includes, without limitation, a concentration of from 2 to 8 weight percents.

An example of an effective concentration of non-crosslinked carboxymethyl cellulose (e.g., sodium carboxymethyl cellulose), methyl cellulose and/or hydroxypropylmethylcellulose includes, without limitation, a concentration of from 5 to 10 weight percents.

An example of an effective concentration of microcrystalline cellulose includes, without limitation, a concentration of from 10 to 20 weight percents.

An example of an effective concentration of alginic acid (including salts thereof) includes, without limitation, a concentration of from 1 to 10 weight percents.

In some embodiments of any of the embodiments described herein wherein release of the unit dosage forms is particularly rapid (e.g., wherein disintegration occurs in the mouth prior to swallowing), an effective concentration of a disintegrant according to any of the respective embodiments described herein may be relatively high, for example, above a concentration range described hereinabove.

The at least two unit dosage forms in the multi-unit dosage forms may be equal (e.g., in size, shape and/or composition) or different from one another (optionally in accordance with a statistical distribution).

In some embodiments of any of the embodiments described herein, the number of unit dosage forms in the multi-unit dosage form is in a range of from 2 to 10, optionally from 3 to 10, and optionally from 4 to 10, according to any of the respective ranges described herein with respect to a method or use.

In some embodiments of any of the embodiments described herein, the number of unit dosage forms in the multi-unit dosage form is more than 10, optionally more than 30, and optionally more than 100.

Unit dosage forms in relatively small quantities (e.g., no more than 10) may optionally be in the form of tablets or pellets (e.g., having a regular size and shape), which may be formed by any suitable technique known in the art (e.g., compression).

Unit dosage forms in large quantities (e.g., more than 10) may optionally be in the form of granules, which may optionally be formed by any suitable technique known in the art (e.g., spheronization).

In some embodiments of any of the embodiments described herein, the multi-unit dosage form is formulated such that oral administration of the multi-unit dosage form effects concomitant administration of at least two unit dosage forms according to any of the respective embodiments described herein.

According to some embodiments of any of the embodiments described herein, a maximal plasma concentration (Cmax) of the therapeutically active agent upon oral administration of the multi-unit dosage form (according to any of the respective embodiments described herein) is characterized by an inter-subject coefficient (as defined herein) of variation of less than 100%. In some such embodiments, the inter-subject coefficient of variation is less than 90%. In some embodiments, the inter-subject coefficient of variation is less than 80%. In some embodiments, the inter-subject coefficient of variation is less than 70%. In some embodiments, the inter-subject coefficient of variation is less than 60%. In some embodiments, the inter-subject coefficient of variation is less than 50%. In some embodiments, the inter-subject coefficient of variation is less than 40%. In some embodiments, the inter-subject coefficient of variation is less than 30%.

According to some embodiments of any of the embodiments described herein, an area under curve (AUC) of plasma concentration of the therapeutically active agent upon oral administration of the multi-unit dosage form (according to any of the respective embodiments described herein) is characterized by an inter-subject coefficient of variation (as defined herein) of less than 100%. In some such embodiments, the inter-subject coefficient of variation is less than 90%. In some embodiments, the inter-subject coefficient of variation is less than 80%. In some embodiments, the inter-subject coefficient of variation is less than 70%. In some embodiments, the inter-subject coefficient of variation is less than 60%. In some embodiments, the inter-subject coefficient of variation is less than 50%. In some embodiments, the inter-subject coefficient of variation is less than 40%. In some embodiments, the inter-subject coefficient of variation is less than 30%.

According to some embodiments relating to reducing a variability of Cmax and/or AUC of plasma concentrations, the Cmax and/or AUC upon oral administration of a multi-unit dosage form described exhibits less variability (e.g., as expressed by standard deviation or coefficient of variation) than a corresponding treatment by oral administration of a single unit dosage form, the single unit dosage form having the same total composition as the at least two unit dosage forms (according to any of the respective embodiments described herein).

A corresponding single unit dosage form (according to any of the respective embodiments described herein) is preferably formed by the same techniques as the unit dosage forms in the multi-unit dosage form to which it is compared, for example, wherein the at least two unit dosage forms and the corresponding single unit dosage form are each in a form of a tablet or pellet (having the same excipients, if any), which is encapsulated (e.g., within a capsule shell) or non-encapsulated.

According to some embodiments of any of the embodiments described herein, a maximal plasma concentration (Cmax) of the therapeutically active agent upon oral administration of the multi-unit dosage form (according to any of the respective embodiments described herein) is characterized by an inter-subject coefficient of variation which is at least 20% less than an inter-subject coefficient of variation of a maximal plasma concentration (Cmax) of the therapeutically active agent upon oral administration of a corresponding single unit dosage form having the same total composition as the at least two unit dosage forms in the multi-unit dosage form. In some such embodiments, the inter-subject coefficient of variation is at least 30% less than the inter-subject coefficient of variation upon oral administration of the aforementioned single unit dosage form. In some such embodiments, the inter-subject coefficient of variation is at least 40% less than the inter-subject coefficient of variation upon oral administration of the aforementioned single unit dosage form. In some such embodiments, the inter-subject coefficient of variation is at least 50% less than the inter-subject coefficient of variation upon oral administration of the aforementioned single unit dosage form. In some such embodiments, the inter-subject coefficient of variation is at least 60% less than the inter-subject coefficient of variation upon oral administration of the aforementioned single unit dosage form. In some such embodiments, the inter-subject coefficient of variation is at least 70% less than the inter-subject coefficient of variation upon oral administration of the aforementioned single unit dosage form. In some such embodiments, the inter-subject coefficient of variation is at least 80% less than the inter-subject coefficient of variation upon oral administration of the aforementioned single unit dosage form. In some such embodiments, the inter-subject coefficient of variation is at least 90% less than the inter-subject coefficient of variation upon oral administration of the aforementioned single unit dosage form.

According to some embodiments of any of the embodiments described herein, an area under curve (AUC) of plasma concentration of the therapeutically active agent upon oral administration of the multi-dosage form (according to any of the respective embodiments described herein) is characterized by an inter-subject coefficient of variation which is at least 20% less than an inter-subject coefficient of variation of AUC of the therapeutically active agent upon oral administration of a corresponding single unit dosage form having the same total composition as the at least two unit dosage forms in the multi-unit dosage form. In some such embodiments, the inter-subject coefficient of variation is at least 30% less than the inter-subject coefficient of variation upon oral administration of the aforementioned single unit dosage form. In some such embodiments, the inter-subject coefficient of variation is at least 40% less than the inter-subject coefficient of variation upon oral administration of the aforementioned single unit dosage form. In some such embodiments, the inter-subject coefficient of variation is at least 50% less than the inter-subject coefficient of variation upon oral administration of the aforementioned single unit dosage form. In some such embodiments, the inter-subject coefficient of variation is at least 60% less than the inter-subject coefficient of variation upon oral administration of the aforementioned single unit dosage form. In some such embodiments, the inter-subject coefficient of variation is at least 70% less than the inter-subject coefficient of variation upon oral administration of the aforementioned single unit dosage form. In some such embodiments, the inter-subject coefficient of variation is at least 80% less than the inter-subject coefficient of variation upon oral administration of the aforementioned single unit dosage form. In some such embodiments, the inter-subject coefficient of variation is at least 90% less than the inter-subject coefficient of variation upon oral administration of the aforementioned single unit dosage form.

In some embodiments of any of the embodiments described herein, the multi-unit dosage form according to any of the respective embodiments described herein is for use in the treatment of a condition treatable by oral administration of the therapeutically active agent (according to any of the respective embodiments described herein).

According to an aspect of some embodiments of the invention, there is provided a method of treating a condition treatable by oral administration of a therapeutically active agent (according to any of the respective embodiments described herein) in a subject in need thereof, the method comprising orally administering to the subject a multi-unit dosage form according to any of the respective embodiments described herein comprising the respective therapeutically active agent (according to any of the respective embodiments described herein).

Absorption Enhancer:

According to preferred embodiments of any of the embodiments described herein, the at least two dosage forms (according to any of the respective embodiments described herein) together comprise an effective amount of an absorption enhancer, i.e., an amount of absorption enhancer effective for enhancing absorption of the therapeutically active agent in the dosage forms.

Herein, the term "absorption enhancer" refers to a compound known in which enhances absorption of macromolecular drugs (e.g., compounds having a molecular weight of at least 1 kDa) from the gastrointestinal tract into the circulation upon oral administration of the drug. The person skilled in the art will be aware of many such absorption enhancers.

In some of any of the embodiments described herein, the absorption enhancer is a fatty acid with a terminal N-(2-hydroxybenzoyl)amino group (at the omega position, i.e., the terminus distal from the carboxylate group of the fatty acid), or a salt thereof (e.g., a monosodium or disodium salt) thereof.

The fatty acid is from 4 to 20 carbon atoms in length, optionally from 4 to 18 carbon atoms in length, optionally from 4 to 16 carbon atoms in length, optionally from 4 to 14 carbon atoms in length, optionally from 4 to 12 carbon atoms in length and optionally from 4 to 10 carbon atoms in length. In some of any of the embodiments described herein, the fatty acid is from 6 to 20 carbon atoms in length, optionally from 6 to 18 carbon atoms in length, optionally from 6 to 16 carbon atoms in length, optionally from 6 to 14 carbon atoms in length, optionally from 6 to 12 carbon atoms in length, optionally from 6 to 10 carbon atoms in length, and optionally from 8 to 10 carbon atoms in length. The fatty acid moiety may be saturated (e.g., as are caprylic acid in NAC and decanoic acid in NAD) or unsaturated (i.e., comprising at least one unsaturated carbon-carbon bond).

Examples of suitable fatty acids include, without limitation, butanoic acid, caprylic acid and decanoic acid.

The N-(2-hydroxybenzoyl)amino group may optionally be substituted or non-substituted (e.g., on the aromatic ring thereof). Suitable substituents include, for example, halo (optionally chloro) and alkoxy (optionally methoxy). Examples of substituted N-(2-hydroxybenzoyl)amino groups include, without limitation, N-(5-chlorosalicyloyl)amino, N-(4-chloro-2-hydroxybenzoyl)amino, and N-(2-hydroxy-4-methoxybenzoyl)amino.

Examples of suitable absorption enhancers include, without limitation, NAC (8-N-(2-hydroxybenzoyl)aminocaprylic acid) and NAD (10-N-(2-hydroxybenzoyl)aminodecanoic acid) and salts thereof (e.g., monosodium and disodium salts); as well as derivatives thereof (e.g., derivatives substituted by chloro and/or methoxy) such as 5-CNAC (8-N-(5-chlorosalicyloyl)aminocaprylic acid) and 4-MOAC (8-N-(2-hydroxy-4-methoxybenzoyl)aminocaprylic acid) and salts thereof (e.g., monosodium and disodium salts).

In some of any of the embodiments described herein, the absorption enhancer is in a form of a salt thereof, for example, a sodium salt. In exemplary embodiments, the sodium salt is a monosodium salt.

In some of any of the embodiments described herein, the absorption enhancer is NAC or NAD, or a salt thereof. In some such embodiments, the absorption enhancer is NAC or a salt thereof.

As shown below, the structure of NAD (depicted as a sodium salt thereof, also referred to as "SNAD") differs from that of NAC (depicted as a sodium salt thereof, also referred to as "SNAC") only in the length of the fatty acid moiety. Additional absorption enhancers related to NAC and NAD, based on different fatty acid lengths, will be readily apparent to the skilled person.

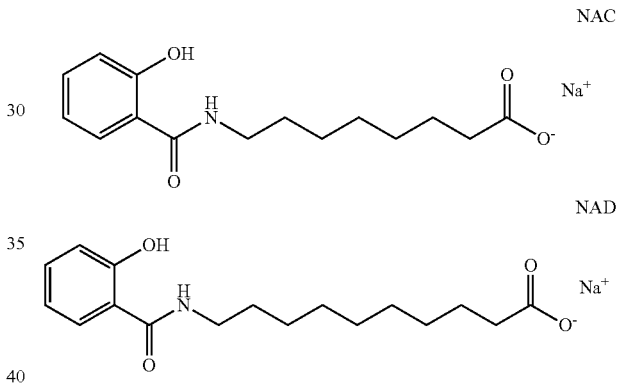

In some embodiments of any one of the embodiments described herein, a concentration of absorption enhancer in the at least two unit dosage forms described herein (taken together), and optionally in each of the unit dosage forms, is in a range of from 2.5 to 99.4 weight percents. In some of the aforementioned embodiments, the concentration of absorption enhancer is in a range of from 2.5 to 10 weight percents. In some of the aforementioned embodiments, the concentration of absorption enhancer is in a range of from 8 to 15 weight percents. In some of the aforementioned embodiments, the concentration of absorption enhancer is in a range of from 10 to 20 weight percents. In some of the aforementioned embodiments, the concentration of absorption enhancer is in a range of from 15 to 30 weight percents. In some of the aforementioned embodiments, the concentration of absorption enhancer is in a range of from 20 to 40 weight percents. In some of the aforementioned embodiments, the concentration of absorption enhancer is in a range of from 30 to 50 weight percents. In some of the aforementioned embodiments, the concentration of absorption enhancer is in a range of from 40 to 60 weight percents. In some of the aforementioned embodiments, the concentration of absorption enhancer is in a range of from 50 to 70 weight percents. In some of the aforementioned embodiments, the concentration of absorption enhancer is in a range of from 70 to 99.4 weight percents. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a concentration of absorption enhancer in the at least two unit dosage forms described herein (taken together), and optionally in each of the unit dosage forms, is at least 50 weight percents. In some embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is at least about 0.1 mg. In some embodiments, the total amount of absorption enhancer in the at least two unit dosage forms described herein is at least about 0.2 mg. In some embodiments, the total amount of absorption enhancer in the at least two unit dosage forms described herein is at least about 0.3 mg. In some embodiments, the total amount of absorption enhancer in the at least two unit dosage forms described herein is at least about 0.4 mg. In some embodiments, the total amount of absorption enhancer in the at least two unit dosage forms described herein is at least about 0.6 mg. In some embodiments, the total amount of absorption enhancer in the at least two unit dosage forms described herein is at least about 0.8 mg. In some embodiments, the total amount of absorption enhancer in the at least two unit dosage forms described herein is at least about 1 mg. In some embodiments, the total amount of absorption enhancer in the at least two unit dosage forms described herein is at least about 1.5 mg. In some embodiments, the total amount of absorption enhancer in the at least two unit dosage forms described herein is at least about 2 mg. In some embodiments, the total amount of absorption enhancer in the at least two unit dosage forms described herein is at least about 2.5 mg. In some embodiments, the total amount of absorption enhancer in the at least two unit dosage forms described herein is at least about 3 mg. In some embodiments, the total amount of absorption enhancer in the at least two unit dosage forms described herein is at least about 5 mg. In some embodiments, the total amount of absorption enhancer in the at least two unit dosage forms described herein is at least about 7 mg. In some embodiments, the total amount of absorption enhancer in the at least two unit dosage forms described herein is at least about 10 mg. In some embodiments, the total amount of absorption enhancer in the at least two unit dosage forms described herein is at least about 12 mg. In some embodiments, the total amount of absorption enhancer in the at least two unit dosage forms described herein is at least about 15 mg. In some embodiments, the total amount of absorption enhancer in the at least two unit dosage forms described herein is at least about 20 mg. In some embodiments, the total amount of absorption enhancer in the at least two unit dosage forms described herein is at least about 30 mg. In some embodiments, the total amount of absorption enhancer in the at least two unit dosage forms described herein is at least about 50 mg. In some embodiments, the total amount of absorption enhancer in the at least two unit dosage forms described herein is at least about 70 mg. In some embodiments, the total amount of absorption enhancer in the at least two unit dosage forms described herein is at least about 100 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 0.1 to 1 mg. In some embodiments, the total amount of absorption enhancer in the at least two unit dosage forms described herein is in a range of from 0.2 to 1 mg. In some embodiments, the total amount of absorption enhancer in the at least two unit dosage forms described herein is in a range of from 0.3 to 1 mg. In some embodiments, the total amount of absorption enhancer in the at least two unit dosage forms described herein is in a range of from 0.5 to 1 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 0.1 to 2 mg. In some embodiments, the total amount of absorption enhancer in the at least two unit dosage forms described herein is in a range of from 0.2 to 2 mg. In some embodiments, the total amount of absorption enhancer in the at least two unit dosage forms described herein is in a range of from 0.3 to 2 mg. In some embodiments, the total amount of absorption enhancer in the at least two unit dosage forms described herein is in a range of from 0.5 to 2 mg. In some embodiments, the total amount of absorption enhancer in the at least two unit dosage forms described herein is in a range of from 1 to 2 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 1 to 10 mg. In some embodiments, the total amount of absorption enhancer in the at least two unit dosage forms described herein is in a range of from 2 to 10 mg. In some embodiments, the total amount of absorption enhancer in the at least two unit dosage forms described herein is in a range of from 3 to 10 mg. In some embodiments, the total amount of absorption enhancer in the at least two unit dosage forms described herein is in a range of from 5 to 10 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 1 to 20 mg. In some embodiments, the total amount of absorption enhancer in the at least two unit dosage forms described herein is in a range of from 2 to 20 mg. In some embodiments, the total amount of absorption enhancer in the at least two unit dosage forms described herein is in a range of from 3 to 20 mg. In some embodiments, the total amount of absorption enhancer in the at least two unit dosage forms described herein is in a range of from 5 to 20 mg. In some embodiments, the total amount of absorption enhancer in the at least two unit dosage forms described herein is in a range of from 10 to 20 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 10 to 100 mg. In some embodiments, the total amount of absorption enhancer in the at least two unit dosage forms described herein is in a range of from 20 to 100 mg. In some embodiments, the total amount of absorption enhancer in the at least two unit dosage forms described herein is in a range of from 30 to 100 mg. In some embodiments, the total amount of absorption enhancer in the at least two unit dosage forms described herein is in a range of from 50 to 100 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 10 to 200 mg. In some embodiments, the total amount of absorption enhancer in the at least two unit dosage forms described herein is in a range of from 20 to 200 mg. In some embodiments, the total amount of absorption enhancer in the at least two unit dosage forms described herein is in a range of from 30 to 200 mg. In some embodiments, the total amount of absorption enhancer in the at least two unit dosage forms described herein is in a range of from 50 to 200 mg. In some embodiments, the total amount of absorption enhancer in the at least two unit dosage forms described herein is in a range of from 100 to 200 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 10 to 500 mg. In some embodiments, the total amount of absorption enhancer in the at least two unit dosage forms described herein is in a range of from 20 to 500 mg. In some embodiments, the total amount of absorption enhancer in the at least two unit dosage forms described herein is in a range of from 30 to 500 mg. In some embodiments, the total amount of absorption enhancer in the at least two unit dosage forms described herein is in a range of from 50 to 500 mg. In some embodiments, the total amount of absorption enhancer in the at least two unit dosage forms described herein is in a range of from 100 to 500 mg. In some embodiments, the total amount of absorption enhancer in the at least two unit dosage forms described herein is in a range of from 200 to 500 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 10 to 1000 mg. In some embodiments, the total amount of absorption enhancer in the at least two unit dosage forms described herein is in a range of from 20 to 1000 mg. In some embodiments, the total amount of absorption enhancer in the at least two unit dosage forms described herein is in a range of from 30 to 1000 mg. In some embodiments, the total amount of absorption enhancer in the at least two unit dosage forms described herein is in a range of from 50 to 1000 mg. In some embodiments, the total amount of absorption enhancer in the at least two unit dosage forms described herein is in a range of from 100 to 1000 mg. In some embodiments, the total amount of absorption enhancer in the at least two unit dosage forms described herein is in a range of from 200 to 1000 mg. In some embodiments, the total amount of absorption enhancer in the at least two unit dosage forms described herein is in a range of from 500 to 1000 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the total amount of absorption enhancer in the at least two unit dosage forms described herein is in a range of from 10 to 2000 mg. In some embodiments, the total amount of absorption enhancer in the at least two unit dosage forms described herein is in a range of from 20 to 2000 mg. In some embodiments, the total amount of absorption enhancer in the at least two unit dosage forms described herein is in a range of from 30 to 2000 mg. In some embodiments, the total amount of absorption enhancer in the at least two unit dosage forms described herein is in a range of from 50 to 2000 mg. In some embodiments, the total amount of absorption enhancer in the at least two unit dosage forms described herein is in a range of from 100 to 2000 mg. In some embodiments, the total amount of absorption enhancer in the at least two unit dosage forms described herein is in a range of from 200 to 2000 mg. In some embodiments, the total amount of absorption enhancer in the at least two unit dosage forms described herein is in a range of from 500 to 2000 mg. In some embodiments, the total amount of absorption enhancer in the at least two unit dosage forms described herein is in a range of from 1000 to 2000 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is at least about 0.01 mg. In some embodiments, the amount of absorption enhancer in each unit dosage form described herein is at least about 0.02 mg. In some embodiments, the amount of absorption enhancer in each unit dosage form described herein is at least about 0.03 mg. In some embodiments, the amount of absorption enhancer in each unit dosage form described herein is at least about 0.04 mg. In some embodiments, the amount of absorption enhancer in each unit dosage form described herein is at least about 0.06 mg. In some embodiments, the amount of absorption enhancer in each unit dosage form described herein is at least about 0.08 mg. In some embodiments, the amount of absorption enhancer in each unit dosage form described herein is at least about 0.1 mg. In some embodiments, the amount of absorption enhancer in each unit dosage form described herein is at least about 0.15 mg. In some embodiments, the amount of absorption enhancer in each unit dosage form described herein is at least about 0.2 mg. In some embodiments, the amount of absorption enhancer in each unit dosage form described herein is at least about 0.25 mg. In some embodiments, the amount of absorption enhancer in each unit dosage form described herein is at least about 0.3 mg. In some embodiments, the amount of absorption enhancer in each unit dosage form described herein is at least about 0.5 mg. In some embodiments, the amount of absorption enhancer in each unit dosage form described herein is at least about 0.7 mg. In some embodiments, the amount of absorption enhancer in each unit dosage form described herein is at least about 1 mg. In some embodiments, the amount of absorption enhancer in each unit dosage form described herein is at least about 1.2 mg. In some embodiments, the amount of absorption enhancer in each unit dosage form described herein is at least about 1.5 mg. In some embodiments, the amount of absorption enhancer in each unit dosage form described herein is at least about 2 mg. In some embodiments, the amount of absorption enhancer in each unit dosage form described herein is at least about 3 mg. In some embodiments, the amount of absorption enhancer in each unit dosage form described herein is at least about 5 mg. In some embodiments, the amount of absorption enhancer in each unit dosage form described herein is at least about 7 mg. In some embodiments, the amount of absorption enhancer in each unit dosage form described herein is at least about 10 mg. In some embodiments, the amount of absorption enhancer in each unit dosage form described herein is at least about 20 mg. In some embodiments, the amount of absorption enhancer in each unit dosage form described herein is at least about 30 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 0.01 to 0.1 mg. In some embodiments, the amount of absorption enhancer in each unit dosage form described herein is in a range of from 0.02 to 0.1 mg. In some embodiments, the amount of absorption enhancer in each unit dosage form described herein is in a range of from 0.03 to 0.1 mg. In some embodiments, the amount of absorption enhancer in each unit dosage form described herein is in a range of from 0.05 to 0.1 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 0.01 to 0.2 mg. In some embodiments, the amount of absorption enhancer in each unit dosage form described herein is in a range of from 0.02 to 0.2 mg. In some embodiments, the amount of absorption enhancer in each unit dosage form described herein is in a range of from 0.03 to 0.2 mg. In some embodiments, the amount of absorption enhancer in each unit dosage form described herein is in a range of from 0.05 to 0.2 mg. In some embodiments, the amount of absorption enhancer in each unit dosage form described herein is in a range of from 0.1 to 0.2 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 0.1 to 1 mg. In some embodiments, the amount of absorption enhancer in each unit dosage form described herein is in a range of from 0.2 to 1 mg. In some embodiments, the amount of absorption enhancer in each unit dosage form described herein is in a range of from 0.3 to 1 mg. In some embodiments, the amount of absorption enhancer in each unit dosage form described herein is in a range of from 0.5 to 1 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 0.1 to 2 mg. In some embodiments, the amount of absorption enhancer in each unit dosage form described herein is in a range of from 0.2 to 2 mg. In some embodiments, the amount of absorption enhancer in each unit dosage form described herein is in a range of from 0.3 to 2 mg. In some embodiments, the amount of absorption enhancer in each unit dosage form described herein is in a range of from 0.5 to 2 mg. In some embodiments, the amount of absorption enhancer in each unit dosage form described herein is in a range of from 1 to 2 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 1 to 10 mg. In some embodiments, the amount of absorption enhancer in each unit dosage form described herein is in a range of from 2 to 10 mg. In some embodiments, the amount of absorption enhancer in each unit dosage form described herein is in a range of from 3 to 10 mg. In some embodiments, the amount of absorption enhancer in each unit dosage form described herein is in a range of from 5 to 10 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 1 to 20 mg. In some embodiments, the amount of absorption enhancer in each unit dosage form described herein is in a range of from 2 to 20 mg. In some embodiments, the amount of absorption enhancer in each unit dosage form described herein is in a range of from 3 to 20 mg. In some embodiments, the amount of absorption enhancer in each unit dosage form described herein is in a range of from 5 to 20 mg. In some embodiments, the amount of absorption enhancer in each unit dosage form described herein is in a range of from 10 to 20 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 1 to 50 mg. In some embodiments, the amount of absorption enhancer in each unit dosage form described herein is in a range of from 2 to 50 mg. In some embodiments, the amount of absorption enhancer in each unit dosage form described herein is in a range of from 3 to 50 mg. In some embodiments, the amount of absorption enhancer in each unit dosage form described herein is in a range of from 5 to 50 mg. In some embodiments, the amount of absorption enhancer in each unit dosage form described herein is in a range of from 10 to 50 mg. In some embodiments, the amount of absorption enhancer in each unit dosage form described herein is in a range of from 20 to 50 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 1 to 100 mg. In some embodiments, the amount of absorption enhancer in each unit dosage form described herein is in a range of from 2 to 100 mg. In some embodiments, the amount of absorption enhancer in each unit dosage form described herein is in a range of from 3 to 100 mg. In some embodiments, the amount of absorption enhancer in each unit dosage form described herein is in a range of from 5 to 100 mg. In some embodiments, the amount of absorption enhancer in each unit dosage form described herein is in a range of from 10 to 100 mg. In some embodiments, the amount of absorption enhancer in each unit dosage form described herein is in a range of from 20 to 100 mg. In some embodiments, the amount of absorption enhancer in each unit dosage form described herein is in a range of from 50 to 100 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, the amount of absorption enhancer in each unit dosage form described herein is in a range of from 1 to 300 mg. In some embodiments, the amount of absorption enhancer in each unit dosage form described herein is in a range of from 2 to 300 mg. In some embodiments, the amount of absorption enhancer in each unit dosage form described herein is in a range of from 3 to 300 mg. In some embodiments, the amount of absorption enhancer in each unit dosage form described herein is in a range of from 5 to 300 mg. In some embodiments, the amount of absorption enhancer in each unit dosage form described herein is in a range of from 10 to 300 mg. In some embodiments, the amount of absorption enhancer in each unit dosage form described herein is in a range of from 20 to 300 mg. In some embodiments, the amount of absorption enhancer in each unit dosage form described herein is in a range of from 50 to 300 mg. In some embodiments, the amount of absorption enhancer in each unit dosage form described herein is in a range of from 100 to 300 mg. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein relating to an amount of absorption enhancer in one or more unit dosage form, the amount of therapeutically active agent is in accordance with any one of the ratios of absorption enhancer to therapeutically active agent described herein. In some embodiments, the unit dosage form(s) further comprises at least one protease inhibitor in an amount which is in accordance with any one of the ratios of protease inhibitor to therapeutically active agent described herein. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to the therapeutically active agent in the at least two unit dosage forms described herein (taken together) is in a range of from 5:1 to 10:1 (absorption enhancer: therapeutically active agent). In some embodiments, the ratio is about 7.5:1. In some embodiments, the unit dosage forms described herein further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 10:1 to 20:1 (absorption enhancer:therapeutically active agent). In some embodiments, the ratio is about 15:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 20:1 to 30:1 (absorption enhancer:therapeutically active agent). In some embodiments, the ratio is about 25:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 30:1 to 50:1 (absorption enhancer:therapeutically active agent). In some embodiments, the ratio is about 40:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 50:1 to 100:1 (absorption enhancer:therapeutically active agent). In some embodiments, the ratio is about 75:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 100:1 to 200:1 (absorption enhancer:therapeutically active agent). In some embodiments, the ratio is about 150:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 200:1 to 300:1 (absorption enhancer:therapeutically active agent). In some embodiments, the ratio is about 250:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 300:1 to 500:1 (absorption enhancer:therapeutically active agent). In some embodiments, the ratio is about 400:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In some embodiments of any one of the embodiments described herein, a weight ratio of absorption enhancer to therapeutically active agent in the at least two unit dosage forms described herein (taken together) is in a range of from 500:1 to 1000:1 (absorption enhancer:therapeutically active agent). In some embodiments, the ratio is about 750:1. In some embodiments, the dosage forms further comprise a protease inhibitor. In some of the aforementioned embodiments wherein the dosage forms comprise a protease inhibitor, a weight ratio of protease inhibitor to therapeutically active agent in the at least two unit dosage forms described herein (taken together) is in a range of from 1:1 to 5:1 (protease inhibitor:therapeutically active agent), optionally about 3:1. In some embodiments, a weight ratio of protease inhibitor to therapeutically active agent in the at least two unit dosage forms described herein (taken together) is in a range of from 5:1 to 10:1, optionally about 7.5:1. In some embodiments, a weight ratio of protease inhibitor to therapeutically active agent in the at least two unit dosage forms described herein (taken together) is in a range of from 10:1 to 20:1, optionally about 15:1. In some embodiments, a weight ratio of protease inhibitor to therapeutically active agent in the at least two unit dosage forms described herein (taken together) is in a range of from 20:1 to 30:1, optionally about 25:1. In some embodiments, a weight ratio of protease inhibitor to therapeutically active agent in the at least two unit dosage forms described herein (taken together) is in a range of from 30:1 to 40:1, optionally about 35:1. In some embodiments, a weight ratio of protease inhibitor to therapeutically active agent in the at least two unit dosage forms described herein (taken together) is in a range of from 40:1 to 50:1, optionally about 45:1. In some embodiments, a weight ratio of protease inhibitor to therapeutically active agent in the at least two unit dosage forms described herein (taken together) is in a range of from 50:1 to 75:1, optionally about 62.5:1. In some embodiments, a weight ratio of protease inhibitor to therapeutically active agent in the at least two unit dosage forms described herein (taken together) is in a range of from 75:1 to 100:1, optionally about 87.5:1. In some embodiments, a weight ratio of protease inhibitor to therapeutically active agent in the at least two unit dosage forms described herein (taken together) is in a range of from 100:1 to 200:1, optionally about 150:1. In some embodiments, a weight ratio of protease inhibitor to therapeutically active agent in the at least two unit dosage forms described herein (taken together) is in a range of from 200:1 to 300:1, optionally about 250:1. In some embodiments, a weight ratio of protease inhibitor to therapeutically active agent in the at least two unit dosage forms described herein (taken together) is in a range of from 300:1 to 400:1, optionally about 350:1. In some embodiments, a weight ratio of protease inhibitor to therapeutically active agent in the at least two unit dosage forms described herein (taken together) is in a range of from 400:1 to 500:1, optionally about 450:1. In some embodiments, the protease inhibitor is soybean trypsin inhibitor. In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

Therapeutically Active Agent:

In some embodiments of any one of the embodiments described herein, the at least two unit dosage forms according to any one of the aspects described herein together comprise at least 50 μg of therapeutically active agent. In some embodiments, the at least two unit dosage forms together comprise at least 100 μg of therapeutically active agent. In some embodiments, the at least two unit dosage forms together comprise at least 200 μg of therapeutically active agent. In some embodiments, the at least two unit dosage forms together comprise at least 500 μg of therapeutically active agent. In some embodiments, the amount of absorption enhancer in the unit dosage forms is in accordance with any one of the ratios of absorption enhancer to therapeutically active agent described herein. In some embodiments, the absorption enhancer is NAC (8-N-(2-hydroxybenzoyl)aminocaprylic acid) or a salt thereof (e.g., sodium 8-N-(2-hydroxybenzoyl)aminocaprylate). In some embodiments, the unit dosage forms further comprise at least one protease inhibitor in an amount which is in accordance with any one of the ratios of protease inhibitor to therapeutically active agent described herein.

In some embodiments of any one of the embodiments described herein, the at least two unit dosage forms according to any one of the aspects described herein together comprise 2000 μg or less of therapeutically active agent. In some embodiments, the at least two unit dosage forms together comprise 1000 μg or less of therapeutically active agent. In some embodiments, the amount of absorption enhancer in the unit dosage forms is in accordance with any one of the ratios of absorption enhancer to therapeutically active agent described herein. In some embodiments, the absorption enhancer is NAC (8-N-(2-hydroxybenzoyl)aminocaprylic acid) or a salt thereof (e.g., sodium 8-N-(2-hydroxybenzoyl)aminocaprylate). In some embodiments, the unit dosage forms further comprise at least one protease inhibitor in an amount which is in accordance with any one of the ratios of protease inhibitor to therapeutically active agent described herein.

In some embodiments of any one of the embodiments described herein, the at least two unit dosage forms together comprise from 100 to 3000 μg of therapeutically active agent. In some embodiments, the at least two unit dosage forms together comprise from 200 to 2000 μg of therapeutically active agent. In some embodiments, the at least two unit dosage forms together comprise from 500 to 1000 μg of therapeutically active agent. In some embodiments, the at least two unit dosage forms together comprise about 750 μg of therapeutically active agent. In some embodiments, the at least two unit dosage forms together comprise from 1000 to 3000 μg of therapeutically active agent. In some embodiments, the at least two unit dosage forms together comprise from 1500 to 2500 μg of therapeutically active agent. In some embodiments, the at least two unit dosage forms together comprise about 2000 μg of therapeutically active agent. In some embodiments, the therapeutically active agent is a parathyroid hormone or a fragment thereof. In some embodiments, the therapeutically active agent is teriparatide. In some embodiments, the amount of absorption enhancer in the unit dosage forms is in accordance with any one of the ratios of absorption enhancer to therapeutically active agent described herein. In some embodiments, the absorption enhancer is NAC (8-N-(2-hydroxybenzoyl)aminocaprylic acid) or a salt thereof (e.g., sodium 8-N-(2-hydroxybenzoyl)aminocaprylate). In some embodiments, the unit dosage forms further comprise at least one protease inhibitor in an amount which is in accordance with any one of the ratios of protease inhibitor to therapeutically active agent described herein.

In some embodiments of any one of the embodiments described herein, each unit dosage form according to any one of the aspects described herein comprises at least 5 μg of therapeutically active agent. In some embodiments, each unit dosage form comprises at least 10 μg of therapeutically active agent. In some embodiments, each unit dosage form comprises at least 20 μg of therapeutically active agent. In some embodiments, each unit dosage form comprises at least 50 μg of therapeutically active agent. In some embodiments, each unit dosage form comprises at least 100 μg of therapeutically active agent. In some embodiments, each unit dosage form comprises at least 200 μg of therapeutically active agent. In some embodiments, the amount of absorption enhancer in each unit dosage form is in accordance with any one of the ratios of absorption enhancer to therapeutically active agent described herein. In some embodiments, the absorption enhancer is NAC (8-N-(2-hydroxybenzoyl) aminocaprylic acid) or a salt thereof (e.g., sodium 8-N-(2-hydroxybenzoyl)aminocaprylate). In some embodiments, each unit dosage forms further comprises at least one protease inhibitor in an amount which is in accordance with any one of the ratios of protease inhibitor to therapeutically active agent described herein.

In some embodiments of any one of the embodiments described herein, each unit dosage forms according to any one of the aspects described herein comprises 1000 μg or less of therapeutically active agent. In some embodiments, each unit dosage form comprises 500 μg or less of therapeutically active agent. In some embodiments, the amount of absorption enhancer in each unit dosage form is in accordance with any one of the ratios of absorption enhancer to therapeutically active agent described herein. In some embodiments, the absorption enhancer is NAC (8-N-(2-hydroxybenzoyl)aminocaprylic acid) or a salt thereof (e.g., sodium 8-N-(2-hydroxybenzoyl)aminocaprylate). In some embodiments, each unit dosage form further comprises at least one protease inhibitor in an amount which is in accordance with any one of the ratios of protease inhibitor to therapeutically active agent described herein.

In some embodiments of any one of the embodiments described herein, each unit dosage form comprises from 10 to 1000 μg of therapeutically active agent. In some embodiments, each unit dosage form comprises from 20 to 1000 μg of therapeutically active agent. In some embodiments, each unit dosage form comprises from 50 to 1000 μg of therapeutically active agent. In some embodiments, each unit dosage form comprises from 100 to 750 μg of therapeutically active agent. In some embodiments, each unit dosage form comprises about 500 μg of therapeutically active agent. In some embodiments, the therapeutically active agent is a parathyroid hormone or a fragment thereof. In some embodiments, the therapeutically active agent is teriparatide. In some embodiments, the amount of absorption enhancer in each unit dosage form is in accordance with any one of the ratios of absorption enhancer to therapeutically active agent described herein. In some embodiments, the absorption enhancer is NAC (8-N-(2-hydroxybenzoyl)aminocaprylic acid) or a salt thereof (e.g., sodium 8-N-(2-hydroxybenzoyl) aminocaprylate). In some embodiments, each unit dosage form further comprises at least one protease inhibitor in an amount which is in accordance with any one of the ratios of protease inhibitor to therapeutically active agent described herein.

According to an aspect of some embodiments of the invention, there is provided a pharmaceutical composition unit dosage form comprising less than 200 μg of a parathyroid hormone or a fragment thereof (e.g., teriparatide), and an absorption enhancer according to any of the respective embodiments described herein (e.g., NAC or a salt thereof).

In some such embodiments, the unit dosage form comprises less than 100 μg of a parathyroid hormone or a fragment thereof.

Unit dosage forms comprising less than 200 μg of a parathyroid hormone or a fragment thereof have no significant effect on a normal body when administered per se, yet such unit dosage forms can be advantageous when administered concomitantly according to any of the respective embodiments described herein.

In some such embodiments of any of the embodiments described herein relating to a unit dosage form comprising less than 200 μg of a parathyroid hormone or a fragment thereof, the unit dosage form comprises at least 5 μg of parathyroid hormone or a fragment thereof, optionally at least 10 μg, optionally at least 20 μg, optionally at least 50 μg, and optionally at least 100 μg of parathyroid hormone or a fragment thereof.

Compositions described herein are particularly suitable for enhancing the absorption of therapeutically active agents whose absorption upon oral administration is limited, for example, by a large molecular weight, strong hydrophilicity (e.g., which inhibits crossing of lipid membranes in the gastrointestinal tract), and/or degradation in the gastrointestinal tract (e.g., by proteolysis).

In some embodiments of any one of the embodiments described herein, the therapeutically active agent included in any of the compositions (including composition unit dosage forms) described herein has a molecular weight of at least 0.5 kDa. In some embodiments, the molecular weight is in a range of from 0.5 to 150 kDa. In some embodiments, the molecular weight is in a range of from 0.5 to 100 kDa. In some embodiments, the molecular weight is in a range of from 0.5 to 75 kDa. In some embodiments, the molecular weight is in a range of from 0.5 to 50 kDa. In some embodiments, the molecular weight is in a range of from 0.5 to 30 kDa. In some embodiments, the molecular weight is in a range of from 0.5 to 20 kDa. In some embodiments, the molecular weight is in a range of from 0.5 to 10 kDa. In some embodiments, the molecular weight is in a range of from 0.5 to 7.5 kDa. In some embodiments, the molecular weight is in a range of from 0.5 to 5 kDa.

In some embodiments of any one of the embodiments described herein, the therapeutically active agent has a molecular weight of at least 1 kDa. In some embodiments, the molecular weight is in a range of from 1 to 150 kDa. In some embodiments, the molecular weight is in a range of from 1 to 100 kDa. In some embodiments, the molecular weight is in a range of from 1 to 75 kDa. In some embodiments, the molecular weight is in a range of from 1 to 50 kDa. In some embodiments, the molecular weight is in a range of from 1 to 30 kDa. In some embodiments, the molecular weight is in a range of from 1 to 20 kDa. In some embodiments, the molecular weight is in a range of from 1 to 10 kDa. In some embodiments, the molecular weight is in a range of from 1 to 7.5 kDa. In some embodiments, the molecular weight is in a range of from 1 to 5 kDa.

In some embodiments of any one of the embodiments described herein, the therapeutically active agent has a molecular weight of at least 2 kDa. In some embodiments, the molecular weight is in a range of from 2 to 150 kDa. In some embodiments, the molecular weight is in a range of from 2 to 100 kDa. In some embodiments, the molecular weight is in a range of from 2 to 75 kDa. In some embodiments, the molecular weight is in a range of from 2 to 50 kDa. In some embodiments, the molecular weight is in a range of from 2 to 30 kDa. In some embodiments, the molecular weight is in a range of from 2 to 20 kDa. In some embodiments, the molecular weight is in a range of from 2 to 10 kDa. In some embodiments, the molecular weight is in a range of from 2 to 7.5 kDa. In some embodiments, the molecular weight is in a range of from 2 to 5 kDa.

In some embodiments of any one of the embodiments described herein, the therapeutically active agent has a molecular weight of at least 3 kDa. In some embodiments, the molecular weight is in a range of from 3 to 150 kDa. In some embodiments, the molecular weight is in a range of from 3 to 100 kDa. In some embodiments, the molecular weight is in a range of from 3 to 75 kDa. In some embodiments, the molecular weight is in a range of from 3 to 50 kDa. In some embodiments, the molecular weight is in a range of from 3 to 30 kDa. In some embodiments, the molecular weight is in a range of from 3 to 20 kDa. In some embodiments, the molecular weight is in a range of from 3 to 10 kDa. In some embodiments, the molecular weight is in a range of from 3 to 7.5 kDa. In some embodiments, the molecular weight is in a range of from 3 to 5 kDa.

In some embodiments of any one of the embodiments described herein, the therapeutically active agent has a molecular weight of at least 4 kDa. In some embodiments, the molecular weight is in a range of from 4 to 150 kDa. In some embodiments, the molecular weight is in a range of from 4 to 100 kDa. In some embodiments, the molecular weight is in a range of from 4 to 75 kDa. In some embodiments, the molecular weight is in a range of from 4 to 50 kDa. In some embodiments, the molecular weight is in a range of from 4 to 30 kDa. In some embodiments, the molecular weight is in a range of from 4 to 20 kDa. In some embodiments, the molecular weight is in a range of from 4 to 10 kDa. In some embodiments, the molecular weight is in a range of from 4 to 7.5 kDa. In some embodiments, the molecular weight is in a range of from 4 to 5 kDa.

In some embodiments of any one of the embodiments described herein, the therapeutically active agent has a molecular weight of at least 5 kDa. In some embodiments, the molecular weight is in a range of from 5 to 150 kDa. In some embodiments, the molecular weight is in a range of from 5 to 100 kDa. In some embodiments, the molecular weight is in a range of from 5 to 75 kDa. In some embodiments, the molecular weight is in a range of from 5 to 50 kDa. In some embodiments, the molecular weight is in a range of from 5 to 30 kDa. In some embodiments, the molecular weight is in a range of from 5 to 20 kDa. In some embodiments, the molecular weight is in a range of from 5 to 10 kDa. In some embodiments, the molecular weight is in a range of from 5 to 7.5 kDa.

In some embodiments of any one of the embodiments described herein, the therapeutically active agent has a molecular weight of at least 10 kDa. In some embodiments, the molecular weight is in a range of from 10 to 150 kDa. In some embodiments, the molecular weight is in a range of from 10 to 100 kDa. In some embodiments, the molecular weight is in a range of from 10 to 75 kDa. In some embodiments, the molecular weight is in a range of from 10 to 50 kDa. In some embodiments, the molecular weight is in a range of from 10 to 30 kDa. In some embodiments, the molecular weight is in a range of from 10 to 20 kDa.

In some embodiments of any one of the embodiments described herein, the therapeutically active agent has a molecular weight of at least 20 kDa. In some embodiments, the molecular weight is in a range of from 20 to 150 kDa. In some embodiments, the molecular weight is in a range of from 20 to 100 kDa. In some embodiments, the molecular weight is in a range of from 20 to 75 kDa. In some embodiments, the molecular weight is in a range of from 20 to 50 kDa. In some embodiments, the molecular weight is in a range of from 20 to 30 kDa.

In some embodiments of any one of the embodiments described herein, the therapeutically active agent has a molecular weight of at least 50 kDa. In some embodiments, the molecular weight is in a range of from 50 to 150 kDa. In some embodiments, the molecular weight is in a range of from 50 to 100 kDa. In some embodiments, the molecular weight is in a range of from 50 to 75 kDa.

Without being bound by any particular theory, it is believed that agents having a relatively high molecular weight (e.g., at least 0.5 kDa, at least 1 kDa, at least 2 kDa, at least 3 kDa, at least 4 kDa) tend to be less efficiently absorbed upon oral administration than relatively small molecules (e.g., molecules having a molecular weight of less than 0.5 kDa, or less than 1 kDa) and therefore, their absorption is particularly susceptible to enhancement by activity of an absorption enhancer (e.g., NAC or a salt thereof) according to any of the respective embodiments described herein.

In some embodiments of any one of the embodiments described herein, the therapeutically active agent included in any of the compositions (including composition unit dosage forms) described herein is a hormone and/or cytokine (e.g., a hormone). In some embodiments, the polypeptide is a polypeptide hormone and/or cytokine, or a fragment thereof (e.g., a fragment exhibiting an activity of the hormone and/or cytokine), or a homolog of a polypeptide hormone and/or cytokine or fragment thereof.

Examples of polypeptides which may be utilized (per se or as fragments thereof and/or homologs thereof) as therapeutically active agents according to embodiments of the invention include, without limitation, insulin, a glucagon, a parathyroid hormone, an interferon, a growth hormone, an erythropoietin, a calcitonin, an omentin, a motilin, a leptin, a peptide YY, a GLP-1 (glucagon-like peptide-1), a GLP-2 (glucagon-like peptide-2), granulocyte-colony stimulating factor (G-CSF), an antibody (e.g., monoclonal antibody), an interleukin, an erythropoietin, a vasopressin, a vasoactive intestinal peptide, a pituitary adenylate cyclase-activating peptide (PACAP), a blood clotting factor, an endomorphin (e.g., endomorphin-1, endomorphin-2), a TNF inhibitor (e.g., infliximab, adalimumab, certolizumab, golimumab, etanercept), disitertide, octreotide (a somatotropin analog), davunetide, icatibant, glucocerebrosidase, a gonadotropin releasing hormone (GnRH), acyline (a GnRH antagonist), and a GLP-1 agonist such as exendin-4 (including exenatide and lixisenatide). Examples of growth hormones, include, without limitation, somatotropin (growth hormone 1), growth hormone 2, and growth factors (e.g., insulin-like growth factor 1 (IGF-1), fibroblast growth factor (FGF), ciliary neurotrophic factor).

Insulin, glucagon, parathyroid hormone, erythropoietin, calcitonin, motilin, leptin, peptide YY, GLP-1 (including derivatives thereof such as liraglutide, taspoglutide, albiglutide and dulaglutide), GLP-2, GnRH (including derivatives thereof such as leuprorelin, buserelin, histrelin, goserelin, deslorelin, nafarelin and triptorelin), vasopressin (including derivatives thereof such as desmopressin), vasoactive intestinal peptide (including aviptadil), pituitary adenylate cyclase-activating peptide (PACAP), growth hormones (including axokine, a homolog of a fragment of ciliary neurotrophic factor) and G-CSF are non-limiting examples of polypeptide hormones.

Interferons, interleukins, erythropoietin and analogs thereof (e.g., darbepoetin), omentin and G-CSF are non-limiting examples of polypeptide cytokines.

In some embodiments of any one of the embodiments described herein, the therapeutically active agent is parathyroid hormone (PTH) or a fragment thereof.

Herein, the term "parathyroid hormone" or its abbreviation "PTH" encompasses parathyroid hormone (having a naturally occurring amino acid sequence, e.g., an 84-amino acid sequence in humans) and homologs of the parathyroid hormone. A "fragment" of parathyroid hormone encompasses fragments of parathyroid hormone having a naturally occurring amino acid sequence (e.g., in humans) and homologs of such fragments. Preferably, the fragment is a fragment which exhibits a biological activity of parathyroid hormone.

Teriparatide is an example of a parathyroid hormone fragment, composed of amino acids 1-34 (i.e., an N-terminal portion) of the full parathyroid hormone polypeptide. The term "teriparatide" is used interchangeably herein with the terms "PTH(1-34)" and "parathyroid hormone(1-34)".

Herein, for the sake of brevity, the term "parathyroid hormone" or its abbreviation "PTH" encompasses parathyroid hormone (having a naturally occurring amino acid sequence, e.g., in humans), fragments thereof and homologs of the parathyroid hormone or the fragment thereof, except where indicated otherwise.

Without being bound by any particular theory, it is believed that agents which are polypeptides tend to be poorly absorbed upon oral administration, for example, due to their polarity and/or relatively large molecular weight; and therefore, their absorption is particularly susceptible to enhancement by activity of an absorption enhancer (e.g., NAC or a salt thereof) according to any of the respective embodiments described herein.

In some embodiments of any one of the embodiments described herein wherein the therapeutically active agents is a polypeptide, the composition further comprises at least one protease inhibitor, for example, according to any one of the embodiments described herein relating to a protease inhibitor.

It has been reported that therapeutically active agents which exhibit more than one of the following criteria tend to be poorly absorbed upon oral administration (when administered alone), a phenomenon referred to in the art as "Lipinski's rule of 5":

(i) a total number of nitrogen-hydrogen bonds and oxygen hydrogen bonds (which are typically hydrogen bond donors) which is more than 5;
(ii) a total number of nitrogen and oxygen atoms (which are typically hydrogen bond acceptors) which is more than 5;
(iii) an octanol-water partition coefficient (log P) which is greater than 5; and/or
(iv) a molecular weight of at least 500 Da (0.5 kDa).

The abovementioned criteria (i) and (ii) are associated with hydrogen bonding and hydrophilicity; whereas criteria (iii) is associated with lipophilicity.

As described herein, therapeutically active agents poorly absorbed upon oral administration when administered alone are particularly suitable for being included in compositions described herein, in order to enhance their absorption.

In some embodiments of any one of the embodiments described herein, the therapeutically active agent meets at least one of the abovementioned criteria (i), (ii), (iii) and (iv). In some embodiments, the therapeutically active agent meets at least two of the abovementioned criteria (i), (ii), (iii) and (iv). In some embodiments, the therapeutically active agent meets at least three of the abovementioned criteria (i), (ii), (iii) and (iv). In some embodiments, the therapeutically active agent meets all four of the abovementioned criteria (i), (ii), (iii) and (iv).

In some embodiments of any one of the embodiments described herein, the therapeutically active agent has a molecular weight of at least 0.5 kDa, in accordance with any one of the embodiments described herein relating to a molecular weight of at least 0.5 kDa, and further meets at least one of the abovementioned criteria (i), (ii) and (iii). In some such embodiments, the therapeutically active agent meets at least two of the abovementioned criteria (i), (ii) and (iii).

Dihydroergotamine and fondaparinux are non-limiting examples of non-peptidic agents having a molecular weight of at least 0.5 kDa, which are poorly absorbed upon oral administration.

In some embodiments of any one of the embodiments described herein, the therapeutically active agent has a molecular weight of less than 0.5 kDa, and meets at least one of the abovementioned criteria (i), (ii) and (iii). In some such embodiments, the therapeutically active agent meets at least two of the abovementioned criteria (i), (ii) and (iii). In some such embodiments, the therapeutically active agent meets all three of the abovementioned criteria (i), (ii) and (iii).

In addition, ionic molecules tend to be poorly absorbed upon oral administration, generally due to a considerably reduced ability to cross lipid membranes. Whether a molecule is ionic or non-ionic often depends on pH, which varies according to location in the gastrointestinal tract. In general, it is believed that the more a therapeutically active agent is in ionic form in the gastrointestinal tract, the more likely it is to be poorly absorbed upon oral administration.

In some embodiments of any one of the embodiments described herein, the therapeutically active agent is ionic in an aqueous solution at a pH of 7.0.

In some embodiments of any one of the embodiments described herein, the therapeutically active agent is ionic in an aqueous solution at a pH of 6.0.

In some embodiments of any one of the embodiments described herein, the therapeutically active agent is ionic in an aqueous solution at a pH of 5.0.

In some embodiments of any one of the embodiments described herein, the therapeutically active agent is ionic in an aqueous solution at a pH of 4.0.

In some embodiments of any one of the embodiments described herein, the therapeutically active agent is ionic in an aqueous solution at a pH of 3.0.

In some embodiments of any one of the embodiments described herein, the therapeutically active agent is ionic in an aqueous solution at a pH of 2.0.

In some embodiments of any one of the embodiments described herein, the therapeutically active agent is ionic in an aqueous solution at a pH of 1.0.

Examples of such agents include, without limitation, compounds comprising at least one basic group (e.g., amine group) which is positively charged at a pH of 7.0 (or less).

Herein, a compound is considered "ionic" when it comprises at least one functional group which is charged in at least 50% of the molecules in a population of molecules of the compound under designated conditions (e.g., in an aqueous solution at a designated pH value or range of pH values). The skilled person will be readily capable of determining whether a functional group is charged in at least 50% of the molecules, for example, by determining a pKa value associated with the functional group. An ionic compound, as defined herein, may optionally have a net negative charge, optionally a net positive charge, and optionally an equal number of negatively charged functional groups and positively functional groups, resulting in no net charge.

In some embodiments of any one of the embodiments described herein, the therapeutically active agent is ionic in an aqueous solution at all pH values within a range of from 5.0 to 7.0. In some embodiments, the therapeutically active agent is ionic in an aqueous solution at all pH values within a range of from 5.0 to 8.0. In some embodiments, the therapeutically active agent is ionic in an aqueous solution at all pH values within a range of from 4.0 to 9.0. In some embodiments, the therapeutically active agent is ionic in an aqueous solution at all pH values within a range of from 3.0 to 10.0. In some embodiments, the therapeutically active agent is ionic in an aqueous solution at all pH values within a range of from 2.0 to 11.0.

In some embodiments of any one of the embodiments described herein, the therapeutically active agent is ionic at a pH value and/or range according to any one of the abovementioned embodiments, and further has a molecular weight of at least 0.5 kDa, in accordance with any one of the embodiments described herein relating to a molecular weight of at least 0.5 kDa.

In some embodiments of any one of the embodiments described herein, the therapeutically active agent is ionic at a pH value and/or range according to any one of the abovementioned embodiments, and further has a molecular weight of less than 0.5 kDa.

Examples of ionic therapeutically active agents which tend to have a molecular weight of less than 0.5 kDa, and which tend to exhibit poor absorption upon oral administration, include, without limitation, bisphosphonates (e.g., for use in treating osteoporosis and related conditions) such as alendronate, clodronate, etidronate, ibandronate, neridronate, olpadronate, pamidronate, risedronate, tiludronate and zoledronate; and cromolyn (e.g., cromolyn sodium).

In some embodiments of any one of the embodiments described herein, the therapeutically active agent is a Class III agent according to the Biopharmaceutics Classification System (BCS), as provided by the U.S. FDA, that is, the therapeutically active agent is characterized by low permeability and high solubility.

In the context of the BCS, the phrase "low permeability" refers herein and in the art to absorption of less than 90% of a given agent upon oral administration in humans (in the absence of absorption enhancer), as determined by mass-balance determination and/or in comparison to an intravenous dose.

In some embodiments, absorption of a Class III therapeutically active agent is less than 50% upon oral administration (in the absence of absorption enhancer). In some embodiments, absorption is less than 20% upon oral administration (in the absence of absorption enhancer). In some embodiments, absorption is less than 10% upon oral administration (in the absence of absorption enhancer). In some embodiments, absorption is less than 5% upon oral administration (in the absence of absorption enhancer). In some embodiments, absorption is less than 2% upon oral administration (in the absence of absorption enhancer). In some embodiments, absorption is less than 1% upon oral administration (in the absence of absorption enhancer). In some of the aforementioned embodiments, the absorption enhancer is NAC (8-N-(2-hydroxybenzoyl)aminocaprylic acid) or a salt thereof (e.g., sodium 8-N-(2-hydroxybenzoyl)aminocaprylate).

In the context of the BCS, the phrase "high solubility" refers herein and in the art to an amount of therapeutically active agent in an administered dose being soluble in 250 ml or less of water over a pH range of 1 to 7.5.

The skilled person will be capable of determining which conditions are treatable by oral administration of any given therapeutically active agent described herein.

Examples of conditions treatable according to embodiments of the invention include, without limitation, hyperglycemia, for example, in diabetes (e.g., wherein the therapeutically active agent is an insulin or a GLP-1, or another agent which reduces blood glucose levels); hypoglycemia (e.g., wherein the therapeutically active agent is a glucagon, or another agent which increases blood glucose levels); osteoporosis and conditions associated with a bone fracture or bone defect (e.g., wherein the therapeutically active agent is a PTH or fragment thereof); and hypoparathyroidism (e.g., wherein the therapeutically active agent is a PTH or fragment thereof).

In the context of medical conditions associated with bone fractures, the terms "treating" and "treatment" encompass, for example, substantially healing, at least in part, a bone fracture (e.g., a fracture non-union which does not heal without intervention), substantially increasing a rate at which a bone fracture heals, substantially ameliorating or preventing the appearance of symptoms of a bone fracture (e.g., pain, loss of functionality of a portion of the body, defective bone formation), and preventing or reducing the likelihood of a bone fracture occurring, for example, due to a medical condition (e.g., prophylaxis). Treatment of a bone fracture as described herein may optionally be performed in combination with standard treatments of bone fractures, such as immobilization of bones (e.g., with a cast) and/or surgery.

Examples of conditions associated with a bone fracture include, without limitation, a fracture non-union, any medical condition associated with a stress fracture (optionally the condition is a stress fracture per se), Herein and in the art, the phrase "fracture non-union" refers to a medical condition in which a bone fracture is present, and there is no reasonable expectation that the fracture will heal without intervention.

The skilled person will be readily capable of determining a presence of a fracture non-union.

In some embodiments according to any of the aspects of embodiments relating to non-unions, a fracture non-union is determined based on non-consolidation at the fracture site 6 months after the fracture was formed, and/or based on an absence of progress in callus formation at the fracture site at 4 week intervals (e.g., as described by Giannotti et al. [*Clin Cases Miner Bone Metab* 2013, 10:116-120]).

Herein and in the art, the phrase "stress fracture" refers to a bone fracture caused by repeated stress over time (e.g., by running and/or jumping).

In some embodiments, treating a medical condition associated with a stress fracture comprises increasing a rate at which an existing stress fracture heals.

In some embodiments, treating a medical condition associated with a stress fracture comprises reducing the likelihood of a stress fracture occurring, for example, in a subject susceptible to stress fractures. Examples of subjects susceptible to stress fractures include, without limitation, athletes, runners, soldiers and other people subject to considerable physical exercise.

Herein, the phrase "bone defect" encompasses any missing portion of a bone, including, bone missing due to trauma (e.g., wherein a bone fracture results in a missing bone fragment), surgery (e.g., wherein bone is surgically removed in order to remove cancer cells), resorption of bone, an acquired medical condition (e.g., wherein an acquired medical condition causes a portion of a bone to disappear via resorption) and/or congenital conditions (e.g., wherein a congenitally misshapen bone is associated with one or more defects in the bone structure), a space between a bone and an implant intended to be osseointegrated with the bone (including, but not limited to, an implant anchored in a bone, for example, via a bolt or screw).

Examples of medical conditions involving resorption of bone include, without limitation, bone resorption associated with inflammatory conditions (e.g., periodontitis), which may comprise resorption of bone near the site of inflammation, and resorption of alveolar bone associated with a missing tooth.

Herein, the terms "osseointegration" and "osseointegrated" refer to formation of a direct structural connection (e.g., without intervening connective tissue) between living bone and an implant; and includes, but is not limited to, growth of bone into an implant (e.g., a porous implant), a process also known in the art as "osseoincorporation".

In the context of medical conditions associated with bone defects, the terms "treating" and "treatment" encompass, for example, substantially healing, at least in part, a bone defect (e.g., replacement of at least a portion of missing bone by bone regeneration), substantially increasing a rate at which a bone defect heals (e.g., a rate of bone regeneration), substantially ameliorating or preventing the appearance of symptoms of a bone defect (e.g., pain, loss of functionality of a portion of the body, defective bone formation), and preventing or reducing formation of a bone defect (e.g., prophylaxis), for example, formation of a bone defect by bone resorption. Treatment of a bone defect as described herein may optionally be performed in combination with standard treatments of the respective bone defect.

In some embodiments according to any of the aspects of embodiments described herein, the medical condition is resorption of alveolar bone. In some of these embodiments, the method or treatment is for preserving and/or regenerating alveolar bone. Examples of resorption of alveolar bone include, without limitation, resorption associated with a missing tooth and resorption associated with inflammation (e.g., periodontitis).

In some embodiments, the method or treatment is for preserving and/or regenerating alveolar bone surrounding a dental implant (e.g., a dental implant which comprises or supports a prosthetic tooth, crown, dental bridge and/or fixed denture), for example, to hold the dental implant in place, thereby increasing the utility of the implant and/or the likelihood of success of the dental implantation. In some embodiments, the method or treatment is effected following implantation of a dental implant, for example, in order to promote regeneration of alveolar bone (e.g., alveolar bone characterized by a bone defect associated with resorption of the bone due to a missing tooth and/or periodontitis). In alternative or additional embodiments, the method or treatment is effected prior to implantation of a dental implant, for example, in order to preserve alveolar bone by preventing or reducing alveolar bone resorption (e.g., upon loss of a tooth, when a significant amount of time is expected to pass before implantation of a dental implant.

In some embodiments according to any of the aspects of embodiments described herein, the bone defect is in the skull (cranium or lower jawbone). In some embodiments, the bone defect is a calvarial bone defect.

Without being bound by any particular theory, it is believed that bone in the skull (e.g., in the calvaria) is particularly susceptible to poor healing of bone defects, in which promotion of bone growth would be advantageous.

In some embodiments according to any of the aspects of embodiments described herein, the method and/or treatment comprises promoting osseointegration of an implant, for example, by promoting bone growth in a space between a bone (e.g., calvarial bone) and the implant. The medical condition may optionally be any medical condition for which osseointegration of an implant is beneficial.

Examples of implants for which osseointegration may be promoted include, without limitation, dental implants, bone grafts (e.g., bone allografts), chin implants, craniofacial prostheses (e.g., artificial ears, eyes and/or noses), bone-anchored limb prostheses, bone-anchored hearing aids, and joint prostheses (e.g., for hip and/or knee replacement).

Herein, the term "implant" refers to any device, wherein at least a portion of the device is placed in a subject, and encompasses man-made devices and transplanted tissue, and may comprise synthetic materials, an autograft (e.g., bone harvested from a different region of the subject, such as the iliac crest or chin), an allograft (e.g., bone harvested from an individual other than the subject, optionally a cadaver), a xenograft (e.g., bone from a different species, optionally bovine bone or coral) or any combination thereof. Examples of synthetic material which may be included in an implant (e.g., an implant intended to be osseointegrated) include, without limitation, hydroxylapatite, calcium carbonate, tri-calcium phosphate, polymers (e.g., poly(methyl methacrylate), poly(hydroxyethyl methacrylate)), ceramics and metals (e.g., titanium).

In some embodiments of any one of the embodiments described herein relating to treatment of osteoporosis and/or a condition associated with a bone fracture or bone defect, the concomitant oral administration according to any of the respective embodiments described herein is effected from 1 to 4 times per day. In some such embodiments, the concomitant oral administration according to any of the respective embodiments described herein is effected from 1 to 3 times per day. In some such embodiments, the concomitant oral administration according to any of the respective embodiments described herein is effected once or twice per day. In some such embodiments, the concomitant oral administration according to any of the respective embodiments described herein is effected once per day.

In some embodiments of any one of the embodiments described herein relating to treatment of a condition associated with a bone fracture or bone defect is effected once per day or less. In some such embodiments, the oral administration is effected once every two days. In some such embodiments, the oral administration is effected twice per week. In some such embodiments, the oral administration is effected once per week or less.

In some embodiments of any one of the embodiments described herein relating to oral administration once per day or less frequently, the treatment is a prophylactic treatment (for preventing or reducing the likelihood and/or size of a bone fracture and/or bone defect), that is, the subject does not necessarily have a bone fracture and/or bone defect at the time of treatment.

In some embodiments, the prophylactic treatment is for stress fractures, for example, in a subject susceptible to stress fractures (e.g., as described herein).

In some embodiments, the prophylactic treatment is for preventing or reducing an alveolar bone defect associated with resorption of alveolar bone, for example, in a subject susceptible to alveolar bone resorption (e.g., as described herein). Subjects afflicted by periodontitis and/or subjects missing a tooth are non-limiting examples of subjects susceptible to alveolar bone resorption.

Without being bound by any particular theory, it is believed that relatively low dosages (e.g., as effected by a relatively low frequency of oral administration) are more suitable than high dosages for prophylactic applications.

In some embodiments of any one of the embodiments described herein relating to treatment of hypoparathyroidism with PTH, the concomitant oral administration according to any of the respective embodiments described herein is effected at least twice per day. In some such embodiments, the concomitant oral administration according to any of the respective embodiments described herein is effected at least 3 times per day. In some such embodiments, the concomitant oral administration according to any of the respective embodiments described herein is effected at least 4 times per day.

In some embodiments of any one of the embodiments described herein relating to treatment of hypoparathyroidism with PTH, the concomitant oral administration according to any of the respective embodiments described herein is effected from 2 to 6 times per day. In some such embodiments, the concomitant oral administration according to any of the respective embodiments described herein is effected from 3 to 6 times per day. In some such embodiments, the concomitant oral administration according to any of the respective embodiments described herein is effected from 4 to 6 times per day. In some such embodiments, the concomitant oral administration according to any of the respective embodiments described herein is effected 4 times per day.

Without being bound by any particular theory, it is believed that effecting oral administration of PTH at least 3 times per day (e.g., at least 4 times per day) as described in any of the respective embodiments herein, provides a relatively steady increase in PTH levels in the body, which is advantageous in the treatment of hypoparathyroidism.

Protease Inhibitor(s):

In some embodiments of any one of the embodiments described herein, a unit dosage form according to any of the respective embodiments described herein comprises at least one protease inhibitor. In some embodiments, the at least one protease inhibitor comprises at least one trypsin inhibitor. In some embodiments, the at least one protease inhibitor consists essentially of one or more trypsin inhibitor(s).

Examples of trypsin inhibitor which may be utilized in any one of the embodiments described herein include, without limitation, lima bean trypsin inhibitor, aprotinin, soybean trypsin inhibitor, ovomucoid trypsin inhibitor and any combination thereof. In some embodiments, the at least one trypsin inhibitor comprises soybean trypsin inhibitor (SBTI). In some embodiments, the at least one trypsin inhibitor (an optionally the at least one protease inhibitor) consists essentially of SBTI.

In some embodiments of any of the embodiments described herein, the at least one protease inhibitor comprises at least one serpin. In some embodiments, the at least one protease inhibitor consists essentially of one or more serpin(s).

Examples of serpins which may be utilized in any one of the embodiments described herein, include, without limitation, alpha 1-antitrypsin, antitrypsin-related protein, alpha 1-antichymotrypsin, kallistatin, protein C inhibitor, cortisol binding globulin, thyroxine-binding globulin, angiotensinogen, centerin, protein Z-related protease inhibitor, vaspin, monocyte/neutrophil elastase inhibitor, plasminogen activator inhibitor-2, squamous cell carcinoma antigen-1 (SCCA-1), squamous cell carcinoma antigen-2 (SCCA-2), maspin, proteinase inhibitor 6 (PI-6), megsin, serpin B8 (PI-8), serpin B9 (PI-9), bomapin, yukopin, hurpin/headpin, antithrombin, heparin cofactor II, plasminogen activator inhibitor 1, glia-derived nexin, pigment epithelium derived factor, alpha 2-antiplasmin, complement 1-inhibitor, 47 kDa heat shock protein (HSP47), neuroserpin and pancpin.

In some embodiments of any of the embodiments described herein, the at least one protease inhibitor comprises at least one cysteine protease inhibitor. In some embodiments, the at least one protease inhibitor consists essentially of one or more cysteine protease inhibitor(s).

Examples of cysteine protease inhibitors which may be utilized in any one of the embodiments described herein include, without limitation, type 1 cystatins, type 2 cystatins, human cystatins C, D, S, SN, and SA, cystatin E/M, cystatin F, and type 3 cystatins (including kininogens).

In some embodiments of any of the embodiments described herein, the at least one protease inhibitor comprises at least one threonine protease inhibitor. In some embodiments, the at least one protease inhibitor consists essentially of one or more threonine protease inhibitor(s).

Examples of threonine protease inhibitors which may be utilized in any one of the embodiments described herein include, without limitation, bortezomib, MLN-519, ER-807446 and TMC-95A.

In some embodiments of any of the embodiments described herein, the at least one protease inhibitor comprises at least one aspartic protease inhibitor. In some embodiments, the at least one protease inhibitor consists essentially of one or more aspartic protease inhibitor(s).

Examples of aspartic protease inhibitors which may be utilized in any one of the embodiments described herein, include, without limitation, $\alpha_2$-macroglobulin, pepstatin A, aspartic protease inhibitor 11, aspartic protease inhibitor 1, aspartic protease inhibitor 2, aspartic protease inhibitor 3, aspartic protease inhibitor 4, aspartic protease inhibitor 5, aspartic protease inhibitor 6, aspartic protease inhibitor 7, aspartic protease inhibitor 8, aspartic protease inhibitor 9, pepsin inhibitor Dit33, and protease A inhibitor 3.

In some embodiments of any of the embodiments described herein, the at least one protease inhibitor comprises at least one metalloprotease inhibitor. In some embodiments, the at least one protease inhibitor consists essentially of one or more metalloprotease inhibitor(s).

Examples of metalloprotease inhibitors which may be utilized in any one of the embodiments described herein, include, without limitation, angiotensin-1-converting enzyme inhibitory peptide, antihemorrhagic factor BJ46a, beta-casein, proteinase inhibitor CeKI, venom metalloproteinase inhibitor DM43, carboxypeptidase A inhibitor, smpI, IMPI, alkaline proteinase, latexin, carboxypeptidase inhibitor, antihemorrhagic factor HSF, testican-3, SPOCK3, TIMP1, metalloproteinase inhibitor 1, metalloproteinase inhibitor 2, TIMP2, metalloproteinase inhibitor 3, TIMP3, metalloproteinase inhibitor 4, TIMP4, putative metalloproteinase inhibitor tag-225, tissue inhibitor of metalloprotease, WAP, kazal inhibitor, immunoglobulin, and kunitz and NTR domain-containing protein 1.

Examples of protease inhibitors which may be utilized in any one of the embodiments described herein also include, without limitation, AEBSF—HCl, ε-aminocaproic acid, α1-antichymotypsin, antipain, antithrombin III, α1-antitrypsin, APMSF (4-amidinophenyl-methane sulfonyl-fluoride), sprotinin, benzamidine, chymostatin, DFP (diisopropylfluoro-phosphate), leupeptin, 4-(2-Aminoethyl)-benzenesulfonyl fluoride hydrochloride, PMSF (phenylmethyl sulfonyl fluoride), TLCK (1-chloro-3-tosylamido-7-amino-2-heptanone), TPCK (1-chloro-3-tosylamido-4-phenyl-2-butanone), pentamidine isothionate, pepstatin, guanidium, α2-macroglobulin, a chelating agent of zinc, and iodoacetate.

In some embodiments of any one of the embodiments described herein, the total amount of a protease inhibitor in the at least two unit dosage forms according to any of the respective embodiments described herein is at least about 0.1 mg. In some embodiments, the total amount of a protease inhibitor in the at least two unit dosage forms described herein is at least about 0.2 mg. In some embodiments, the total amount of a protease inhibitor in the at least two unit dosage forms described herein is at least about 0.3 mg. In some embodiments, the total amount of a protease inhibitor in the at least two unit dosage forms described herein is at least about 0.4 mg. In some embodiments, the total amount of a protease inhibitor in the at least two unit dosage forms described herein is at least about 0.6 mg. In some embodiments, the total amount of a protease inhibitor in the at least two unit dosage forms described herein is at least about 0.8 mg. In some embodiments, the total amount of a protease inhibitor in the at least two unit dosage forms described herein is at least about 1 mg. In some embodiments, the total amount of a protease inhibitor in the at least two unit dosage forms described herein is at least about 1.5 mg. In some embodiments, the total amount of a protease inhibitor in the at least two unit dosage forms described herein is at least about 2 mg. In some embodiments, the total amount of a protease inhibitor in the at least two unit dosage forms described herein is at least about 2.5 mg. In some embodiments, the total amount of a protease inhibitor in the at least two unit dosage forms described herein is at least about 3 mg. In some embodiments, the total amount of a protease inhibitor in the at least two unit dosage forms described herein is at least about 5 mg. In some embodiments, the total amount of a protease inhibitor in the at least two unit dosage forms described herein is at least about 7 mg. In some embodiments, the total amount of a protease inhibitor in the at least two unit dosage forms described herein is at least about 10 mg. In some embodiments, the total amount of a protease inhibitor in the at least two unit dosage forms described herein is at least about 12 mg. In some embodiments, the total amount of a protease inhibitor in the at least two unit dosage forms is at least about 15 mg. In some embodiments, the total amount of a protease inhibitor in the at least two unit dosage forms described herein is at least about 20 mg. In some embodiments, the total amount of a protease inhibitor in the at least two unit dosage forms described herein is at least about 30 mg. In some embodiments, the total amount of a protease inhibitor in the at least two unit dosage forms described herein is at least about 50 mg. In some embodiments, the total amount of a protease inhibitor in the at least two unit dosage forms described herein is at least about 70 mg. In some embodiments, the total amount of a protease inhibitor in the at least two unit dosage forms described herein is at least about 100 mg.

In some embodiments of any one of the embodiments described herein, the total amount of a protease inhibitor in the at least two unit dosage forms described herein is in a range of from 0.1 to 1 mg. In some embodiments, the total amount of a protease inhibitor in the at least two unit dosage forms described herein is in a range of from 0.2 to 1 mg. In some embodiments, the total amount of a protease inhibitor in the at least two unit dosage forms described herein is in a range of from 0.3 to 1 mg. In some embodiments, the total amount of a protease inhibitor in the at least two unit dosage forms is in a range of from 0.5 to 1 mg.

In some embodiments of any one of the embodiments described herein, the total amount of a protease inhibitor in the at least two unit dosage forms described herein is in a range of from 0.1 to 2 mg. In some embodiments, the total amount of a protease inhibitor in the at least two unit dosage forms described herein is in a range of from 0.2 to 2 mg. In some embodiments, the total amount of a protease inhibitor in the at least two unit dosage forms is in a range of from 0.3 to 2 mg. In some embodiments, the total amount of a protease inhibitor in the at least two unit dosage forms described herein is in a range of from 0.5 to 2 mg. In some embodiments, the total amount of a protease inhibitor in the at least two unit dosage forms described herein is in a range of from 1 to 2 mg.

In some embodiments of any one of the embodiments described herein, the total amount of a protease inhibitor in the at least two unit dosage forms described herein is in a range of from 1 to 10 mg. In some embodiments, the total amount of a protease inhibitor in the at least two unit dosage forms described herein is in a range of from 2 to 10 mg. In some embodiments, the total amount of a protease inhibitor in the at least two unit dosage forms described herein is in a range of from 3 to 10 mg. In some embodiments, the total amount of a protease inhibitor in the at least two unit dosage forms described herein is in a range of from 5 to 10 mg.

In some embodiments of any one of the embodiments described herein, the total amount of a protease inhibitor in the at least two unit dosage forms described herein is in a range of from 1 to 20 mg. In some embodiments, the total amount of a protease inhibitor in the at least two unit dosage forms described herein is in a range of from 2 to 20 mg. In some embodiments, the total amount of a protease inhibitor in the at least two unit dosage forms described herein is in a range of from 3 to 20 mg. In some embodiments, the total amount of a protease inhibitor in the at least two unit dosage forms described herein is in a range of from 5 to 20 mg. In some embodiments, the total amount of a protease inhibitor in the at least two unit dosage forms described herein is in a range of from 10 to 20 mg.

In some embodiments of any one of the embodiments described herein, the total amount of a protease inhibitor in the at least two unit dosage forms described herein is in a range of from 10 to 100 mg. In some embodiments, the total amount of a protease inhibitor in the at least two unit dosage forms described herein is in a range of from 20 to 100 mg. In some embodiments, the total amount of a protease inhibitor in the at least two unit dosage forms described herein is in a range of from 30 to 100 mg. In some embodiments, the total amount of a protease inhibitor in the at least two unit dosage forms is in a range of from 50 to 100 mg.

In some embodiments of any one of the embodiments described herein, the total amount of a protease inhibitor in the at least two unit dosage forms described herein is in a range of from 10 to 200 mg. In some embodiments, the total amount of a protease inhibitor in the at least two unit dosage forms described herein is in a range of from 20 to 200 mg. In some embodiments, the total amount of a protease inhibitor in the at least two unit dosage forms described herein is in a range of from 30 to 200 mg. In some embodiments, the total amount of a protease inhibitor in the at least two unit dosage forms described herein is in a range of from 50 to 200 mg. In some embodiments, the total amount of a protease inhibitor in the at least two unit dosage forms described herein is in a range of from 100 to 200 mg.

In some embodiments of any one of the embodiments described herein, the total amount of a protease inhibitor in the at least two unit dosage forms described herein is at least about 10 kallikrein inactivator units (k.i.u.). In some embodiments, the total amount of a protease inhibitor in the at least two unit dosage forms described herein is at least about 12 k.i.u. In some embodiments, the total amount of a protease inhibitor in the at least two unit dosage forms described herein is at least about 15 k.i.u. In some embodiments, the total amount of a protease inhibitor in the at least two unit dosage forms described herein is at least about 20 k.i.u. In some embodiments, the total amount of a protease inhibitor in the at least two unit dosage forms described herein is at least about 30 k.i.u. In some embodiments, the total amount of a protease inhibitor in the at least two unit dosage forms described herein is at least about 40 k.i.u. In some embodiments, the total amount of a protease inhibitor in the at least two unit dosage forms described herein is at least about 50 k.i.u. In some embodiments, the total amount of a protease inhibitor in the at least two unit dosage forms is at least about 70 k.i.u. In some embodiments, the total amount of a protease inhibitor in the at least two unit dosage forms described herein is at least about 100 k.i.u. In some embodiments, the total amount of a protease inhibitor in the at least two unit dosage forms described herein is at least about 150 k.i.u. In some embodiments, the total amount of a protease inhibitor in the at least two unit dosage forms described herein is at least about 200 k.i.u. In some embodiments, the total amount of a protease inhibitor in the at least two unit dosage forms described herein is at least about 300 k.i.u. In some embodiments, the total amount of a protease inhibitor in the at least two unit dosage forms described herein is at least about 500 k.i.u. In some embodiments, the total amount of a protease inhibitor in the at least two unit dosage forms described herein is at least about 700 k.i.u. In some embodiments, the total amount of a protease inhibitor in the at least two unit dosage forms described herein is at least about 1000 k.i.u. In some embodiments, the total amount of a protease inhibitor in the at least two unit dosage forms described herein is at least about 1500 k.i.u. In some embodiments, the total amount of a protease inhibitor in the at least two unit dosage forms described herein is at least about 3000 k.i.u. In some embodiments, the total amount of a protease inhibitor in the at least two unit dosage forms described herein is at least about 4000 k.i.u. In some embodiments, the total amount of a protease inhibitor in the at least two unit dosage forms described herein is at least about 5000 k.i.u.

Herein and in the art, a "kallikrein inactivating unit" (k.i.u) refers to an amount of protease inhibitor that has the ability to inhibit 2 units of kallikrein by 50% (e.g., in aqueous solution at an optimal pH and solution volume for activity of the protease inhibitor).

In some embodiments of any one of the embodiments described herein, a weight ratio of protease inhibitor to therapeutically active agent in a unit dosage form according to any of the respective embodiments described herein is in a range of from 1:1 to 5:1 (protease inhibitor:therapeutically active agent). In some embodiments, a weight ratio of protease inhibitor to therapeutically active agent is in a range of from 5:1 to 10:1. In some embodiments, a weight ratio of protease inhibitor to therapeutically active agent is in a range of from 10:1 to 20:1. In some embodiments, a weight ratio of protease inhibitor to therapeutically active agent is in a range of from 20:1 to 30:1. In some embodiments, a weight ratio of protease inhibitor to therapeutically active agent is in a range of from 30:1 to 40:1. In some embodiments, a weight ratio of protease inhibitor to therapeutically active agent is in a range of from 40:1 to 50:1. In some embodiments, a weight ratio of protease inhibitor to therapeutically active agent is in a range of from 50:1 to 75:1. In some embodiments, a weight ratio of protease inhibitor to therapeutically active agent is in a range of from 75:1 to 100:1. In some embodiments, a weight ratio of protease inhibitor to therapeutically active agent is in a range of from 100:1 to 200:1. In some embodiments, a weight ratio of protease inhibitor to therapeutically active agent is in a range of from 200:1 to 300:1. In some embodiments, a weight ratio of protease inhibitor to therapeutically active agent is in a range of from 300:1 to 400:1. In some embodiments, a weight ratio of protease inhibitor to therapeutically active agent is in a range of from 400:1 to 500:1. In some embodiments, the protease inhibitor is soybean trypsin inhibitor.

Formulation of Composition Dosage Forms:

Each of the pharmaceutical composition dosage forms described herein, including multi-unit dosage forms, individual unit dosage and unit dosage forms within a multi-unit dosage form, optionally consists essentially of the functional ingredients described hereinabove (e.g., a therapeutically active agent, absorption enhancer, disintegrant(s) and/or protease inhibitor(s), or alternatively, the dosage form further comprises suitable pharmaceutically acceptable carriers and/or excipients.

Hereinafter, the phrases "physiologically acceptable carrier" and "pharmaceutically acceptable carrier", which may be interchangeably used, refer to a carrier or a diluent that does not cause significant irritation to an organism and does not abrogate the activity (e.g., biological activity) and properties of the functional ingredient (e.g., a therapeutically active agent). An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

In some embodiments of any one of the embodiments described herein, the unit dosage form is formulated as a solid composition. In some embodiments, the unit dosage form is formulated as a tablet, e.g., by compression.

Techniques for formulation and administration of drugs may be found in "Remington's Pharmaceutical Sciences," Mack Publishing Co., Easton, PA, latest edition, which is incorporated herein by reference.

Dosage forms of some embodiments of the invention, optionally including unit dosage forms, coatings and/or matrices in a multi-unit dosage form described herein (individually or in combination), may be manufactured by processes well known in the art, e.g., by means of conventional mixing, dissolving, granulating, dragee-making, levigating, emulsifying, encapsulating, entrapping or lyophilizing processes.

Dosage forms of some embodiments of the invention, optionally including unit dosage forms, coatings and/or matrices in a multi-unit dosage form described herein (individually or in combination), may thus be formulated in conventional manner using one or more physiologically acceptable carriers comprising excipients and auxiliaries, which facilitate processing of the active ingredients into preparations which, can be used pharmaceutically.

The dosage forms can be formulated readily by combining the active compounds with pharmaceutically acceptable carriers well known in the art as being suitable for oral administration. Such carriers optionally facilitate formulation of the pharmaceutical composition as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate; and/or lubricants such as talc or magnesium stearate.

In some embodiments of any one of the embodiments described herein, any one of the unit dosage forms described herein (e.g., formulated as a tablet or pellet) further comprises a lubricant. In some embodiments, the lubricant is included in a concentration of 5 weight percents or less, optionally 2 weight percents or less, and optionally about 1 weight percent. In some embodiments, the unit dosage form described herein (e.g., formulated as a tablet) consists essentially of the therapeutically active agent (as described herein), absorption enhancer, lubricant and optionally at least one protease inhibitor (as described herein). In some embodiments, the lubricant is magnesium stearate.

Dragee cores are optionally provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Dosage forms which can be used orally include push-fit capsules made of gelatin as well as soft, sealed capsules made of gelatin and a plasticizer, such as glycerol or sorbitol. The push-fit capsules may contain the active ingredients (optionally in a form of unit dosage forms within a multi-unit dosage form capsule, according to any of the respective embodiments described herein) in admixture with filler such as lactose, binders such as starches, lubricants such as talc or magnesium stearate and, optionally, stabilizers. In soft capsules, the active ingredients (optionally in a form of unit dosage forms within a multi-unit dosage form soft capsule, according to any of the respective embodiments described herein) may be dissolved or suspended in suitable liquids, such as fatty oils, liquid paraffin, or liquid polyethylene glycols. In addition, stabilizers may be added.

Pharmaceutical compositions suitable for use in context of some embodiments of the invention include compositions wherein a total amount of the therapeutically active agent is contained in the at least two unit dosage forms described herein in an amount effective to achieve the intended purpose. More specifically, the unit dosage forms together preferably comprise a therapeutically effective amount of therapeutically active agent, that is, an amount of therapeutically active agent effective to prevent, alleviate or ameliorate symptoms of a disorder or prolong the survival of the subject being treated. Furthermore, an amount of absorption enhancer is preferably effective for enhancing absorption of the therapeutically active agent (e.g., in a manner described herein); and an amount of protease inhibitor is preferably effective for inhibiting degradation of the therapeutically active agent (e.g., a polypeptide agent) by a protease.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the therapeutically active agent described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide levels (e.g., plasma levels) of the therapeutically active agent sufficient to induce or suppress a biological effect (minimal effective concentration, MEC). The MEC will vary for each preparation, but can be estimated from in vitro data. Dosages necessary to achieve the MEC will depend on individual characteristics. Detection assays can be used to determine plasma concentrations.

Depending on the severity and responsiveness of the condition to be treated, dosing can be of a single or a plurality of administrations, with course of treatment lasting from several hours to several weeks or until cure is effected or diminution of the disease state is achieved.

The amount of a composition to be administered will, of course, be dependent on the subject being treated, the severity of the affliction, the manner of administration, the judgment of the prescribing physician, etc.

Unit dosage forms and/or multi-unit dosage forms of some embodiments of the invention may, if desired, be presented in a pack or dispenser device, such as an FDA approved kit, which may contain one or more multi-unit dosage forms or unit dosage forms) according to any of the respective embodiments described herein) containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Dosage forms comprising a preparation of the invention may also be prepared (e.g., as described herein), placed in an appropriate container, and labeled for treatment of an indicated condition, as is further detailed herein.

Additional Definitions:

Herein, the term "polypeptide" refers to a polymer comprising at least 4 amino acid residues linked by peptide bonds or analogs thereof (as described herein), and optionally only by peptide bonds per se. In some embodiments, the polypeptide comprises at least 10 amino acid residues or analogs thereof. In some embodiments, the polypeptide comprises at least 20 amino acid residues or analogs thereof. In some embodiments, the polypeptide comprises at least 30 amino acid residues or analogs thereof. In some embodiments, the polypeptide comprises at least 50 amino acid residues or analogs thereof. The term "polypeptide" encompasses native polypeptides (e.g., degradation products, synthetically synthesized polypeptides and/or recombinant polypeptides), including, without limitation, native proteins, fragments of native proteins and homologs of native proteins and/or fragments thereof; as well as peptidomimetics (typically, synthetically synthesized polypeptides) and peptoids and semipeptoids which are polypeptide analogs, which may have, for example, modifications rendering the polypeptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein.

Peptide bonds (—CO—NH—) within the polypeptide may be substituted, for example, by N-methylated amide bonds (—N(CH$_3$)—CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the polypeptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The polypeptides of some embodiments of the invention (e.g., a therapeutically active agent and/or a protease inhibitor described herein) may also include one or more modified amino acids or one or more non-amino acid monomers (e.g. fatty acids, complex carbohydrates etc.).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
| --- | --- | --- | --- |
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Deys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl)glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |

TABLE 2-continued

| Non-conventional amino acid | Code | Non-conventional amino acid | Code |
|---|---|---|---|
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The polypeptides of some embodiments of the invention (e.g., a therapeutically active agent and/or a protease inhibitor described herein) are preferably utilized in a linear form, although it will be appreciated that in cases where cyclization does not severely interfere with polypeptide characteristics, cyclic forms of the polypeptide can also be utilized.

In some embodiments of any one of the embodiments described herein, the polypeptide is water-soluble.

Herein, the term "water-soluble" refers to a compound having a solubility of at least 1 gram per liter in an aqueous solution at pH 7.

Water-soluble polypeptides preferably include one or more non-natural or natural polar amino acids, including but not limited to serine and threonine which are capable of increasing polypeptide water-solubility due to their hydroxyl-containing side chain. Optionally, a homolog of a polypeptide is selected so as to be more water-soluble than the parent polypeptide, for example, by replacing one or more amino acids in the polypeptide with polar amino acids.

The polypeptides of some embodiments of the invention (e.g., a therapeutically active agent and/or a protease inhibitor described herein) may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the polypeptide compounds of some embodiments of the invention (e.g., a therapeutically active agent and/or a protease inhibitor described herein) involves solid phase peptide synthesis.

Large scale polypeptide synthesis is described by Andersson et al. [Biopolymers 2000; 55:227-250].

Herein, a "homolog" of a given polypeptide refers to a polypeptide that exhibits at least 80% homology, preferably at least 90% homology, and more preferably at least 95% homology, and more preferably at least 98% homology to the given polypeptide. In some embodiments, a homolog of a given polypeptide further shares a therapeutic activity with the given polypeptide. The percentage of homology refers to the percentage of amino acid residues in a first polypeptide sequence which match a corresponding residue of a second polypeptide sequence to which the first polypeptide is being compared. Generally, the polypeptides are aligned to give maximum homology. A variety of strategies are known in the art for performing comparisons of amino acid or nucleotide sequences in order to assess degrees of identity, including, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW etc. When utilizing BLAST and Gapped BLAST programs, default parameters of the respective programs may be used. Alternatively, the practitioner may use non-default parameters depending on his or her experimental and/or other requirements (see for example, the Web site having URL www(dot)ncbi(dot)nlm(dot)nih(dot)gov).

It is expected that during the life of a patent maturing from this application many relevant therapeutically active agents and many relevant treatments of conditions by therapeutically active agents will be developed, and the scope of the phrases "therapeutically active agent" and "condition treatable by . . . therapeutically active agent" are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials

8-Aminocaprylic acid was obtained from Alfa-Aesar.

Magnesium stearate was obtained from Merck.

O-acetylsalicyloyl chloride was obtained from Alfa-Aesar.

Soybean trypsin inhibitor (SBTI) was obtained from BBI solutions Ltd.

Teriparatide was purchased from Bachem.

SNAC (sodium 8-N-(2-hydroxybenzoyl)aminocaprylate) was prepared by reacting O-acetylsalicyloyl chloride with 8-aminocaprylic acid.

Example 1

Effect of Multi-Unit Formulation on Pharmacokinetic Variability

A Phase I pharmacokinetic study was performed in order to evaluate the effect of multi-unit oral formulation of parathyroid hormone (PTH) on pharmacokinetic variability.

Single unit formulations were composed of PTH(1-34) (0.69 mg or 2.07 mg), SNAC (sodium 8-N-(2-hydroxybenzoyl) aminocaprylate), soybean trypsin inhibitor (SBTI) and a small amount of magnesium stearate, in a form of a tablet.

Multi-unit formulations of 2.07 mg PTH(1-34) consisted of 3 single unit formulations (tablets) of 0.69 mg PTH(1-34). Multi-unit formulations of 0.69 mg PTH(1-34) consisted of a single unit formulation of 0.69 mg PTH(1-34) divided into 4 similar parts.

The study was performed on ten healthy Caucasian male volunteers who received two doses each (one dose with 0.69 mg PTH(1-34) and one with 2.07 mg PTH(1-34)) of a multi-unit oral formulation of recombinant PTH(1-34) (teriparatide) and of a single unit oral formulation of PTH(1-34), as well as a commercial subcutaneous injection of 20 μg PTH(1-34) (Forteo® teriparatide). The study consisted of screening, treatment and follow-up phases.

Blood samples for determination of PTH(1-34) plasma concentrations were taken at the indicated time points. Blood was drawn either by direct venipuncture or through an indwelling intravenous cannula. Whenever the latter was performed, the cannula was flushed with 1.5 ml normal saline after each sampling. In addition, to avoid sample dilution, 1 ml blood was drawn and discarded before the next sample (as long as the cannula was in place). Each blood sample for the pharmacokinetic assay was collected into a single tube containing EDTA (ethylenediaminetetraacetic acid) and placed on ice. Samples were maintained on ice for not more than 15 minutes from the start of collection to plasma separation. Plasma samples were transferred into appropriately labeled polypropylene tubes and stored at approximately −20° C. until shipment to a certified bioanalytical laboratory for quantification of PTH(1-34) concentrations.

TABLE 3

Maximal plasma concentration (Cmax) and time to maximal plasma concentration (Tmax) following oral or subcutaneous PTH(1-34) administration

| Tested formulation of PTH(1-34) | No. of subjects | Cmax (pg/ml) | Tmax (minutes) | Cmax CV (%) |
|---|---|---|---|---|
| subcutaneous injection | 10 | 184.2 ± 26.3 | 16 ± 1.8 | 45.2 |
| 0.69 mg - oral single-unit | 10 | 130.5 ± 56 | 14 ± 1.4 | 135.5 |
| 0.69 mg - oral multi-unit | 10 | 107 ± 26.6 | 16 ± 1.2 | 78.5 |
| 2.07 mg - oral single-unit | 10 | 342.6 ± 67.7 | 20 ± 1.9 | 62.5 |
| 2.07 mg - oral multi-unit | 10 | 235.6 ± 36.1 | 16.5 ± 1.2 | 48.4 |

Cmax CV (%) - coefficient of variation among the Cmax levels of different subjects.
Cmax and Tmax data presented as a mean ± standard error.

Figure 1B:
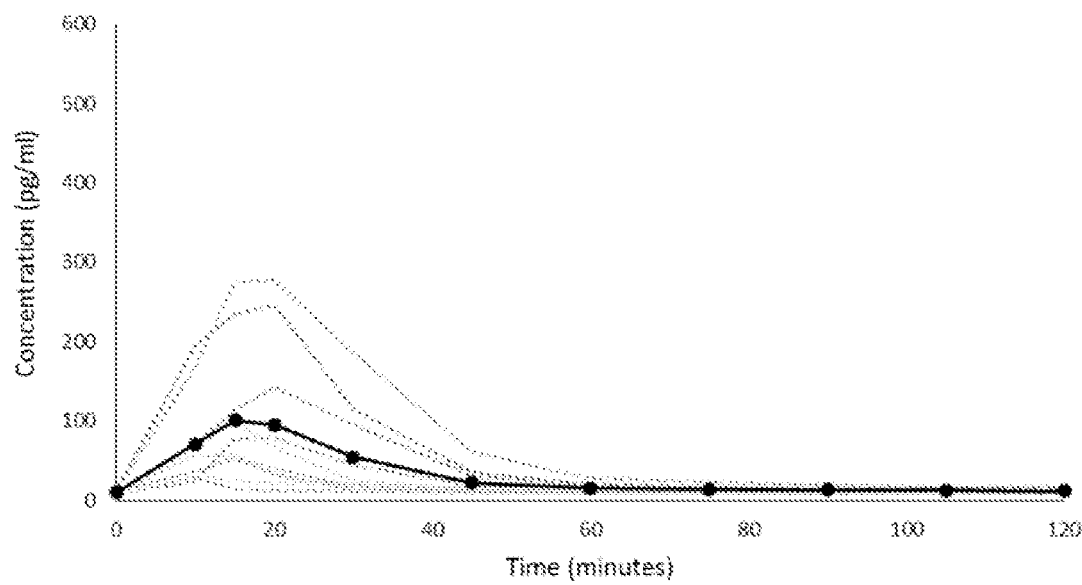

As shown in Table 3 and in FIGS. 1A and 1B, single unit oral formulations of 0.69 mg PTH(1-34) exhibited relatively large inter-subject variability, with a coefficient of variation (CV %) between the Cmax levels of different volunteers being 135.5%, whereas multi-unit oral formulations of 0.69 mg PTH(1-34) exhibited a reduced inter-subject variability, with a coefficient of variation (CV %) of 78.5%.

Figure 2A:
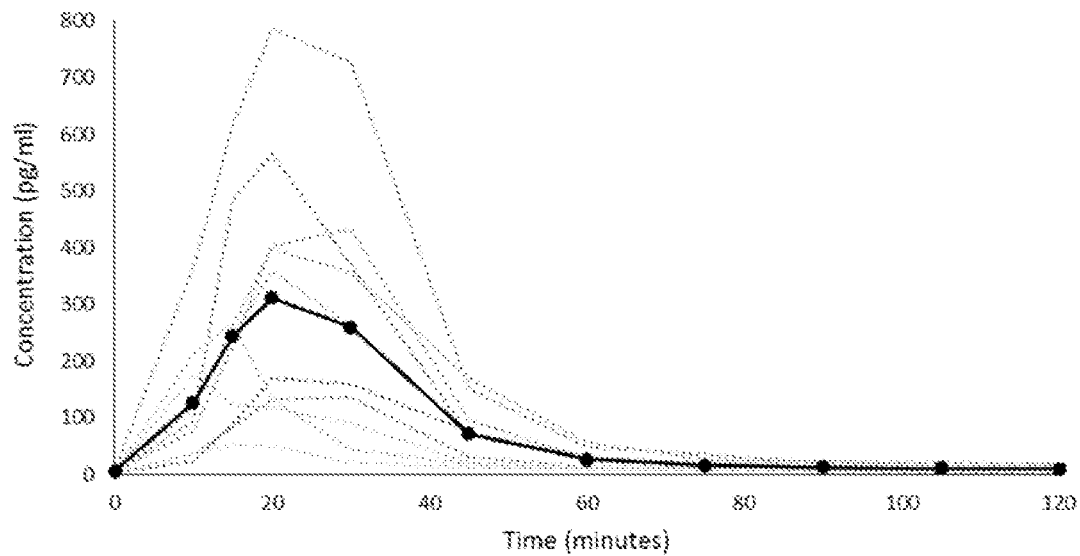
FIGS. 2A and 2B are graphs showing PTH(1-34) plasma concentrations as a function of time following oral administration of 2.07 mg PTH(1-34) in a multiple-unit formulation according to some embodiments of the invention (FIG. 2B) and in a in a single unit formulation (FIG. 2A) (black line represents average concentration among 10 subjects, and dashed lines represent concentrations for individual subjects).
Figure 2B:
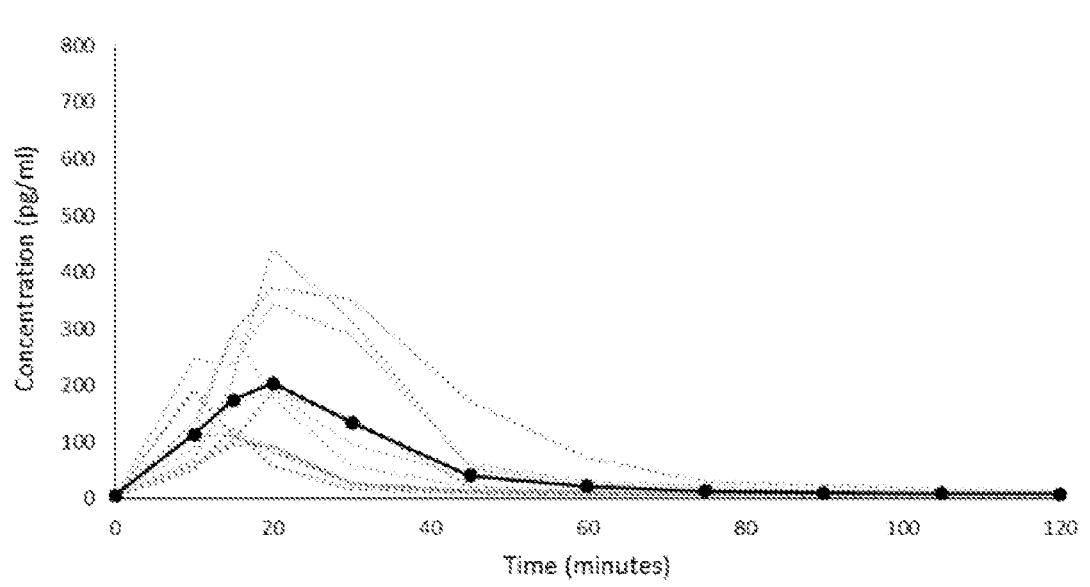
Figure 3A:
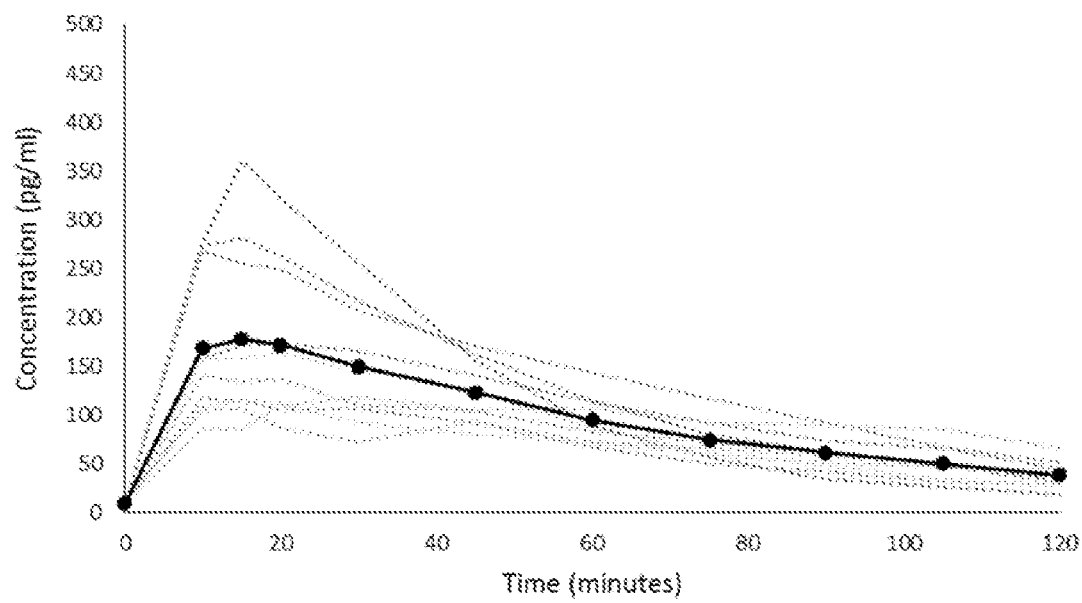
FIGS. 3A and 3B are graphs showing PTH(1-34) plasma concentrations as a function of time following subcutaneous injection of 20 μg PTH(1-34) (FIG. 3A) and following oral administration of 2.07 mg PTH(1-34) in a multiple-unit formulation according to some embodiments of the invention (FIG. 3B) (black line represents average concentration among 10 subjects, and dashed lines represent concentrations for individual subjects.
Figure 3B:
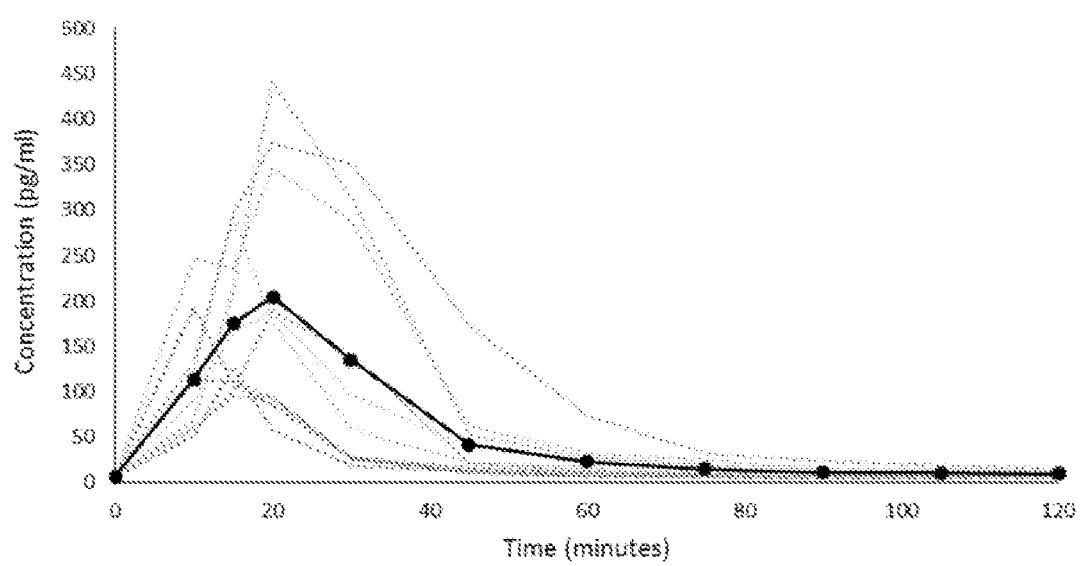

As shown in Table 3 and in FIGS. 2A and 2B, at doses of 2.07 mg PTH(1-34), single unit oral formulations exhibited a coefficient of variation (CV %) between the Cmax levels of different volunteers of 62.5%, whereas multi-unit oral formulations exhibited a reduced inter-subject variability, with a coefficient of variation (CV %) of 48.4%.

As shown in Table 3 and FIGS. 3A and 3B, the inter-subject variability between Cmax levels exhibited by multi-unit oral formulations of 2.07 mg PTH(1-34) was quite close to that exhibited by the commercial injectable formulation of PTH(1-34). In addition, the average Cmax levels for the two formulations were similar.

As further shown in FIG. 3B, the pharmacokinetic profile of the multi-unit oral formulation was characterized by a relatively brief presence of PTH(1-34) in plasma (as compared to PTH(1-34) following injection (FIG. 3A)). Such a pharmacokinetic profile may enhance the anabolic action of orally administered parathyroid hormone.

Multi-unit formulations also reduced the inter-subject variability total drug exposure, as determined by area under curve (AUC) (data not shown).

These results indicate that multi-unit oral formulation can reduce the high variability in absorption, which is common among drugs characterized by low bioavailability.

Example 2

Effect of Multi-Unit Formulation on Pharmacokinetics and Pharmacodynamics of Parathyroid Hormone (PTH)

A Phase Ib pharmacokinetic study was performed in order to further evaluate the effect of multi-unit oral formulation of parathyroid hormone (PTH) on pharmacokinetic variability and bioavailability, as well as on pharmacodynamic effects such as increase of serum calcium levels.

Multi-unit formulations of 1.5 mg recombinant PTH(1-34) (teriparatide) were prepared which consisted of 2 tablets of 0.75 mg or 3 tablets of 0.5 mg or 3 tablets. 1 tablet of 1.5 mg teriparatide served as a control dosage. Each tablet was composed of PTH(1-34) (in the indicated amount), SNAC (sodium 8-N-(2-hydroxybenzoyl) aminocaprylate), soybean trypsin inhibitor (SBTI) and a small amount of magnesium stearate, and all of the tested tablets were prepared from the same formulation blend.

The study was performed on healthy (as determined by medical history, physical examination, vital signs, electrocardiogram and laboratory tests at screening) non-smoking male volunteers, aged 18-50 years, with a body mass index of 18-30 kg/m$^2$, hemoglobin levels above 12.5 grams/dl, negative serology to Negative serology to HIV, hepatitis B and hepatitis C, blood pressure levels with no clinical significance, and hematology, chemistry and urinalysis values with no clinical significance or which do not reflect a medical condition which according to the physicians' judgment might confound the results of the study or pose additional risk to the subject by participation in the study. Subjects with active infections; known allergy or sensitivity to components of study treatment or study procedures (including soy or dairy), previous urolithiasis, history of drug or alcohol abuse, positive urinary screening results for drugs of abuse, treatment with a prescription medication or investigational product within the last month, clinically diagnosed psychiatric disorders that may interfere with patient study participation, medical history known or suspected to increase risks of adverse effects related to study drug, or concurrent therapy or chronic illness judged to interfere with the evaluation of the safety or efficacy of the study medication, were excluded from the study.

Blood samples for determination of PTH(1-34) plasma concentrations were taken at the time points of 0, 10, 15, 20, 30, 45, 60, 75, 90, 105, 120, 180, 240 and 300 minutes after administration, according to the procedures described in Example 1.

PTH(1-34) levels in the plasma samples were analyzed utilizing a PTH1-34 immunoassay (Immunodiagnostic Systems, UK). Levels of the serum calcium and albumin adjusted serum calcium of the same blood samples were analyzed by a Hadassah Medical Center clinical laboratory.

As shown in FIG. 4, each of the tested formulations was characterized by rapid absorption and elimination of PTH (1-34) following oral administration (characterized by a Tmax of 15-30 minutes), wherein the bioavailability increased along with an increase in the number of units of the administered formulation.

As shown in Table 4 below, the systemic exposure to PTH following administration, measured as area under curve (AUC), was strongly correlated to the number of administered units. As further shown therein, the maximal plasma concentration (Cmax) of the formulations was also strongly correlated to the number of administered units. The increase in Cmax and AUC of the three-unit formulation relative to Cmax and AUC of the single-unit formulation was statistically significant ($p=0.005$ and $p=0.01$, respectively).

These results indicate that the presence of multiple units in the formulation increases peptide bioavailability upon oral administration.

TABLE 4

Maximal PTH plasma concentration (Cmax), total exposure (AUC) to PTH, and increase in serum calcium concentration, following oral PTH(1-34) administration of formulations with one, two or three units.

| Formulation (1.5 mg PTH) | Cmax (pg/ml) | Cmax CV (%) | AUC (pg*min/ml) | Serum calcium increase (mg/dl) |
|---|---|---|---|---|
| Single unit (1.5 mg) | 145.1 ± 56 | 123 | 3481.2 ± 1843 | 0.07 ± 0.33 |
| Two units (0.75 mg each) | 374.9 ± 108 | 91 | 7976 ± 2556 | 0.12 ± 0.21 |
| Three units (0.5 mg each) | 480.8 ± 101 | 67 | 11369.4 ± 3719 | 0.32 ± 0.33 |

Cmax CV (%) - coefficient of variation among the Cmax levels of different subjects
Cmax, AUC and serum calcium data presented as a mean ± standard error.

As further shown in Table 4, the coefficient of variance of maximal plasma concentrations (Cmax CV) decreased upon increase in the number of the administered units.

These results indicate that the presence of multiple units in the formulation reduce absorption variability (in accordance with the results presented in Example 1).

As shown in FIG. 5 and in Table 4, the maximal increase (relative to baseline) in (albumin-adjusted) serum calcium levels was correlated to the number of units in the formulation, with the three-unit oral formulation of PTH(1-34) being considerably more effective than the single-unit oral formulation at enhancing the maximal relative increase in serum calcium levels.

These results indicate that the significant enhancement of absolute bioavailability associated with multi-unit formulations is associated with a corresponding enhancement of pharmacodynamic efficacy.

Taken together, the above results indicate that dividing a dose of a therapeutic agent into a multi-unit form in formulations such as described herein can reduce variability and increase absolute bioavailability and pharmacodynamic efficacy to a considerable degree which is directly correlated to the number of units on the formulation, in a relatively predictable manner. The reduction in variability and increase in bioavailability (and pharmacodynamic efficacy) overcomes two principal obstacles in oral delivery of biopharmaceuticals.

Example 3

Effect of Multi-Unit Formulation on Pharmacokinetic Variability

A Phase I pharmacokinetic study is performed in order to evaluate the effect of multi-unit oral formulation of parathyroid hormone (PTH) on pharmacokinetic variability and/or on pharmacodynamic effects such as increase of serum calcium levels.

Multi-unit formulations of 2 mg recombinant PTH(1-34) (teriparatide) are prepared which consist of 4 tablets, each tablet composed of 0.5 mg PTH(1-34), SNAC (sodium 8-N-(2-hydroxybenzoyl) aminocaprylate), soybean trypsin inhibitor (SBTI) and a small amount of magnesium stearate. For comparison, single unit formulations are prepared having the same composition as the multi-unit formulation (including 2 mg PTH(1-34), but in a form of a single tablet.

The study is performed on ten healthy Caucasian male volunteers who receive a dose of the multi-unit oral formulation of PTH(1-34) and the same dose as the single unit oral formulation of PTH(1-34). The study consists of screening, treatment and follow-up phases.

Blood samples for determination of PTH(1-34) plasma concentrations are taken at the time points of at 0, 10, 15, 20, 30, 45, 60, 75, 90, 105, 120, 180, 240 and 300 minutes after administration. Blood is drawn either by direct venipuncture or through an indwelling intravenous cannula, and plasma samples obtained, according to procedures described in Example 1 and/or 2. PTH(1-34) concentrations in the plasma samples and/or serum calcium levels are determined by a certified bioanalytical laboratory (e.g., as described in Example 1 and/or 2).

Pharmacokinetic variability is optionally quantified as Cmax and/or Tmax standard error and/or coefficient of variation between different volunteers (e.g., as described in Example 1 and/or 2). Bioavailability is optionally quantified as Cmax and/or AUC (e.g., as described in Example 2). Pharmacodynamic efficacy is optionally quantified as the maximal increase (relative to baseline) in (albumin-adjusted) serum calcium levels (e.g., as described in Example 2).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition multi-unit dosage form comprising at least three discrete unit dosage forms bound to one another by a coating and/or matrix, each of said unit dosage forms comprising a therapeutically active agent and an absorption enhancer, said therapeutically active agent having a molecular weight in a range of 1 kDa to 100 kDa and/or being a BCS Class III agent, said unit dosage forms together comprising a therapeutically effective amount of said therapeutically active agent and an effective amount of said absorption enhancer, wherein said coating and/or matrix is formulated for immediate release of said unit dosage forms upon oral administration, such that the multi-unit dosage form disintegrates in gastric fluid and/or in saliva within no more than 5 minutes to thereby release said unit dosage forms, wherein said absorption enhancer is selected from the group consisting of NAC (8-N-(2-hydroxybenzoyl) aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4-chlorobenzoyl)aminobutanoic acid) and salts thereof, and wherein at least 50 weight percents of the unit dosage forms consists of said absorption enhancer.

2. The multi-unit dosage form of claim 1, wherein said coating and/or matrix is soluble in gastric fluid and/or in saliva.

3. The multi-unit dosage form of claim 1, comprising from 3 to 10 of said discrete unit dosage forms.

4. The multi-unit dosage form of claim 1, wherein a maximal plasma concentration (Cmax) and/or AUC (area under curve) of plasma concentration of said therapeutically active agent upon oral administration of the multi-unit dosage form is characterized by an inter-subject coefficient of variation of less than 100%.

5. The multi-unit dosage form of claim 1, wherein a maximal plasma concentration (Cmax) of said therapeutically active agent upon oral administration of the multi-unit dosage form is characterized by an inter-subject coefficient of variation which is at least 20% less than an inter-subject coefficient of variation of a maximal plasma concentration (Cmax) of said therapeutically active agent upon oral administration of a unit dosage form consisting of a single unit dosage form having the same total composition as said discrete unit dosage forms.

6. The multi-unit dosage form of claim 1, wherein an AUC (area under curve) of plasma concentration of said therapeutically active agent upon oral administration of the multi-unit dosage form is characterized by an inter-subject coefficient of variation which is at least 20% less than an inter-subject coefficient of variation of an AUC of plasma concentration of said therapeutically active agent upon oral administration of a unit dosage form consisting of a single unit dosage form having the same total composition as said discrete unit dosage forms.

7. The multi-unit dosage form of claim 1, wherein an AUC (area under curve) of plasma concentration of said therapeutically active agent upon oral administration of the multi-unit dosage form is at least 20% greater than an AUC of plasma concentration of said therapeutically active agent upon oral administration of a unit dosage form consisting of a single unit dosage form having the same total composition as said discrete unit dosage forms.

8. The multi-unit dosage form of claim 1, comprising a total of at least 50 mg of said absorption enhancer in said at least three unit dosage forms.

9. The multi-unit dosage form of claim 1, wherein said therapeutically active agent has a molecular weight in a range of 1 kDa to 100 kDa.

10. The multi-unit dosage form of claim 1, wherein said therapeutically active agent is a BCS Class III agent.

11. The multi-unit dosage form of claim 1, wherein said therapeutically active agent is a polypeptide.

12. The multi-unit dosage form of claim 11, wherein said polypeptide is selected from the group consisting of parathyroid hormone and a fragment thereof.

13. The multi-unit dosage form of claim 11, wherein said polypeptide comprises teriparatide.

14. A method of treating a condition treatable by oral administration of parathyroid hormone or a fragment thereof in a subject in need thereof, the method comprising orally administering concomitantly at least three of a unit dosage form comprising less than 200 µg of parathyroid hormone or a fragment thereof, and an absorption enhancer selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4-chlorobenzoyl)aminobutanoic acid) and salts thereof, wherein said at least three of said unit dosage form are not comprised by a multi-unit dosage form and together comprise a therapeutically effective amount of said parathyroid hormone or a fragment thereof and an effective amount of said absorption enhancer.

15. A kit comprising a plurality of sets of at least three unit dosage forms, each of said sets being packaged individually in the kit, said unit dosage forms comprising a therapeutically active agent and an absorption enhancer, said therapeutically active agent having a molecular weight in a range of 1 kDa to 100 kDa and/or being a BCS Class III agent, wherein said at least three unit dosage forms are not comprised by a multi-unit dosage form and together comprise a therapeutically effective amount of said therapeutically active agent and an effective amount of said absorption enhancer, and wherein said absorption enhancer is selected from the group consisting of NAC (8-N-(2-hydroxybenzoyl) aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4-chlorobenzoyl)aminobutanoic acid) and salts thereof.

16. The kit of claim 15, further comprising instructions for concomitantly administering orally said unit dosage forms in one or more of said sets.

17. A method of treating a condition treatable by oral administration of a therapeutically active agent in a subject in need thereof, the method comprising orally administering to the subject the multi-unit dosage form of claim 1.

18. A method of treating a condition treatable by oral administration of a therapeutically active agent in a subject in need thereof, the method comprising orally administering concomitantly at least three pharmaceutical composition unit dosage forms, each of said unit dosage forms comprising said therapeutically active agent and an absorption enhancer, said therapeutically active agent having a molecular weight in a range of 1 kDa to 100 kDa and/or being a BCS Class III agent, wherein said at least three pharmaceutical composition unit dosage forms are not comprised by a multi-unit dosage form and together comprise a therapeutically effective amount of said therapeutically active agent and an effective amount of said absorption enhancer, wherein said absorption enhancer is selected from the group consisting of NAC (8-N-(2-hydroxybenzoyl)aminocaprylate), NAD (10-N-(2-hydroxybenzoyl)aminodecanoic acid), 5-CNAC (8-N-(5-chlorosalicyloyl)aminocaprylic acid), 4-MOAC (8-N-(2-hydroxy-4-methoxybenzoyl)aminocaprylic acid), 4-CNAB (4-N-(2-hydroxy-4-chlorobenzoyl)aminobutanoic acid) and salts thereof, and wherein at least 50 weight percents of said unit dosage forms consists of said absorption enhancer.

19. The method of claim 18, comprising reducing a variability of Cmax and/or AUC of plasma concentrations of said therapeutically active agent.

20. The method of claim 18, comprising increasing a Cmax and/or a bioavailability of said therapeutically active agent.

21. The method of claim 18, wherein a maximal plasma concentration (Cmax) and/or AUC (area under curve) of plasma concentration of said therapeutically active agent upon oral administration of said at least three pharmaceutical composition unit dosage forms is characterized by an inter-subject coefficient of variation of less than 100%.

22. The method of claim 18, comprising orally administering concomitantly from 3 to 10 of said unit dosage forms.

23. The method of claim 18, wherein said at least three unit dosage forms together comprise at least 50 mg of said absorption enhancer.

24. The method of claim 18, wherein said therapeutically active agent has a molecular weight in a range of 1 kDa to 100 kDa.

25. The method of claim 18, wherein said therapeutically active agent is a BCS Class III agent.

26. The method of claim 18, wherein said therapeutically active agent is a polypeptide.

27. The method of claim 18, wherein said polypeptide is selected from the group consisting of parathyroid hormone and a fragment thereof.

28. The method of claim 18, wherein said polypeptide comprises teriparatide.

29. The method of claim 27, wherein each of said pharmaceutical composition unit dosage forms comprises from 50 to 1000 µg of said parathyroid hormone or a fragment thereof.

30. The method of claim 18, comprising orally administering concomitantly at least four of said pharmaceutical composition unit dosage forms.

* * * * *